(12) United States Patent
Levetan

(10) Patent No.: US 8,911,776 B2
(45) Date of Patent: Dec. 16, 2014

(54) GENERATION OF NEW PANCREATIC BETA CELLS

(71) Applicant: Claresa Levetan, Bryn Mawr, PA (US)

(72) Inventor: Claresa Levetan, Bryn Mawr, PA (US)

(*) Notice: Subject to any disclaimer, the term of this patent is extended or adjusted under 35 U.S.C. 154(b) by 0 days.

(21) Appl. No.: 13/662,209

(22) Filed: Oct. 26, 2012

(65) Prior Publication Data
US 2014/0120154 A1    May 1, 2014

(51) Int. Cl.
| | | |
|---|---|---|
| *C12N 5/071* | (2010.01) | |
| *A61K 39/00* | (2006.01) | |
| *C07K 14/435* | (2006.01) | |
| *A61K 35/39* | (2006.01) | |

(52) U.S. Cl.
CPC .............. *C12N 5/0676* (2013.01); *A61K 39/00* (2013.01); *C07K 14/435* (2013.01); *A61K 35/39* (2013.01); *C12N 2501/998* (2013.01)
USPC ........ 424/450; 435/320.1; 435/353; 435/358; 435/352; 435/367; 435/365; 435/350; 435/366; 435/354; 530/350; 530/410; 514/21.2; 536/23.5

(58) Field of Classification Search
None
See application file for complete search history.

(56) References Cited

U.S. PATENT DOCUMENTS

| | | | |
|---|---|---|---|
| 2007/0087971 A1* | 4/2007 | Levetan et al. ................... | 514/14 |
| 2011/0082080 A1* | 4/2011 | Levetan ......................... | 514/7.3 |

OTHER PUBLICATIONS

Uniprot. D6W5J8_Human.*

* cited by examiner

*Primary Examiner* — Karlheinz R Skowronek
*Assistant Examiner* — Schuyler Milton
(74) *Attorney, Agent, or Firm* — James A. Italia; Italia IP

(57) ABSTRACT

The present invention relates to novel therapies for treatment of new and existing type 1 and type 2 diabetes, PreDiabetes, Latent Autoimmune Diabetes of Adulthood, and diseases of insulin deficiency, beta cell deficiency, insulin resistance and impaired glucose metabolism. In particular, the present invention identifies common peptides within the human Reg1a, Reg1b, Reg3a and Reg4, as signaling peptides for beta cell generation acting through the human Reg Receptor on the surface of human pancreatic extra-islet tissue. This invention identifies a specific binding region of the Reg Receptor from which peptidomimetics and stimulating antibodies have been developed for the generation of new beta cells which may be administered directly to patients with said conditions including type 1 diabetes, type 2 diabetes, PreDiabetes and other conditions of beta cell deficiency, and provides specific methodology for protecting new beta cells generated for usage in type 1 diabetes and Latent Autoimmune Diabetes of Adulthood. This invention also provides for ex-vivo generation and delivery of beta cells utilizing the inventions described within.

13 Claims, 22 Drawing Sheets

Generation of New Beta Cells

Generation of New Beta Cells

Structure of Human Reg
Reg 1a          Reg 3a          Hamster Reg3g
 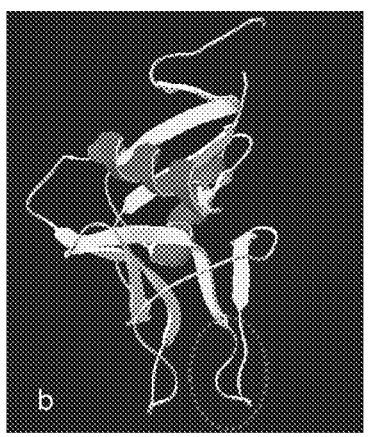 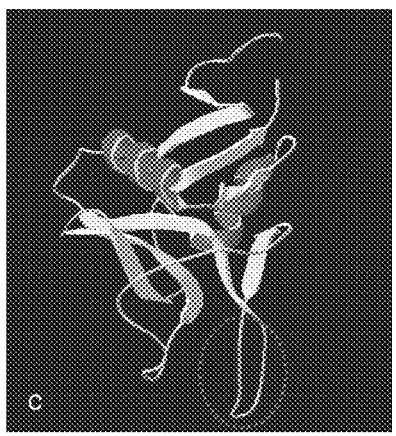
Red circled arm indicated homologous sequence region between human Reg1a, Reg3a and hamster Reg3gamma
Fig. 3

Homologous Peptide Sequences in Reg Genes

Human Reg 1a
MAQTSSYFMLISCLMFLSQSQGQEAQTELPQARISCPEGTNAYRSYCYYFNEDRETWVDADLYCQNMNSGNL
VSVLTQAEGAFVASLIKESGTDDFNVWIGLHDPKKNRRWHWSSGSLVSYKSWGIGAPSSVNPGYCVSLTS
STGFQKWKDVPCEDKFSFVCKFKN Human REG1b
MAQTNSFFMLISSLMFLSLSQGQESQTELPNPRISCPEGTNAYRSYCYYFNEDPETWVDADLYCQNMNSGNLV
SVLTQAEGAFVASLIKESSTDDSNVWIGLHDPKKNRRWHWSSGSLVSYKSWDTGSPSSANAGYCASLTSC
SGFKKWKDESCEKKFSFVCKFKN Human REG3a
MLPPMALPSVSWMLLSCLMLLSQVQGEEPQRELPSARIRCPKGSKAYGSHCYALFLSPKSWTDADLACQKRP
SGNLVSVLSGAEGSFVSSLVKSIGNSYSYVWIGLHDPTQGTEPNGEGWEWSSSDVMNYFAWERNPSTISS
PGHCASLSRSTAFLRWKDYNCNVRLPYVCKFTD Human REG IV
MASRSMRLLLLLSCLAKTGVLGDIIMRPSCAPGWFYHKSNCYGYFRKLRNWSDAELECQSYGNGAHLASILSLK
EASTIAEYISGYQRSQPIWIGLHDPQKRQQWQWIDGAMYLYRSWSG
KSMGGNKHCAEMSSNNNFLTWSSNECNKRQHFLCKYRP Hamster Reg 3 gamma
MLPMTLCRMSWMLLSCLMFLSWVEGEESQKKLPSSRITCPQGSVAYGSYCYSLILIPQT
WSNAELSCQMHFSGHLAFLLSTGEITFVSSLVK---NSLTAYQYIWIGLHDPSHGTLPNGS
GWKWSSSNVLTFYNWERNPSIAADRGYCAVLSQKSGFQKWRDFNCENE-LPYICKF

Fig. 4

Sequence ID: 8
Common to many species

| Human | W | I | G | L | H | D | P | T |
| Chimp | W | I | G | L | H | D | P | T |
| Mouse | W | I | G | L | H | D | P | T |
| Cow   | W | I | G | L | H | D | P | T |
| Sheep | W | I | G | L | H | D | P | T |

Fig. 5

919 Amino Acid Sequence of Reg Receptor with Reg Binding Site

```
MTGYTMLRNGGAGNGGQTCMLRWSNRIRLTWLSFTLFVILVFFPLIAHYYLTTLD
EADEAGKRIFGPRVGNELCEVKHVLDLCRIRESVSEELLQLEAKRQELNSEIAKLN
LKIEACKKSIENAKQDLLQLKNVISQTEHSYKELMAQNQPKLSLPIRLLPEKD
DAGLPPPKATRGCRLHNCFDYSRCPLTSGFPVYVYDSDQFVFGSYLDPLVKQAF
QATARANVYVTENADIACLYVILVGEMQEPVVLRPAELEKQLYSLPHWRTDGHN
HVIINLSRKSDTQNLLYNVSTGRAMVAQSTFYTVQYRPGFDLVVSPLVHAMSEPN
FMEIPPQVPVKRKYLFTFQGEKIESLRSSLQEARSFEEEMEGDPPADYDDRIIATL
KAVQDSKLDQVLVEFTCKNQPKPSLPTEWALCGEREDRLELLKLSTFALIITPGD
PRLVISSGCATRLFEALEVGAVPVVLGEQVQLPYQDMLQWNEAALVVPKPRVTE
VHFLLRSLSDSDLLAMRRQGRFLWETYFSTADSIFNTVLAMIRTRIQIPAAPIREEA
AAEIPHRSGKAAGTDPNMADNGDLDLGPVETEPPYASPRYLRNFTLTVTDFYRS
WNCAPGPFHLFPHTPFDPVLPSEAKFLGSGTGFRPIGGGAGGSGKEFQAALGG
NVPREQFTVVMLTYEREEVLMNSLERLNGLPYLNKVVVVWNSPKLPSEDLLWPD
IGVPIMVVRTEKNSLNNRFLPWNEIETEAILSIDDDAHLRHDEIMFGFRVWREARD
RIVGFPGRYHAWDIPHQSWLYNSNYSCELSMVLTGAAFFHKYYAYLYSYVMPQA
IRDMVDEYINCEDIAMNFLVSHITRKPPIKVTSRWTFRCPGCPQALSHDDSHFHE
RHKCINFFVKVYGYMPLLYTQFRVDSVLFKTRLPHDKTKCFKFI.
```

Fig. 6

Purification and Detection of Reg Receptor

Reg Receptor on Human Pancreatic Ductal Tissues

EIA Titer Assay: Results Summary

Investigator: Clarissa Leveson
Species: SPF Rabbit
Immunogen: CKKLT... + CKKSI...-KLH
Screening Ag: CKKSI...
Concentration: 1ug/mL

| Samples | Control (negative) | Control (positive) |
|---|---|---|
| Bleed Type: Test | Bleed Type: Pre | anti-ovalbumin (rabbit) |
| Bleed Date: 1/28/2011 | Bleed Date: 12/8/10 | diluted at 1:750,000 |

|  | 50% Titer |  | MeanValue (O.D.) |
|---|---|---|---|
| Animal ID | Samples | Control (negative) | Control (positive) |
| CD 133 | 36,000 | <100 | 0.667 |
| CD 134 | 125,000 | <100 |  |

Blank: 0.033
Blank Std Dev: 0.005
Noise Cutoff: 0.047
Operator: JH
Data Collected: 2/2/11 4:00 PM

Fig. 11

Protocol for Development of Antibodies to 21-amino acid sequence within the Reg Receptor Rabbit Protein Schedule of Events, 118 Day Standard Schedule of Events

| Day | Event |
|---|---|
| 0 | SPF Rabbit<br>Pre-Bleed (Avg. 5 ml serum)<br>1st SC: 250 micrograms with FCA |
| 21 | Boost SC: 125 micrograms with FIA |
| 31 | Test Bleed (Avg. 5 ml serum) |
| 32-38 | ELISA Titer Assay of Bleed * |
| 42 | Boost SC: 125 micrograms with FIA |
| 52 | Test Bleed (Avg. 5 ml serum) |
| 63 | Boost SC: 125 micrograms with FIA |
| 73 | Production Bleed (Avg. 20 ml serum) |
| 84 | Boost SC: 125 micrograms with FIA |
| 94 | Production Bleed (Avg. 20 ml serum) |
| 95-101 | ELISA Titer Assay of Bleed * |
| 105 | Boost SC: 125 micrograms with FIA |
| 115 | Production Bleed (Avg. 20 ml serum) |
| 118 | Terminal bleed (Avg. 50 ml serum) |

Fig. 12

Sequence ID: 1
100% Homology to other Mammals

| | | | | | | | | | |
|---|---|---|---|---|---|---|---|---|---|
| Human | N | V | W | I | G | L | H | D | P |
| Chimpanzee | N | V | W | I | G | L | H | D | P |
| Rat | N | V | W | I | G | L | H | D | P |
| Golden Hamster | N | V | W | I | G | L | H | D | P |
| W-C Gibbon | N | V | W | I | G | L | H | D | P |
| Sumatran Orangutan | N | V | W | I | G | L | H | D | P |
| Lowland Gorilla | N | V | W | I | G | L | H | D | P |
| W-T-E Marmoset | N | V | W | I | G | L | H | D | P |

Fig. 17

Sequence ID: 4
100% Homology to other Mammals

| Human | V | W | I | G | L | H | D | P |
|---|---|---|---|---|---|---|---|---|
| Chimpanzee | V | W | I | G | L | H | D | P |
| Rat | V | W | I | G | L | H | D | P |
| Golden Hamster | V | W | I | G | L | H | D | P |
| Guinea Pig | V | W | I | G | L | H | D | P |
| Rabbit | V | W | I | G | L | H | D | P |
| Pig | V | W | I | G | L | H | D | P |
| Sheep | V | W | I | G | L | H | D | P |
| Cow | V | W | I | G | L | H | D | P |
| W-C Gibbon | V | W | I | G | L | H | D | P |
| Sumatran Orangutan | V | W | I | G | L | H | D | P |
| Lowland Gorilla | V | W | I | G | L | H | D | P |
| W-T-E Marmoset | V | W | I | G | L | H | D | P |

Fig. 18

Sequence ID: 8
100% Homology to other Mammals

| | | | | | | | | |
|---|---|---|---|---|---|---|---|---|
| Human | W | I | G | L | H | D | P | T |
| Chimpanzee | W | I | G | L | H | D | P | T |
| Rat | W | I | G | L | H | D | P | T |
| Mouse | W | I | G | L | H | D | P | T |
| Golden Hamster | W | I | G | L | H | D | P | T |
| Guinea Pig | W | I | G | L | H | D | P | T |
| Rabbit | W | I | G | L | H | D | P | T |
| Pig | W | I | G | L | H | D | P | T |
| Sheep | W | I | G | L | H | D | P | T |
| Cow | W | I | G | L | H | D | P | T |
| W-C Gibbon | W | I | G | L | H | D | P | T |
| Sumatran Orangutan | W | I | G | L | H | D | P | T |
| Lowland Gorilla | W | I | G | L | H | D | P | T |
| European domestic ferret | W | I | G | L | H | D | P | T |

Fig. 19

Sequence ID: 7
100% Homology to other Mammals

| | | | | | | | |
|---|---|---|---|---|---|---|---|
| Human BRAD 4 | W | I | G | L | H | D | P |
| Chimpanzee | W | I | G | L | H | D | P |
| Rat | W | I | G | L | H | D | P |
| Mouse | W | I | G | L | H | D | P |
| Golden Hamster | W | I | G | L | H | D | P |
| Guinea Pig | W | I | G | L | H | D | P |
| Rabbit | W | I | G | L | H | D | P |
| Pig | W | I | G | L | H | D | P |
| Sheep | W | I | G | L | H | D | P |
| Cow | W | I | G | L | H | D | P |
| W-C Gibbon | W | I | G | L | H | D | P |
| Sumatran Orangutan | W | I | G | L | H | D | P |
| Lowland Gorilla | W | I | G | L | H | D | P |
| W-T-E Marmoset | W | I | G | L | H | D | P |
| European Domestic Ferret | W | I | G | L | H | D | P |

Fig. 20

Sequence ID: 14
100% Homology to other Mammals

| | | | | | | | | | |
|---|---|---|---|---|---|---|---|---|---|
| Human | V | W | I | G | L | H | D | P | T |
| Chimpanzee | V | W | I | G | L | H | D | P | T |
| Rat | V | W | I | G | L | H | D | P | T |
| Mouse | V | W | I | G | L | H | D | P | T |
| Golden Hamster | V | W | I | G | L | H | D | P | T |
| Guinea pig | V | W | I | G | L | H | D | P | T |
| Rabbit | V | W | I | G | L | H | D | P | T |
| Pig | V | W | I | G | L | H | D | P | T |
| Sheep | V | W | I | G | L | H | D | P | T |
| Cow | V | W | I | G | L | H | D | P | T |
| W-C Gibbon | V | W | I | G | L | H | D | P | T |
| Sumatran Orangutan | V | W | I | G | L | H | D | P | T |
| Lowland Gorilla | V | W | I | G | L | H | D | P | T |

Fig. 21

Sequence ID: 9
100% Homology to other Mammals

| | | | | | | | | | | | | | | | | | | |
|---|---|---|---|---|---|---|---|---|---|---|---|---|---|---|---|---|---|---|
| Human | C | K | K | S | I | E | N | A | K | Q | D | L | L | Q | L | K | N | V | I | S |
| Chimpanzee | C | K | K | S | I | E | N | A | K | Q | D | L | L | Q | L | K | N | V | I | S |
| Rat | C | K | K | S | I | E | N | A | K | Q | D | L | L | Q | L | K | N | V | I | S |
| Mouse | C | K | K | S | I | E | N | A | K | Q | D | L | L | Q | L | K | N | V | I | S |
| Mouse | C | K | K | S | I | E | N | A | K | Q | D | L | L | Q | L | K | N | V | I | S |
| Guinea Pig | C | K | K | S | I | E | N | A | K | Q | D | L | L | Q | L | K | N | V | I | S |
| Rabbit | C | K | K | S | I | E | N | A | K | Q | D | L | L | Q | L | K | N | V | I | S |
| Dog | C | K | K | S | I | E | N | A | K | Q | D | L | L | Q | L | K | N | V | I | S |
| Cow | C | K | K | S | I | E | N | A | K | Q | D | L | L | Q | L | K | N | V | I | S |
| Gray S-T Opossum | C | K | K | S | I | E | N | A | K | Q | D | L | L | Q | L | K | N | V | I | S |
| S-E Galago | C | K | K | S | I | E | N | A | K | Q | D | L | L | Q | L | K | N | V | I | S |
| W-C Gibbon | C | K | K | S | I | E | N | A | K | Q | D | L | L | Q | L | K | N | V | I | S |
| Sumatran Orangutan | C | K | K | S | I | E | N | A | K | Q | D | L | L | Q | L | K | N | V | I | S |
| Rhesus Macaque | C | K | K | S | I | E | N | A | K | Q | D | L | L | Q | L | K | N | V | I | S |
| Lowland Gorilla | C | K | K | S | I | E | N | A | K | Q | D | L | L | Q | L | K | N | V | I | S |
| W-T-E Marmoset | C | K | K | S | I | E | N | A | K | Q | D | L | L | Q | L | K | N | V | I | S |
| Horse | C | K | K | S | I | E | N | A | K | Q | D | L | L | Q | L | K | N | V | I | S |
| Tasmanian Devil | C | K | K | S | I | E | N | A | K | Q | D | L | L | Q | L | K | N | V | I | S |

Fig. 22

GENERATION OF NEW PANCREATIC BETA CELLS

CROSS REFERENCE TO RELATED APPLICATION

This application claims the benefit of priority to U.S. Provisional Application Ser. No. 61/706,225 filed Sep. 27, 2012.

FIELD OF THE INVENTION

The present invention relates to novel therapies derived from bioactive regions of the human Reg1a, Reg1b, Reg3a and Reg4 gene protein for the generation of new pancreatic beta cells for treatment of new and existing type 1 and 2 diabetes, PreDiabetes, and diseases of insulin deficiency, beta cell deficiency, insulin resistance and impaired glucose metabolism. This invention identifies unique bioactive peptide sequences within the human Reg1a, Reg1b, Reg3a and Reg4 proteins that bind directly to a human pancreatic receptor on extra-islet exocrine tissue inclusive of ducts, acinar cells and progenitor cells contained within these cells, resulting in new beta cell formation. This invention also identifies a specific binding region within the receptor for these peptides from which stimulating antibodies serving as peptidomimetics have been generated to form new beta cells.

This invention describes peptides contained within human Reg1a, Reg1b, Reg3a and Reg4 that have not been described in the prior art. These peptides bind to an extra-islet receptor resulting in downstream activation and regeneration of new beta cells. Formulations, derivatives, optimized forms including peptidomimetics of the peptides and stimulating antibodies to the Reg receptor are designed for the usage in the treatment of type 1 and 2 diabetes, PreDiabetes and conditions related to insulin deficiency, beta cell deficiency, insulin resistance and impaired glucose metabolism.

Previous work by this inventor has demonstrated that a human 14-amino human Reg3a peptide (Human Proislet Peptide/HIP) interacts with, but did not directly bind to the Reg Receptor, resulting in new beta cell formation. (See U.S. Pat. Nos. 7,989,415 and 7,393,919). This invention identifies peptide sequences within human Reg1a, Reg1b, Reg3a and Reg4 that directly bind to the Reg Receptor generating new beta cells. These peptides described in this invention are not contained within the peptide sequences of the prior art, including the human14-amino human Reg3a peptide (Human Proislet Peptide/HIP) (See U.S. Pat. Nos. 7,989,415 and 7,393,919), and the 15-amino acid Reg3 gamma hamster sequence (Islet Neogenesis Associated Protein (INGAP) (See U.S. Pat. Nos. 5,834,590 and 5,840,531). The peptides described in this invention bind directly to a cell surface receptor found in extra-islet exocrine tissue inclusive of ducts, acinar cells and progenitor cells contained within these cells, and activate downstream generation of beta cells. The 7-9 amino acid peptide sequences described in this invention are highly homologous and found within the Reg1a, Reg1b, Reg3a and Reg 4 proteins and bind to the Reg Receptor.

This invention also describes a specific 20-amino acid binding region within the Reg Receptor that is contained within its 919 amino acid Reg Receptor, which is where the Reg peptides provided within this invention, bind. This invention also includes the generation of stimulating antibodies from the 20-amino acid binding site within the 919-amino acid Reg Receptor, for usage in the generation of new beta cells. This invention also confirms that the previously described 14-amino acid Reg3a peptide (HIP) from prior art, interacts with but does not bind to, the identified 20-amino acid Reg Receptor. The peptides presented in this invention bind directly to this Reg Receptor on the cell surface of human extra-islet exocrine tissue inclusive of ducts, acinar cells and progenitor cells contained within these cells resulting in translocation from the cytoplasmic membrane to the nucleus. The peptides presented in this invention and the specific 20-amino acid binding region within this 919 amino acid human Reg Receptor, have not been described in the prior art.

This invention includes the generation of new pancreatic beta cells that are developed from formulations, derivatives, optimized forms including peptidomimetics of the peptides and stimulating antibodies to the Reg Receptor that are designed for the usage in the treatment of new onset and previously existing type 1 and 2 diabetes, PreDiabetes and related conditions of beta cell deficiency, insulin deficiency, insulin resistance and impaired glucose metabolism, with methods including the ex-vivo transformation from embryonic stem cells, human adult bone-marrow derived cells, induced pluripotent stem cells, mesenchymal stem cells, umbilical cord stem cells, or other stem cells and may include resident populations of endogenous stem cells that exist within the adult pancreas that are then administered to patients with new onset and previously existing type 1 and 2 diabetes, PreDiabetes and other conditions of beta cell deficiency, insulin deficiency, insulin resistance and impaired glucose metabolism, with routes of delivery to include, but are not limited to oral, intravenous, subcutaneous delivery with and without organ specific targeting and may include direct administration to the pancreas or liver.

This invention also identifies peptide sequences located in the binding region of Reg, which have 100% homology among humans and 14 other mammalian species. These peptide sequences are contained within the human Reg1a, human Reg1b, human Reg3a, human Reg 4 gene proteins and other mammalian species including: chimpanzee, cow, sheep and mouse, reflecting the evolutionary importance of the peptide sequences identified in this invention. This invention demonstrates direct binding of human Reg peptides to the Reg Receptor, which has not been described in the prior art.

This invention also provides specific methodology for an innovative therapy for accelerated generation of beta cells including methodology for treatment and reversal of type 1 and 2 diabetes and inclusive of the methods of treatment for PreDiabetes and diseases of beta cell deficiency by the use of Reg peptides and/or formulations, derivatives, optimized forms, peptidomimetics, and stimulating antibodies to the Reg Receptor for direct administration to a patient for treatment of new onset and previously existing type 1 and 2 diabetes, Latent Autoimmune Diabetes of Adulthood (LADA), those at risk for type 1 diabetes who have autoimmune markers including those who are Glutamic Acid Decarboxylase-65 (GAD65) antibody positive, PreDiabetes and diseases of hyperglycemia, glucose intolerance and beta cell impairment or deficiency, insulin resistance and associated conditions including, obesity, obesity prior to the development of diabetes, obesity in children leading to PreDiabetes, childhood diabetes, both type 1 and 2 and other conditions of insulin impairment and resistance including but not limited to polycystic ovarian syndrome, nonalcoholic steatohepatitis, hyperlipidemia and hypertriglyceridemia. In addition this invention provides detailed methods for providing the optimal milieu for generation of new beta cells and methods for protection of new beta cells generated by this invention and also describe the usage of Reg peptides and/or formulations, derivatives, optimized forms, peptidomimetics, and stimulating antibodies to the Reg Receptor for the ex-vivo generation of new beta cells.

REFERENCE TO SEQUENCE LISTING

Pursuant to 37 CFR Section 1.52(e)(5), filed herewith, the contents of which are incorporated by this reference, is a sequence listing titled, "betacellssequencelisting_ST25". The text file was created on Oct. 26, 2012 and is 18 KB.

BACKGROUND OF THE INVENTION

Diabetes is one of the most serious health issues facing humanity with The World Health Organization reporting that approximately 346 million people worldwide have already been diagnosed with diabetes, making it a global challenge. Diabetes is a chronic disease that manifests when insulin production by the beta cells of the pancreas is insufficient. Among type 2 diabetes patients, there is a 50-80% reduction in beta cell mass by the time of diagnosis compared to a reduction in beta mass by 90% or more among type 1 patients, who commonly have an autoimmune component to their beta cell loss. Two recent NIH studies, one in children and adolescents and the other in adults demonstrate that intensive lifestyle interventions designed to improve and impact diabetes simply have no effect in children and adolescents and cannot be sustained over time among adults.

The TODAY Study Group. N Engl J. Med. 2012 Apr. 29. [Epub ahead of print]. Diabetes Research Program Prevention Group, Lancet. 2009; 374(9702): 1677-1686. Among children and adolescents with type 2 diabetes, therapy with metformin or lifestyle interventions did not improve diabetes control or the necessity to go the insulin therapy. The TODAY study illustrates the need for new insulin-secreting beta cells to delay or prevent the adverse vascular complications of diabetes. Despite the many new treatment and technological armamentariums for diabetes, the diabetes-related complications including retinopathy, blindness, neuropathy, amputations, renal insufficiency and dialysis, along with the macrovascular complications including heart attack, stroke and peripheral vascular disease have risen among patients with diabetes. For example, recent studies among patients with type 1 utilizing advances including the use of glucose sensors and insulin pumps did not improve hemoglobin A1C levels as much as those seen in the DCCT trial conducted more two decades ago when there were much more limited treatment options. The DCCT Research Group. N Engl J. Med. 1993; 329(14):977-986, Bergenstal R M et al, N Engl J Med, 2010; 363(4):311-320. Bergenstal R M, et al, Diabetes Care. 2011; 34(11):2403-2405.

There is a dire need to restore new beta cells and maintain beta cell mass among type 1 and type 2 diabetes. The loss of endogenous insulin is directly correlated with a multiplicity of atherogenic risk factors for microvascular and macrovascular complications. Lack of insulin, which is the a hallmark of diabetes results not only in elevated glucose levels, but also results in a large number and wide complexity of metabolic abnormalities. For example, lack of insulin results in diminished activation of lipoprotein lipase resulting in increased levels of triglyceride-rich lipoproteins including chylomicrons and very low-density lipoproteins.

The leading hypothesis of how new beta cells can be formed in both children and adults is based upon the original works of scientists nearly a century ago who identified that in acute pancreatic injury there is new beta cell growth. Frederick Banting, discovered insulin in 1921, by clamping the pancreatic ducts to induce the formation of new pancreatic cells. Dr. Banting collected the pancreatic secretions after acute pancreatic ligation and these secretions became known as insulin. Banting F G and Best C H. J Lab Clin Med. 1922; 7:464-472. This work was supported by several earlier scientists, who described that although the population of beta cells is primarily formed during embryogenesis, there is the ability to grow new beta cells postnatally, through a process of transformation of ductal cell tissue into insulin-producing tissue. By 1920, the regenerative powers of the pancreas were well described. Frederick Banting attributes his studies leading to the discovery of insulin on the work of Moses Barron who documented that regeneration of injured pancreatic tissue manifests from the pancreatic ducts. Barron M. Surg Gynec Obstet. 1920; 19:437-448. Prior to the widespread availability of insulin, surgeons performed partial pancreatectomies on diabetic children in the hopes of stimulating beta cell regeneration. DeTakats G. Endocrinology. 1930; 14:255-264. Benefits from these novel procedures were described, but were short-lived, likely because of ongoing autoimmune destruction.

The ability to generate fully-functional pancreatic beta cells, through the differentiation of non-endocrine cells has now been shown by more than a dozen research groups including The Section of Islet Cell and Regenerative Biology at Joslin Diabetes Center at Harvard University and The Departments of Beta Cell Regeneration at the Hagedorn Research Institute in Denmark.

Over the past several decades, the regenerating gene (Reg or REG) family has emerged among many species, including humans, as a key initiating factor in the process of beta regeneration from nonendocrine tissue within the pancreas. Levetan C., 2010, J Diabetes; 2(2):76-84. The Reg genes are associated with beta regeneration and are upregulated in the pancreas during embryogenesis when the pancreas is being populated with beta cells for the first time. After fetal development when the pancreas is populated with endocrine cells for the first time, the Reg genes are usually undetectable, but are upregulated in response to acute pancreatic injury including pancreatic stones, pancreatitis, pancreatic duct ligation and wrapping, partial pancreatectomy and pregnancy.

It is also known from the Human Genome Project that there are many genes that are responsible for making cells of the different organs and populating organs for the first time (such as the brain, heart, kidney and pancreas) and such genes are expressed almost exclusively during embryological development. The regenerating gene family of proteins (Reg) are expressed almost exclusively during embryological development and then only expressed when there is acute pancreatic injury as a mechanism to help repair the injured organ. Typically in both type 1 and 2 diabetes, the rate of tissue demise exceeds the rate of regeneration despite Reg gene upregulation. To date, 17 Reg family genes have been identified. Identified members of the human REG gene family (REG) include Regenerating islet-derived 1 alpha (REG1α or REG1a), REG 1β, also known as REG 1b, REG 3α, also known as REG 3a, REG 3β, also known as REG 3b and REG 4.

This invention identifies and confirms peptide sequences that are highly conserved and 100% identical within the human Reg 1a, human Reg1b, human Reg3a and human Reg 4 proteins and identical Reg peptide sequences within four other mammalian species. This inventor has previously described the role of a 14-amino acid Human Reg3a peptide in pancreatic islet development. This present invention, identifies peptide sequences contained within the human Reg1a, Reg1b, Reg3a and Reg4 that are not contained within the previously described, prior art human 14-amino acid peptide Reg3a protein and the 15-amino acid hamster Reg3gamma protein, resulting in beta cell regeneration. The Reg peptides described within this invention, bind directly to the Reg Receptor on pancreatic extra-islet ductal tissue. In contrast to the earlier study of the 14-amino acid peptide, which is shown to (Levetan C S et al, Endocr Pract. 2008; 14(9):1075-1083) interact with the Reg receptor but does not directly bind to it.

This invention also specifically identifies a binding region within human Reg Receptor and the bioactive peptides within the Reg gene protein that bind directly to the Reg Receptor that are not included in the prior art of the 15-amino acid hamster Reg3gamma sequence known as Islet Neogenesis Associated Protein/INGAP or the 14-amino acid human Reg3a peptide known as Human Proislet Peptide/HIP. This invention demonstrates the utility of these peptides, derivatives, peptidomimetics and stimulatory antibodies that have been generated from the specific binding regions of the Reg Receptor for the generation of new human beta cells Kapur, Watanabe, Zenilman and others have provided evidence that Reg peptides play a direct role in stimulating beta cell formation from non-endocrine pancreatic tissue. Kapur R et al Islets. 2012; 4(1), Watanabe T et al Proc Natl Acad Sci USA. 1994, 26; 91(9):3589-92. Zenilman M E, et al Pancreas. 1998; 17:256-261. The previously described human 14-amino acid peptide (Human Proislet Peptide) and 15-amino acid peptide (hamster) (Islet Neogenesis Associated Protein/INGAP) from the human and hamster Reg3 gene protein have demonstrated the ability to not only restore normoglycemia via restoration of new beta cells in animal models, but also to generate new beta cells in humans via the transformation of extra-islet ductal tissue into new endocrine cells including demonstrating the formation of new beta cells from human pancreatic ductal tissue. Levetan C S et al, Endocr Pract. 2008; 14(9):1075-1083, Rosenberg L et al, Diabetologia. 1996; 39:256-262, Li J et al, Peptides. 2009; 30(12):2242-2249, Dungan K M et al, Diabetes Metab Res Rev. 2009; 25(6):558-565.

Previously, this inventor demonstrated that a human Reg3a gene protein has successfully been administered to human pancreatic ductal tissue devoid of islets resulted in a significant increase in insulin concentrations indicating new beta cell formation resulted a 3-fold rise in total beta cells staining insulin in STZ-rendered diabetic mice. Levetan C S., et al, Endocr Pract. 2008; 14(9):1075-1083. Reg3a protein and placebo-treated mice underwent an overnight fast and a fasting glucose level on the morning of day 39 of treatment. Fasting glucose levels were 258.00±84.5 mg/dl in the placebo group compared a fasting glucose 111.00±11.4 mg/dL (P=0.020) in the Reg3a protein treated mice.

Two studies by separate investigators have shown the ability of Reg peptide to transform human extra-islet pancreatic exocrine tissue into new beta cells, in vitro. These studies were conducted by a methodology utilized in pancreatic islet transplantation, in which the pancreatic endocrine beta cells are separated from the exocrine ductal tissue and the exocrine ductal tissue are shown to transform into new beta cells in the presence of Reg peptide. Li J, et al. Peptides 2009; 30:2242-9, Assouline-Thomas B G, Diabetes 2008, 57(Suppl; 1) A2413. Using the current gold-standard (BrdU labeling), which distinguishes whether new beta cells are formed by the budding from pre-existing beta cells versus being formed from extra-islet ductal exocrine tissue were conducted in rodents using BrdU labeling of the beta cell lineage, which can distinguish whether new beta cells are being derived from replicating beta cells versus beta cells being formed from non-endocrine, extra-islet pancreatic exocrine tissue. Kapur R, et al, Islets. 2012; 4(1).

The Section of Islet Cell and Regenerative Biology at Joslin Diabetes Center found that the 15-amino acid hamster INGAP Reg3 gamma peptide was present in the newest beta cells and islets that were formed directly from branching proliferating extra-islet ducts, which also confirms that mechanism of action of Reg peptide is to form new beta cells from extra-islet exocrine tissue. Guo L et al, Diabetes. 2010, 59(suppl; 1) A2589. When Reg is inhibited by the administration of a blocking antibody in an animal model of pancreatic injury, there was attenuated recovery, also confirming that Reg's role is both protective and regenerative during acute pancreatic injury. Viterbo D, et al. JOP. 2009; 10(1):15-23.

The Departments of Beta Cell Regeneration at the Hagedorn Research Institute and Peptide and Protein Chemistry at Novo Nordisk reported a 2-fold increase in the volume of new small islets developing from non-endocrine tissue resulting from the treatment with both the human 14 amino acid Reg3a peptide, HIP, and the 15-amino acid Reg3gamma hamster peptide, INGAP. Kapur R, et al, Islets. 2012; 4(1):Epub. Five days after treatment with both the 14-amino acid human Reg3a peptides, HIP, and the 15-amino acid hamster Reg3gamma peptide, INGAP, there were increased levels of new islet markers necessary for islet formation, including NGN3, NKX6.1, SOX9, and INS, indicating that REG is a catalyst for beta cell neogenesis. Kapur R, et al, Islets. 2012; 4(1). Similar to these findings, other data support that the Reg protein is an initiating factor to downstream regulation of new beta cells. Levetan C., 2010, J Diabetes; 2(2):76-84. For example, when Reg is initially expressed, PDX-1, PAX1, Ngn3, Nkx6.1, Sox9 and Ins, are not expressed, and once Reg is present, PDX-1, PAX1, Ngn3, Nkx6.1, Sox9 and Ins and other beta cell proliferation factors become present demonstrating that Reg activates downstream factors necessary for beta cell regeneration. Vukkadapu S S Physiol Genomics 2005:21, 201-211, Kapur R., et al., Islets. 2012; 4(1):Epub. Gurr and colleagues confirmed positive Reg staining in ductal epithelium in acutely diabetic NOD mice and in the pancreas of a type 1 healthy cadaveric human pancreata or in healthy mice.

The organ specificity of Reg proteins to the pancreatic ducts has been illustrated by tagged Reg protein labeled with fluorescein isothiocyanate that was administered via intraperitoneal injection to rodents. The only organ that had fluorescent staining was the pancreas with labeling only found specifically to be within the nonendocrine pancreatic ductal populations, again confirming that the mechanism of action of Reg is transformation of extra-islet ductal cells into beta cells. Pittenger G L et al, Diabetologia 2009; 52 (5):735-738. There are now numerous studies confirming that the mechanism of action of the Reg peptides is to transform extra-islet exocrine ductal tissue into new islets rather than the newly formed beta cells resulting from the budding of existing beta cells.

Both the 14-amino acid Reg3a peptide, HIP, and 15-amino acid Reg3gamma peptide, INGAP, are currently in human clinical trials. Human clinical trials with the 15-amino acid hamster peptide have already resulted in an increase in stimulated C-peptide by 27% (p=0.0057) in type 1 patients. Dungan K M et al, Diabetes Metab Res Rev. 2009; 25(6):558-565.

The REG genes encode proteins secreted by the exocrine pancreas, which has been associated with beta cell regeneration in rodents. Terazono K., et al., J Biol Chem (1988), 263: 2111-2114. REG1a, REG1b, REG3a and REG4 belong to the C-lectin family and are randomly clustered on 2p12. They share structural and some functional properties and encode proteins that are members of the Reg family with sequence homology as described in this invention. Their products are secretory proteins of the C-type lectin superfamily that are involved in beta cell regeneration and proliferation.

Specifically for type 1 diabetes, this invention describes a novel approach for the reversal of the disease by administering an immune tolerance agent prior to the initiation of Reg peptides described in this invention. To date, more than 100 different immune agents have been administered to type 1 diabetes rodent models, as well as to human subjects with new onset type 1 diabetes. Although many have been successful in the reversal of diabetes in rodents, none have successfully reversed diabetes in man and led to insulin independence. There have been several agents demonstrating promise in terms of immune blockade, but beta regeneration is too slow to render patients insulin-free despite the blocked immune attack on beta cells. This invention combines the administering of an immune tolerance agent prior to the administration of the Reg peptide for beta regeneration in order to accelerate the regeneration process for successful reversal of diabetes.

Both the sequences and the 3-Dimensional Structures of the human Reg gene proteins are very similar in that each has a similar binding arm that protrudes from the main structure that is the binding region for the Reg Receptor. Human Reg1a contains 166 amino acids. Human Reg1b contains amino 166 acids. Human Reg3a contains 174 amino acids. Human Reg4 contains 158 amino acids.

This invention identifies peptide sequences that are within the human Reg1a, human Reg1b, human Reg3a and human Reg4 proteins that have not been previously described for the usage of beta cell generation. This invention specifically demonstrates that homologous peptides within the human Reg1a, human Reg1b, human Reg3a and Reg4 gene protein bind directly to the human Reg receptor, which results in the acceleration of the generation of new beta cells from pancreatic ductal tissue. Although both the 15-amino acid hamster sequence (Islet Neogenesis Associated Protein/INGAP) and 14-amino acid human Reg3a peptide (Human Proislet Peptide) act through the Reg receptor to generate new beta cells, neither of these peptides directly binds directly to the human Reg receptor, which is confirmed in this invention. Also identified is a bioactive domain within the Reg receptor that is immunogenic and stimulatory antibodies to this binding site have been generated.

A putative Reg Receptor initially described in rodents, was found by this inventor to be present in human pancreatic ductal tissue. The prior art described that the 14-amino acid human Reg3a peptide (HIP) interacted with the human Reg Receptor resulting in downstream signaling and generation of new beta cell formation. Levetan C S., et al, Endocr Pract. 2008; 14(9):1075-1083. This present invention demonstrates that the 7-9 amino acid human Reg peptides bind directly to the Reg Receptor and are not contained within the prior art, 14-amino acid human Reg 3a peptide or the 15-amino acid hamster Reg3gamma peptide.

The Reg Receptor and has been described and known as hereditary Multiple Exostoses Gene Isolog with other names describing this receptor including REG RECEPTOR, Reg Receptor, BOTV, BOTY, DKFZp686C2342, exostoses (multiple)-like 3, Exostosin-like 3, EXT-related protein 1, EXTL1, HHREG RECEPTOR, EXTR1, EXTL3 Glucuronyl-galactosyl-proteoglycan-4-alpha-N-acetylglucosaminyltransferase, KIAA0519, Multiple exostosis-like protein 3, REGR and RPR. exostoses (multiple-like 3, Glucuronyl-galactosyl-proteoglycan, 4-alpha-N-acetylglucosaminyltransferase, exostosin-like3, Hereditary multiple exostoses gene isolog, reg receptor, Multiple exostosis-like protein 3, and EC2.4.1).

The receptor was named for its similarities to the Exostoses family of genes by homology screening, but it was specifically noted that this receptor is not derived from the Exostoses (EXT and EXTL) genes. Rather, the Reg Receptor protein (FIG. 4) was categorized as a member of the Exostosin family because it demonstrates a 52% homology to the 262 amino acid C-terminal of the Exostosin-like 2 protein and a 40% homology with the 242 amino acid C-terminal of the Exostosin-like 1 protein, yet there is no homology of Reg Receptor to the N-terminal regions of Exostosin-1 or 2. Kobayashi S. et al., Anat. Embryol. 207:11-15, 2003. Reg Receptor was initially isolated and described by Van Hul and colleagues in 1998 as a 919 amino acid protein Reg receptor contains a 23 amino acid unique N-terminal region containing a transmembrane domain (residues 28-51) and a short intracellular region at the N terminus. Reg Receptor is located on chromosome 8p21. Saito T. et al, Biochem Biophys Res Commun. 1988, 242(1):61-66, Van Hul W et al., Genomics. 1998; 47(2):230-7.

The N-terminal region (residues 1-656) of the Reg Receptor has no homology to any other members of this family of genes. The 1.6-kbp cDNA, which was initially isolated in the screening of the rat islet cDNA expression library as a Reg-binding protein, contained the N-terminal region alone (amino acid residues 1-332). Kobayashi S. et al., Anat. Embryol. 207:11-15, 2003. Because no other members of the EXT family bind to Reg proteins, the Reg binding domain is shown in this invention within the N-terminal region of Reg Receptor.

While it has been recognized that is a putative Reg Receptor in rodents, this invention is the first to demonstrate peptides not contained within the human 14-amino acid Reg3a, and contained within the human Reg1a, Reg1b, Reg3a and Reg4 protein and bind directly to the Reg Receptor leading to new beta cell formation.

Findings by this inventor demonstrate that the Reg Receptor plays a key regulatory role in beta cell growth and generation from extra-islet exocrine tissue inclusive of ducts, acinar cells and progenitor cells contained within these cells. Further, the present invention identifies the binding region within human Reg1a, human Reg1b, human Reg3a and human Reg4 and a binding domain on Reg Receptor, which are targets for the treatment of diabetes and other diseases for which there is need for new beta cells.

The present invention further demonstrates these peptides, which have not been described in the prior art, are unique Reg peptides for binding to the Reg Receptor on the surface pancreatic ductal tissue and are pivotal for new beta cell formation either via direct usage of the peptide, derivatives, optimized versions, peptidomimetics that bind to Reg Receptor or via stimulating antibodies generated from unique binding sites within the Reg Receptor that generate new beta cells.

This invention finds the Reg Receptor to be a pivotal receptor and a specific site within the Reg Receptor to be the site of Reg binding resulting in the translocation of the Reg Receptor through the cytoplasm to the nucleus of extra-islet exocrine tissue inclusive of ducts, acinar cells and progenitor cells contained within these cells, generating beta cell growth, acceleration and turnover.

BRIEF SUMMARY OF THE INVENTION

Embodiments of the present invention provide for novel agents and methods for pancreatic beta cell regeneration agents that have not previously been described. Agents include homologous human peptide sequences within the Reg1a, Reg1b, Reg3a and human Reg4 protein, as well as, stimulatory antibodies generated from a unique 20-amino acid binding region within the 919-amino acid protein human Reg Receptor. This invention includes formulations, derivatives, optimized forms of human peptides described, and also include peptidomimetics and stimulatory antibodies serving as peptidomimetics that are designed for the usage in the treatment of type 1 and 2 diabetes, and other conditions of insulin deficiency, beta cell deficiency, insulin resistance and abnormal glucose metabolism.

This invention includes methods for direct delivery of agents specified in this invention for generation of new beta cells from progenitor cells within the pancreas and provided to patients via oral, intravenous and subcutaneous delivery with and without organ specific targeting and may include direct delivery to the pancreas and also includes ex-vivo transformation using the inventions herein into new beta cells from embryonic stem cells, human adult bone-marrow derived cells, induced pluripotent stem cells, mesenchymal stem cells, umbilical cord stem cells, or other stem cells and may include resident populations of endogenous stem cells that exist within the adult pancreas that are then administered to patients with new and existing type 1 and 2 diabetes, PreDiabetes and diseases of insulin deficiency, beta cell deficiency, insulin resistance and impaired glucose metabolism, with routes of delivery to include, but are not limited to oral, intravenous, subcutaneous delivery with and without organ specific targeting and may include direct administration to the pancreas or liver.

This invention includes methods for pancreatic beta cell generation and include both in vivo and ex-vivo beta cell generation and methods for treating new onset and previously existing type 1 and 2 diabetes, Latent Autoimmune Diabetes of Adulthood (LADA), those at risk for type 1 diabetes, including but not limited to those with positive autoimmune antibodies markers including who are Glutamic Acid Decarboxylase-65 antibody, those with PreDiabetes and diseases of hyperglycemia, glucose intolerance and beta cell impairment or deficiency, insulin resistance, associated conditions including, obesity, obesity prior to the development of diabetes, obesity in children leading to PreDiabetes, both type 1 and type 2 diabetes in childhood and adolescence and include, but are not limited to conditions such as polycystic ovarian syndrome, nonalcoholic steatohepatitis, hyperlipidemia and hypertriglyceridemia and other conditions related to the deficiency or lack of effective amounts of insulin.

In the first embodiment, the present invention provides for the discovery of specific regenerative bioactive peptide sequences within the human Reg1a protein that are referred to as embodiments of "Perle Peptides" including the discovery of the following bioactive sequence within human Reg1a and Reg1b, NVWIGLHDP (SEQ ID NO: 1), found within the 166-amino acid human Reg1a protein (SEQ ID NO: 2) and within human Reg1b (SEQ ID NO: 3) and SEQ. ID NO: 1 also has 100% homology to sequences found in seven other mammals (FIG. 17). The 8-amino acid peptide VWIGLHDP (SEQ ID NO: 4) sequence within the human Reg1a protein (SEQ ID NO: 2), Reg1a (SEQ ID NO: 3) and within the human Reg3a protein (SEQ ID NO: 5), are demonstrated in this invention to bind directly to the human 919-amino acid Reg receptor (SEQ ID NO: 6). Sequence ID NO. 4 was also demonstrated to have 100% homology to 12 mammals including chimpanzee, rat, but not the mouse (FIG. 18). This invention also identifies homologous peptide sequences within human Reg1a, Reg1b, Reg3a and Reg4, WIGLHDP (SEQ ID NO: 7); and WIGLH-DPT (SEQ ID NO: 8), and VWIGLHDPT (SEQ ID NO. 14), which are all contained within the human Reg3a (SEQ ID NO: 5). SEQ ID NO. 8 has 100% homology to 12 other mammals (FIG. 19) including chimpanzee, rat, mouse, sheep and cow. SEQ ID NO:7 has 100% homology to 14 mammals including chimpanzee, mouse and rat (FIG. 20).

In the second embodiment, this discovery includes a 20-amino acid specific binding site (SEQ ID NO: 9) within the 919-amino acid Reg Receptor from which a stimulatory antibody to the Reg Receptor have been generated from this 20-amino acid.

In a third embodiment, this discovery also includes "Optimized Perle Peptides" including Perle peptidomimetics which refers to variations of Perle Peptides wherein the peptide has been modified to increase the stability, solubility, including formulations that have increased protease resistance, reduced immunogenicity, Tmax and bioavailability compared to the native peptide and/or provide greater ease in administration. Optimized formulations include developed modifications rendering the peptide sequences less susceptible to protease cleavage in serum with those proteases that normally recognize free ends, thereby effectively increasing the Tmax and bioavailability of the peptides include, but are not limited to the 1) blocking with a c-terminal acetyl groups and an n-terminal amide groups, 2) derivatives thereof modified by adding a cysteine residue to the n-terminal, resulting in a compound which is capable of forming dimers in solution 3) modified by conventional and backbone cyclization to improve biological activity, increasing bioavailability and dosing efficacy. Such modifications render the sequence less susceptible to protease cleavage in serum with those proteases that normally recognize free ends, thereby effectively increasing the Tmax and bioavailability of the peptides. Peptides modified in this manner demonstrate increased efficacy thereby requiring decreased dosages when administered.

For purposes of this invention, stability refers to the peptide's resistance to degradation by in-serum proteases which target and degrade Perle Peptides, Optimized Perle Peptides and Perle peptidomimetics. Also, for purposes of this invention, bioavailability refers to the amount of peptide available for in vivo therapeutic use by the target cells, pathways and/or systemic mechanisms based on the Perle Peptides' ability to avoid degradation by proteases and other systemic pathways that degrade Perle Peptides and Optimized Perle Peptides that include blocking the peptide by the addition of an n-terminal amide group and a c-terminal acetyl group, pegylated, cyclization and other methods thereof.

In a fourth embodiment, generation of new pancreatic beta cells occurs from the administration of Perle Peptides and includes formulations, derivatives, optimized forms and also include peptidomimetics of the Perle Peptide, Optimized Perle Peptides and agents that bind to the human Reg Receptor and a specific binding region within the Reg Receptor are presented in this invention with the modality of delivery including, but is not limited to: oral, intravenous, subcutaneous with direct and indirect delivery to the pancreas and liver.

In fifth embodiment, this inventions provides new therapy and specific methods for generation of new beta cells for usage in treatment of type 1 diabetes and autoimmune diabetes including 1) new onset and previously existing type 1, Latent Autoimmune Diabetes of Adulthood (LADA), those at risk for type 1 diabetes who have autoimmune markers including those who are Glutamic Acid Decarboxylase-65 antibody positive via the usage of Perle Peptides, Optimized Perle Peptides, Perle Peptidomimetics and Stimulatory Antibodies to the Perle Peptide Receptor in combination with immune tolerance agents to prevent autoimmune destruction of the new beta cells formed from this invention.

To date, numerous immune tolerance agents have been used in patients with new onset type 1 diabetes, but none have been able to render patients insulin-free because the ability to generate new beta cells is extremely limited, even when the immune attack is blocked. At the time of diagnosis of type 1 diabetes, there is already a loss of more than 90% of the beta cells, so that despite adequate immune blockage to the remaining beta cells, exogenous insulin injections are required. Once beta cells are lost, malfunction ensues in the remainder of the cell types within the islet that contribute to glucose homeostasis, making it impossible to treat diabetes into the normal range, with exogenous insulin injections, alone.

The fifth embodiment includes specific methodology and timing for administration of Perle Peptides, Optimized Perle Peptides, Perle Peptidomimetics and Stimulatory Antibodies to the Perle Peptide Receptor in parallel with an immune tolerance agent beginning on the day of the immune nadir of the specific immune agent, which varies vastly between the different agents utilized in man for immune tolerance among patients with type 1 diabetes. Furthermore, this invention provides specific methods for monitoring and tapering exogenous insulin dosages as new beta cells are formed since there are numerous feedback mechanisms to prevent hypoglycemia that prevent beta cell regeneration as a patient approaches normal glucose levels as new beta cells are generated.

In this embodiment, an innovative therapy for accelerated generation of the ex-vivo generation of beta cells by methodology for administration of Perle Peptides and/or formulations, derivatives, optimized forms including peptidomimetics and stimulatory antibodies to the Reg Receptor that are formed ex-vivo using Perle formulations, derivatives, optimized forms including peptidomimetics and stimulating Reg Receptor antibodies for ex-vivo by the transformation of new pancreatic beta cells from pluripotent stem cells including embryonic cells, adult somatic stem cells, human adult bone-marrow derived stem cells, umbilical cord stems cells, mesenchymal stem cells, human amniotic membrane-derived mesenchymal cells, pluripotent cells, mammalian stem cells, mammalian stem cells and ectodermal stem cells that are induced by this invention into new beta cells that may be administered intravenously, subcutaneously, intra-arterial and delivery including delivery to the pancreas, liver or other appropriate targets to optimize efficacy.

For patients with new onset or existing type 1 diabetes and patients with Latent Autoimmune Diabetes of Adulthood, Perle Peptides and/or formulations, derivatives, optimized forms including peptidomimetics and stimulatory antibodies to the Reg Receptor or beta cells formed from the ex-vivo generation of beta cells from Perle Peptides and/or formulations, derivatives, optimized forms including peptidomimetics and stimulatory antibodies to the Reg Receptor with new beta cells generated by ex-vivo methodology and are given to said patients with new onset or existing diabetes or Latent Autoimmune Diabetes of Adulthood after one or more immune tolerance agents are given with new beta cells generated by Perle Peptides and/or formulations, derivatives, optimized forms including peptidomimetics and stimulatory antibodies to the Reg Receptor being delivered to a said patient, and beta cells specifically initiated on the day of the immune nadir resulting, which varies by the individual or combination of immune therapies depending on which agent is selected, which may include but is not limited to: Cyclosporine, Anti CD-3 antibodies including hOKT3γ1(Ala-Ala) and ChAglyCD3 that target the immune response and specifically block the T-lymphocytes that cause beta cell death in type 1 diabetes; Sirolimus (Rapamycin); Tacrolimus (FK506); Etanercept, Alefacept, Belatacept, a heat-shock protein 60 (Diapep277); a tuberculosis vaccine, Glutamic Acid Decarboxylase 65 (GAD65) vaccine; the BCG tuberculosis vaccine also known as *Bacillus* Calmette-Guërin or Bacille Calmette-Guërin/BCG Vaccine, Mycophenolate Mofetil alone or in combination with Daclizumab; the anti-CD20 agent, Rituximab; Campath-1H (Anti-CD52 Antibody), lysofylline; anti-thymocyte globulin (ATG), Proleukin and those the combination of Proleukin and Rapamune, Vitamin D (Vitamin D2, D3, 1.25 dihydroxy D and other Vitamin D preparations), IBC-VSO vaccine, Ex vivo Expanded Human Autologous CD4+CD127lo/-CD25+ Polyclonal Regulatory T Cells; interferon-alpha; a vaccine using $CD4^+CD25^+$ antigen-specific regulatory T cells, Interleukin-1 Receptor Antagonist (anakinra), Alpha 1-Antitrypsin and other immunoprotective agents. New beta cells may be delivered to said patient via intravenously, subcutaneously, intra-arterial and delivery including delivery to the pancreas, liver or other appropriate targets to optimize efficacy.

In a sixth embodiment, this invention provides for the use of Perle Peptides, including formulations, derivatives, optimized forms including peptidomimetics and stimulatory antibodies to the Reg Receptor for the accelerated generation of beta cells are given directly to patients via oral, intravenous, subcutaneous and may include targeted therapy to the pancreas or liver and may also include the direct delivery of beta cells to patients formed by the ex-vivo transformation to pancreatic beta cells from pluripotent stem cells including embryonic cells, adult somatic stem cells, human adult bone-marrow derived stem cells, umbilical cord stems cells, mesenchymal stem cells, human amniotic membrane-derived mesenchymal cells, pluripotent cells, mammalian stem cells, mammalian stem cells and ectodermal stem cells that are induced by this invention into beta cells for the treatment of new onset and previously existing type 2 diabetes, those at risk with PreDiabetes and diseases of hyperglycemia, glucose intolerance and beta cell impairment or deficiency, insulin resistance, metabolic syndrome and associated conditions including, obesity, obesity prior to the development of diabetes, obesity in children leading to PreDiabetes, childhood diabetes, both and other conditions including but not limited to polycystic ovarian syndrome, nonalcoholic steatohepatitis, hyperlipidemia and hypertriglyceridemia and other conditions related to the deficiency or lack of effective amounts of insulin with the delivery of new beta cells by modalities including oral, intravenous, subcutaneous, intra-arterial and delivery including delivery to the pancreas, liver or other appropriate targets to optimize efficacy.

In a seventh embodiment of this invention includes the specific methods and treatment of new onset and previously existing type 2 diabetes, PreDiabetes, glucose intolerance, hyperglycemia, syndromes of insulin resistance and glucose impairment, diseases of hyperglycemia, glucose intolerance and beta cell impairment or deficiency, insulin resistance and associated conditions including: obesity, obesity prior to the development of diabetes, obesity in children leading to PreDiabetes, childhood diabetes (both type 1 and 2) and other conditions including but not limited to polycystic ovarian syndrome, nonalcoholic steatohepatitis, hyperlipidemia and hypertriglyceridemia and other conditions related to the deficiency or lack of effective amounts of insulin by the co-administration of Perle Peptide(s), including formulations, derivatives, optimized forms and peptidomimetics of the Perle Peptides that are administered alone or in conjunction of one or more diabetes agents, which may include all types of insulin, sulfonylureas, metformin, meglitinides, GLP-1 receptor analogs, DPP-4 inhibitors, thiazolidinediones, SGLT2 inhibitors, anti-inflammatory agents, pramlintide, Vitamin D and/or lifestyle modifications and other agents utilized to improve glucose in order to prevent and limit the destruction of the new beta cells formed by this invention.

The eighth embodiment of this invention includes the specific methods and treatment for tapering insulin and or diabetes medications patients as Perle Peptide(s), including formulations, derivatives, optimized forms and peptidomimetics of the Perle Peptides are administered in order to optimize efficacy. This includes providing specific methodology for optimizing the glycemic milieu before and during treatment with Perle Peptides and derivatives to optimize the formation of new beta cells.

The ninth embodiments of this invention include the specific methods and treatment for PreDiabetes, new onset and pre-existing type 2 diabetes utilizing Perle Peptide and includes formulations, derivatives, optimized forms and peptidomimetics of the Perle Peptide to accelerate the formation of new pancreatic beta cells that are administered to patients who diabetes-drug naïve.

In a tenth embodiment, the present invention provide pharmaceutical formulations and unit dose forms of Perle Peptides alone or in combination with one or more other active pharmaceutical ingredients (APIs). In one embodiment, the API is an agent in soluble liposome preparations that allow Perle Peptides to be administered by a variety of routes, including subcutaneously, intramuscularly, intravenously, intra-arterially, and even orally, depending on the formulation selected. In one embodiment, the formulation is for general systemic administration, but in other embodiments, the formulation comprises a targeting agent for targeted administration to specific locations, receptors, cells, tissues, organs, or organ systems including targeting to the liver and/or pancreas.

In an eleventh embodiment, methods are provided for treating a pathology associated specifically with impaired pancreatic function in a subject that may have diabetes or PreDiabetes, either type 1 or 2 and in need of such treatment. The method comprises one or more of the steps of (1) intensifying glycemic control (2) administering oral vitamin D to maintain 25-hydroxyvitamin levels above 40 mg/ml; (3) administering one or more immune therapies for protecting new islet cell formation, including administration of immunosuppressive agents; (4) administering Perle Peptide formulations, derivatives, optimized forms and peptidomimetics in combination with insulin or other diabetes agents, (5) reducing, or tapering off of other diabetes therapies as new beta cell populations are restored (6) administering repeat dosages of immunotherapy for the protection of beta cells formed by Perle Peptide formulations, derivatives, optimized forms and peptidomimetics on routine basis depending on the selected immune therapy and (7) administering Perle Peptide formulations, derivatives, optimized forms and peptidomimetics at intervals to maintain a minimum number of beta cells for normal glucose metabolism.

Embodiments of the invention also provide kits for treating a patient having type 1 or type 2 diabetes or other condition in which there are aberrant glucose and insulin levels, perturbation in glucose metabolism or insulin resistance, acute and comprising a therapeutically effective dose of Perle Peptides, Optimized Perle Peptides or Perle Peptide peptidomimetics and other Perle formulations. Further embodiments provide a kit for measuring Perle Peptides, Optimized Perle Peptides and Perle peptidomimetics levels in a sample, the kit comprising a Perle Peptides, Optimized Perle Peptides and Perle peptidomimetics-specific antibody and optionally Perle Peptides, Optimized Perle Peptides and Perle peptidomimetics and optionally a labeling means.

DESCRIPTION OF THE SEQUENCES

SEQ ID NO: 1 is an embodiment of a peptide of the present invention which is 9 amino acids in length. SEQ ID NO:1 is a partial sequence of human Regenerating islet-derived 1alpha (Reg1a).

SEQ ID NO: 2 is human Regenerating islet-derived 1alpha (Reg1a), also known as human lithostathine-1-alpha precursor (public accession number NP_002900)

SEQ ID NO: 3 is human Regenerating islet-derived 1beta (Reg1b), also known as lithostathine-1-beta precursor (public accession number NP_006498).

SEQ ID NO: 4 is an embodiment of a peptide of the present invention which is 8 amino acids in length. SEQ ID NO: 4 is a partial sequence of human Reg1a, human Reg1b, and human Reg3a.

SEQ ID NO: 5 is human regenerating islet-derived protein 3-alpha precursor (Reg3a) (public accession number NP_002571).

SEQ ID NO: 6 is the human Reg receptor, also known as exostosin-like 3 (public accession number NP_001431).

SEQ ID NO: 7 is an embodiment of a peptide of the present invention which is 7 amino acids in length. SEQ ID NO: 7 is a partial sequence of human Reg1a, human Reg1b, human Reg3a, and human Reg4.

SEQ ID NO: 8 is an embodiment of a peptide of the present invention which is 8 amino acids in length. SEQ ID NO: 8 is a partial sequence of human Reg3a.

SEQ ID NO: 9 is an embodiment of a binding site within the human Reg receptor for peptides of the present invention. SEQ ID NO: 9 is a partial sequence of the human Reg receptor.

SEQ ID NO:10 is human regenerating islet-derived protein 4 isoform 1 precursor (Reg4) (public accession number NP_114433).

SEQ ID NO:11 is a 14-amino Reg 3a peptide sequence (Human Proislet Peptide (HIP)) (SEQ ID NO: 3 of U.S. Pat. No. 7,393,919).

SEQ ID NO:12 is a 15-amino acid peptide within the hamster Reg3gamma peptide sequence (Islet Neogenesis Associated Protein (INGAP)) (amino acid residues 103 to 117 of SEQ ID NO: 2 of U.S. Pat. No. 5,834,590).

SEQ ID NO:13 is an N-terminal partial sequence of the human Reg receptor.

SEQ ID NO: 14 is a 9-amino acid peptide within Human Reg3a.

BRIEF DESCRIPTION OF THE DRAWINGS

FIG. 3 is a graphic depicting the 3-dimensional structures of human Reg1a, human Reg3a and Hamster Reg 3gamma by Swiss-Prot folding algorithms with the Perle Peptides contained within the Red circled binding arm.

FIG. 4 demonstrates to peptide homology between human Reg1a, Reg1a, Reg3a and Reg 4 and the Hamster Reg3gamma. The common sequences are highlighted in red.

FIG. 5 demonstrates the 8-amino acid human Reg sequence (SEQ ID: 8) that has 100% homology with Reg sequences found in the chimpanzee, cow, mouse and sheep, which has not been described in the prior art as a beta generation peptide.

FIG. 6 is the 919 amino acid sequence of the Reg Receptor with the 20-amino acid binding domain (SEQ ID: 9) presented in this invention highlighted in red.

FIG. 11 demonstrates the results of studies generating stimulatory antibodies to a 20-amino acid binding site within the Reg Receptor.

FIG. 12 provides the protocol for development of stimulatory antibodies to the binding domains within the Reg Receptor.

FIG. 17 demonstrates the 9-amino acid human Reg sequence (SEQ ID: 1) that has 100% homology with Reg sequences found in other mammals including chimpanzee, rat, golden hamster, white cheeked gibbon, Sumatran orangutan, Lowland gorilla, white-tufted-eared marmoset, which has not been described in the prior art as a beta generation peptide.

FIG. 18 demonstrates the 8-amino acid human Reg sequence (SEQ ID: 4) that has 100% homology with Reg sequences found in other mammals including chimpanzee, rat, golden hamster, guinea pig, rabbit, pig, sheep, cow, white-cheeked gibbon, Sumatran orangutan, Lowland gorilla, white-tufted-eared marmoset, which has not been described in the prior art as a beta generation peptide.

FIG. 19 demonstrates the 8-amino acid human Reg sequences (SEQ ID:8) that has 100% homology with Reg sequences found in other mammals including chimpanzee, rat, mouse, golden hamster, guinea pig, rabbit, pig, sheep, cow, white-cheeked gibbon, Sumatran orangutan, Lowland gorilla, European domestic ferret, which has not been described in the prior art as being beta regeneration peptide.

FIG. 20 demonstrates the 7-amino acid human Reg sequences (SEQ ID: 7) that has 100% homology with Reg sequences found in other mammals including chimpanzee, rat, mouse, golden hamster, guinea pig, rabbit, pig, sheep, cow, white-cheeked gibbon, Sumatran orangutan, Lowland gorilla, white-tufted-eared marmoset, European domestic ferret, which has not been described in the prior art as being beta regeneration peptide.

FIG. 21 demonstrates the 9-amino acid human Reg sequences (SEQ ID: 14) that has 100% homology with Reg sequences found in other mammals including chimpanzee, rat, mouse, golden hamster, guinea pig, rabbit, pig, sheep, cow, white-cheeked gibbon, Sumatran orangutan, Lowland gorilla, which has not been described in the prior art as being beta regeneration peptide.

FIG. 22 demonstrates the 20-amino acid human sequence that has been identified within the Reg receptor that has 100% homology with Reg receptor sequences found in other mammals including chimp, rat, mouse, guinea pig, rabbit, dog, cow, opossum, galago, gibbon, orangutan, macaque, gorilla, marmoset and horse.

DEFINITIONS

Figure 1:
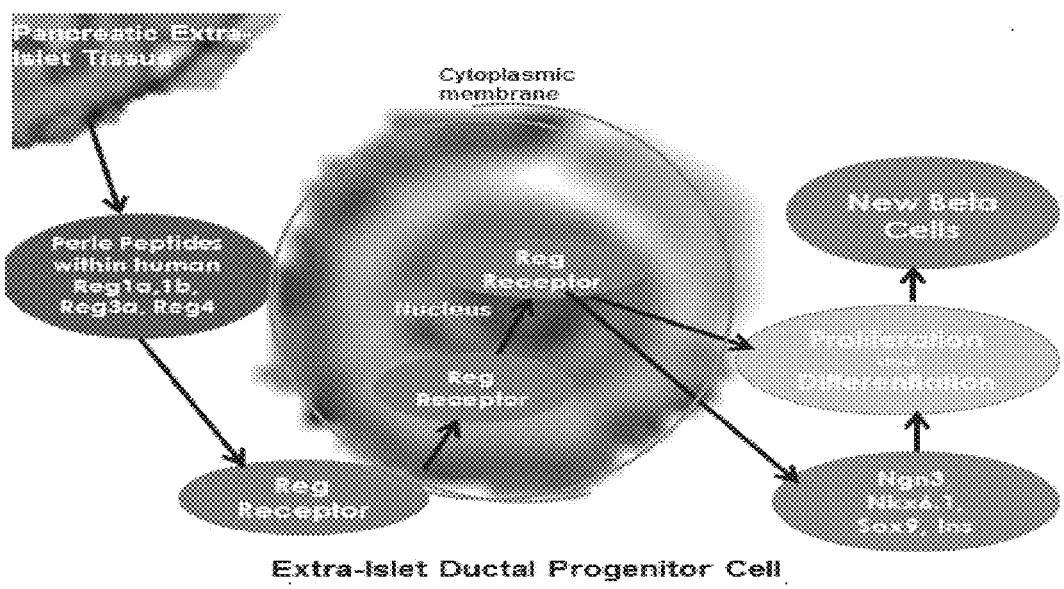
FIG. 1 is a graph depicting the schematic mechanism of action of the human Reg1a, Reg1b, Reg3a and Reg4 Perle peptides in the generation of new beta cells.

The following definitions are provided to assist the reader. Unless otherwise defined, all terms of art, notations and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not necessarily be construed to represent a substantial difference over the definition of the term as generally understood in the art.

As used herein, "treating" a condition or patient refers to taking steps to obtain beneficial or desired results, including clinical results. For purposes of this invention, beneficial or desired clinical results include, but are not limited to, alleviation or amelioration of one or more symptoms of diabetes, diminishment of extent of disease, delay or slowing of disease progression, amelioration, palliation or stabilization of the disease state, and other beneficial results described below. Symptoms of diabetes include low or inadequate levels of insulin or insulin activity, frequent urination, excessive thirst, extreme hunger, unusual weight loss, increased fatigue, irritability, blurry vision, genital itching, odd aches and pains, dry mouth, dry or itchy skin, impotence, vaginal yeast infections, poor healing of cuts and scrapes, excessive or unusual infections, hyperglycemia, loss of glycemic control, fluctuations in postprandial blood glucose, fluctuations in blood glucagon, fluctuations in blood triglycerides. Diabetes may be diagnosed by methods well known to one of ordinary skill in the art. For example, commonly, diabetics have a plasma blood glucose result of greater than 126 mg/dL of glucose. Pre diabetes, which may also be treated by the compositions and methods of the invention is commonly diagnosed in patients with a blood glucose result between 100 and 125 mg/dL of glucose. Other symptoms may also be used to diagnose diabetes, related diseases and conditions, and diseases and conditions affected by diminished pancreatic function.

As used herein, "reduction" of a symptom or symptoms (and grammatical equivalents of this phrase) means decreasing of the severity or frequency of the symptom(s), or elimination of the symptom(s).

As used herein, "impaired glucose homeostasis" is a diminished capacity in a subject for regulating glucose by a system of feedback controls, so as to stabilize health and functioning. Conditions that are associated with or are a risk factor for impaired glucose homeostasis include new onset type 1 and 2 diabetes, previously existing type 1 and 2 diabetes, latent autoimmune diabetes of adulthood (LADA), glutamic acid decarboxylase-65 autoimmunity, prediabetes, metabolic syndrome, hyperglycemia, glucose intolerance, beta cell impairment or deficiency, insulin resistance, obesity, polycystic ovarian syndrome, nonalcoholic steatohepatitis, hyperlipidemia, and hypertriglyceridemia As used herein, "administering" or "administration of" a drug to a subject (and grammatical equivalents of this phrase) includes both direct administration, including self-administration, and indirect administration, including the act of prescribing a drug. For example, as used herein, a physician who instructs a patient to self-administer a drug and/or provides a patient with a prescription for a drug is administering the drug to the patient.

As used herein, a "subject" or "patient" is a mammal, typically a human, but optionally a mammalian animal of veterinary importance, including but not limited to horses, cattle, sheep, dogs, and cats.

As used herein, a "therapeutically effective amount" of a drug or agent is an amount of a drug or agent that, when administered to a subject with a disease or condition, will have the intended therapeutic effect, e.g., alleviation, amelioration, palliation or elimination of one or more manifestations of the disease or condition in the subject. The full therapeutic effect does not necessarily occur by administration of one dose and may occur only after administration of a series of doses. Thus, a therapeutically effective amount may be administered in one or more administrations.

As used herein, a "therapeutically effective amount" of a drug may also be an amount of a drug that when administered to a subject, will have the intended prophylactic effect, e.g., preventing or delaying the onset (or reoccurrence) of disease or symptoms, or reducing the likelihood of the onset (or reoccurrence) of disease or symptoms. The full prophylactic effect does not necessarily occur by administration of one dose and may occur only after administration of a series of doses. Thus, a therapeutically effective amount may be administered in one or more administrations.

"Reg" is Regenerating islet-derived (as in Regenerating islet-derived protein).

"Perle Peptides" are specific regenerative bioactive peptide sequences contained within Regenerating islet-derived proteins.

DETAILED DESCRIPTION OF THE INVENTION

The pancreatic islets containing beta cells, which secrete insulin, were discovered in 1869 by a medical student, Paul Langerhans. Pancreatic islets, which are predominately comprised of beta cells are highly active metabolically, utilizing 20% of the blood supply delivered to the pancreas, but only accounting for 2% of the pancreatic mass; the remainder being extra-islet exocrine tissue containing ductal, acinar and progenitor tissue. This invention utilizes the extra-islet exocrine tissue to generate new beta cells.

Type 1 and type 2 diabetes have long been considered diseases resulting from diminished insulin secretion. Research carried out over the past century has more clearly found that generating new beta cells that make insulin, is the key to reversing this disease. At the onset of type 2 diabetes, there is a 50%-80% reduction in beta cell mass compared to the more acute 90% loss found in newly diagnosed type 1 diabetic patients. Although the beta cell mass may expand several fold from birth to adulthood, this is not enough to compensate for the greater loss than generation of new beta cells seen in both type 1 and 2 diabetes.

After reading an article by Moses Barron on the impact of pancreatic stones on exocrine cell atrophy and beta cell proliferation, a surgeon, Frederick Banting, discovered insulin based on his hypothesis on Oct. 31, 1920, that clamping of the pancreatic ducts could lead to a treatment for diabetes, which it did. Banting's secretions became known as insulin.

Similar work to that of Barron and Banting led surgeons to clamp the pancreatic ducts of severely ill diabetic children during the early 1900s in the hopes of expanding the production of humeral substances leading to new beta cells. Benefits from these novel procedures were described but were short-lived, perhaps because of ongoing autoimmune destruction.

The concept that ductal ligation might induce islet formation was novel to Banting. Yet, three decades prior to Banting's work, the French histologist, Edouard Laguesse described the islet population as being formed primarily during embryogenesis. Laguesse described the ability of the islet to grow postnatally through a process of metamorphosis from the surrounding ductal tissue. Ductal tissue as a source for formation of new beta cells remains a leading hypothesis.

Not until 1999, when the use of cell lineage labeling became available, did the embryological concepts of the pancreas change. Whereas it had been thought that the pancreas was derived from both ectoderm and endoderm, it has now been shown that the entire pancreas arises only from endoderm during embryological development. This helps explain how beta progenitor cells have been described as residing diffusely throughout the adult pancreatic tissue. Many teams have confirmed that new beta cells can be derived from pancreatic extra-islet exocrine tissue containing ductal, acinar and progenitor cells.

Over the past several decades, the regenerating gene (Reg or REG) family has emerged among many species, including humans, as a potential key initiating factor in the process of islet neogenesis. The Reg genes are associated with islet neogenesis and are upregulated in the pancreas during embryogenesis when the pancreas is being populated with beta cells for the first time.

After fetal development, the Reg genes are usually undetectable, but are upregulated in response to acute pancreatic injury including pancreatic stones, pancreatitis, pancreatic duct ligation and wrapping, partial pancreatectomy and pregnancy. The Reg gene proteins are a family of C-type lectin proteins that are expressed almost exclusively by the pancreas.

The 15-amino acid hamster Reg 3gamma gene protein (INGAP) and the 14-amino acid Reg3a peptide (HIP) have both been shown to stimulate new beta cell formation from extra-islet exocrine progenitors, as well as upregulating growth promoting factors associated with new beta cells including NGN3, PDX-1, NKx6.1, Ins, Sox9 and others.

This invention identifies key human Reg peptide sequences that are not contained within either 15-amino acid hamster Reg 3gamma gene protein (INGAP) or the human 14-amino acid Reg3a peptide, Human Proislet Peptide (HIP), that bind directly to the Reg receptor and stimulate downstream activity resulting in translocation of the Reg Receptor from the cytoplasmic membrane to the nucleus stimulating new beta cell formation. Additionally this invention identifies a specific binding region within the 919-amino acid Reg Receptor from which stimulatory antibodies serving as peptidomimetics have been generated.

FIG. 1 is a schematic drawing showing the findings of the present invention demonstrating how the human Reg1a, Reg1b, Reg3a and Reg4 peptides bind to and interact with the Human Reg Receptor on pancreatic exocrine tissue and stimulate the translocation of the Reg Receptor from its position on the cell surface and accelerates the movement of the Reg Receptor from the cytoplasmic membrane through the cytoplasm to the nucleus with downstream activation leading to the generation of new pancreatic beta cells.

Figure 2:
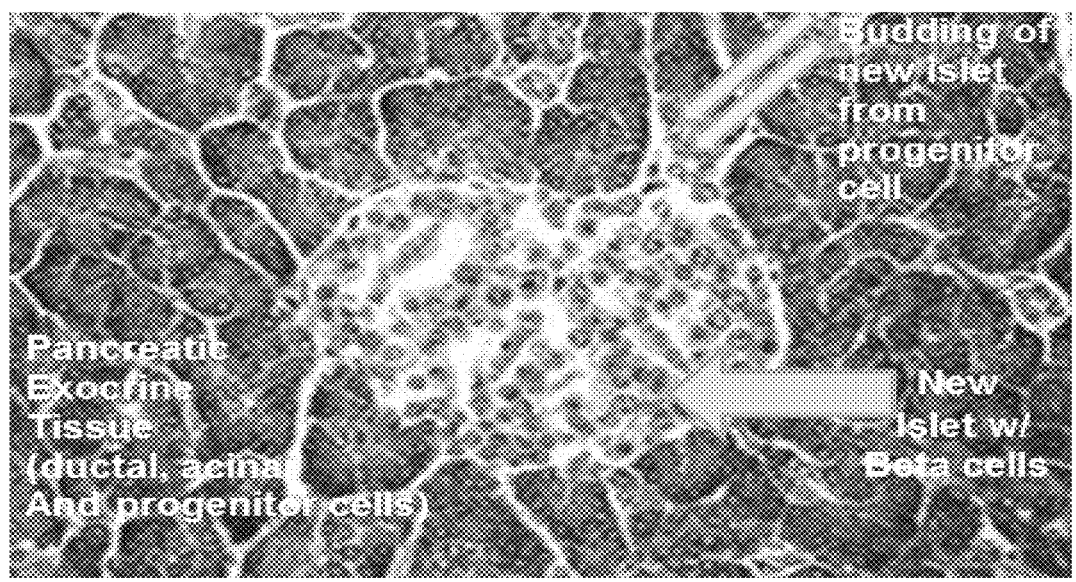
FIG. 2 is a photograph of a rodent islet containing beta cells that is budding from a progenitor cell found within the extra-islet exocrine tissue containing ductal, acinar and progenitor cells.

FIG. 2 is a photograph of a rodent islet that is formed from the budding from a progenitor cell within surrounding extra-islet ductal tissue containing ducts, acinar and progenitor cells. The first known description of new islet cells arising from pancreatic ductal cells comes from the French histologist, Edouard Laguesse, in 1893.

FIG. 3 is an illustration showing the similarities and differences between three dimensional structures of human Reg1a, Reg3a and the Hamster Reg3 gamma peptides based on their primary amino acid sequences and by Swiss-Prot folding algorithms. FIG. 3a shows the three dimensional structure for Human Reg 1a. FIG. 3b shows the three dimensional structure for Reg3a. FIG. 3c shows the three dimensional structure for the hamster Reg3gamma. The region of the protein that contain the Perle peptides, which bind to Reg Receptor, is circled in Red, The Perle peptides are not contained within the 14-amino acid previously described HIP peptide and the 15-amino acid hamster peptide INGAP.

FIG. 4 is an alignment of the 166 amino acid sequence for Reg1a (SEQ ID NO:2), the 166 amino acid sequence for Reg1b (SEQ ID NO: 3), the 175-amino acid sequence for Reg3a (SEQ ID NO: 5), the 158 amino acid sequence for Reg4 (SEQ ID NO:10) and the hamster Reg3gamma protein. A 14-amino Reg 3a peptide sequence (HIP) (SEQ ID NO: 11) and a 15-amino acid peptide within the hamster Reg3gamma peptide sequence INGAP (SEQ ID NO: 12) has been shown in the prior art to interact with the Reg receptor, resulting in downstream generation of new beta cells, but these sequences have not been demonstrated to directly bind to the Reg receptor, which is confirmed in this discovery. The 8 and 7-amino acid sequences that are presented within in this invention bind to the Reg receptor and are not contained within the 14-amino acid Reg3a peptide, HIP, or the hamster Reg3gamma peptide, INGAP.

FIG. 5 shows the identification of the 100% homologous sequence (SEQ ID: 8) within the human Reg 1a, Reg1b, Reg3a, Reg4 and the Hamster Reg3gamma peptides that is located within the binding arm of the protein that binds to the Reg Receptor. This exact sequence is also found in the human, chimpanzee, cow, sheep and mouse. This sequence (SEQ ID: 8) and amino-acids within the sequence are not contained within the 14-amino acid human Reg3a HIP peptide or the 15-amino acid hamster Reg3gamma peptide, INGAP.

FIG. 6 shows the 919-amino acid Reg Receptor (SEQ ID: 6) and the 20-amino acid domain (SEQ ID NO: 9) in red that was identified in this discovery that is a binding domain for the Perle Peptides, and from which stimulatory antibodies to this region of the receptor have been generated.

Figure 7:
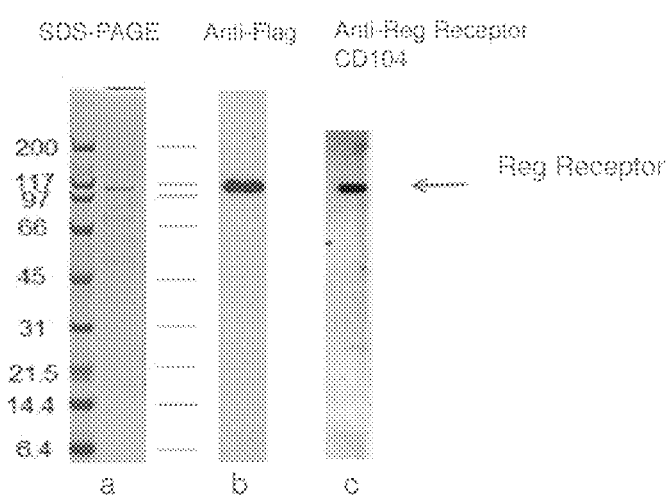
FIG. 7 demonstrates the purification and detection of the Reg Receptor for usage in this invention.

FIG. 7 demonstrates the results from studies conducted to demonstrate Reg Receptor expression and purification utilizing 293T cells that were transfected with Reg Receptor expression plasmid DNA. Cells were collected after 72 hours. The Reg Receptor was tagged with FLAG epitope and FLAG resin was utilized to purify out the Reg Receptor. As shown in FIG. 7, the Reg Receptor was highly purified. The Reg Receptor was purified by Anti-Flag M2 affinity gel. Target protein was confirmed by 4-12% SDS-PAGE and Western-blot. FIG. 7a demonstrates the use of sodium dodecyl sulfate polyacrylamide gel electrophoresis (SDS-PAGE) to illustrate the high purity of the Reg Receptor. FIGS. 7b and 7c are the Western blot results showing that the purified protein is the Reg Receptor using the antibody to the Reg Receptor (CD104). The Reg Receptor is shown In FIG. 7 to be highly purified.

To then demonstrate the direct binding of Perle Peptides to the Reg Receptor, the purified Reg receptor was coated onto 96 well plate by using bicarbonate coating buffer, pH 9.6; 4° C. overnight at concentration 3 ug/ml, 100 ul per well. Plates were coated overnight coated plate and washed three times with 0.5×TBST and blocked with 3% BSA and rotated at room temperature for 1 hour. After blocking, plates were washed three times with 0.5×TBST. Peptides were then diluted with TBST buffer and added into wells in duplicate then left to bind at room temperature for 1 hour. After washing three times, 100 ng/ml strep-HRP was added into plate at 100 ul/well, and rotated at room temperature for one hour. ABST reagents were warmed to room temperature, mixed immediately before using. Then 100 ul was added to each well and read after 25 minutes reaction and absorbance was evaluated at 405 nm by a Spectramax M5 plate reader. The purified Reg Receptor was coated on plates. Then plates were blocked with BSA solution. Subsequently, the Perle peptides were added into the wells, and HRP-streptavidin and its substrates were added into the wells to reveal the interaction between Receptor and the Perle peptide.

Figure 9:
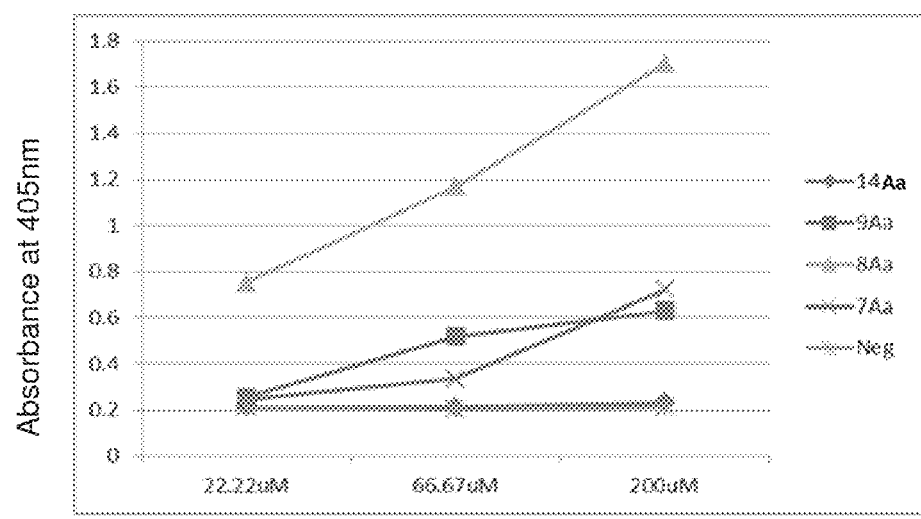
FIG. 9 demonstrates the direct binding of the Perle peptides to the Reg Receptor. The 14-amino acid human Reg3a peptide (HIP) demonstrated no direct binding to the Reg Receptor, nor did the scrambled peptide control. The 8 amino-acid Perle peptide demonstrated the greatest binding to the Reg Receptor

As shown in FIG. 9, the 7-amino acid Perle peptide, the 8-amino acid Perle peptide and the 9-amino acid Perle peptide all bind directly to Reg Receptor. The 8-amino acid peptide appeared to be the strongest in binding to the Reg Receptor. The scrambled control peptide did not bind to Reg Receptor. The 14-amino acid human Reg3a peptide (HIP), has demonstrated the ability to generate new beta cells through the interaction with the Reg Receptor, but has not been shown to directly bind to the Reg Receptor. The 14-amino acid human Reg3a peptide (HIP), was shown in this study to have the same level of binding as the scrambled peptide FIG. 9. The 7, 8 and 9-amino acid Perle Peptides sequences are not contained within the 14-amino human Reg3a peptide (HIP) sequence or the 15-amino acid hamster 3gamma peptide (INGAP).

Figure 8:
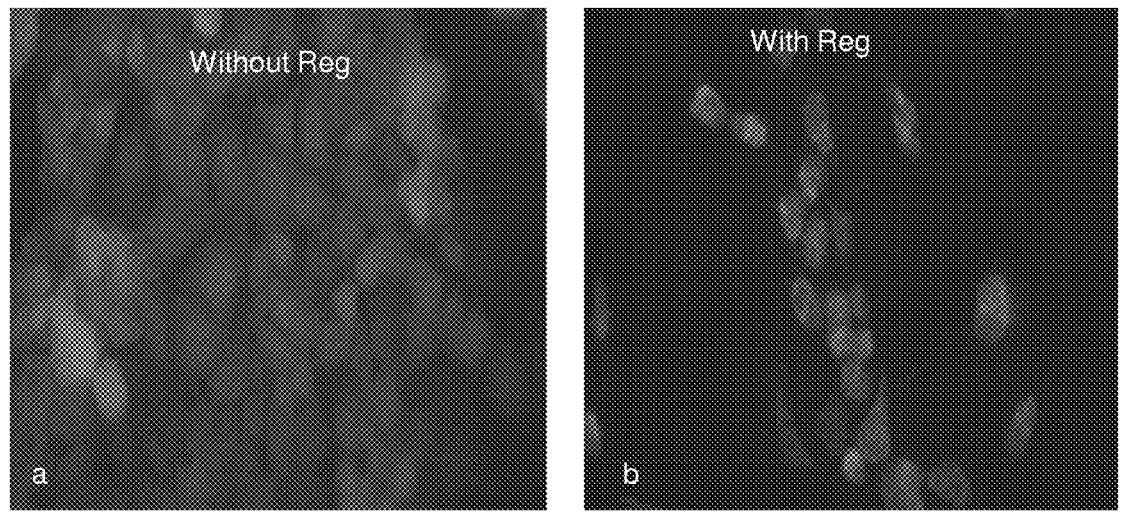
FIG. 8 demonstrates the labeling of the Reg Receptor on the cell surface (FIG. 8*a*) with internalization of the Reg Receptor inside the cell in the presence of Reg (FIG. 8*b*).

FIG. 8 shows immunofluorescent staining of Reg receptor on the cell surface of human pancreatic exocrine ductal cells. In utilizing Cy3 immunofluorescent staining of Reg receptor in human pancreatic ductal cells in standard medium, there is immunofluorescent staining of Reg receptor, which is well-defined at the cell borders indicating surface expression of Reg receptor on the cytoplasmic membrane of cells (FIG. 8a). FIG. 8b demonstrates the difference in Reg receptor staining when cells are exposed to Reg.

Figure 10:
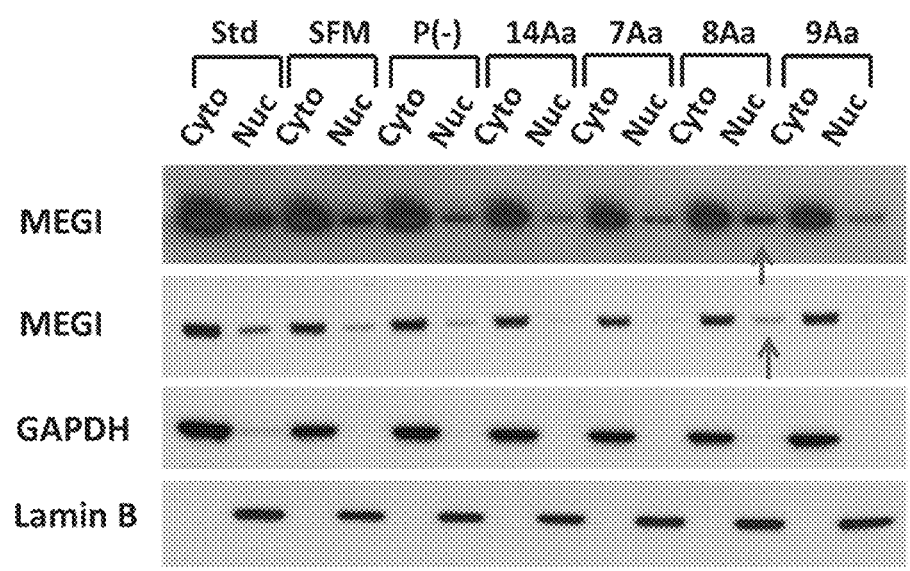
FIG. 10 is confirmation of nuclear translocation of the Reg Receptor from the cytoplasmic nucleus with the 8-amino acid peptide.

FIG. 10 demonstrates a confirmation study utilizing Western blot analysis to evaluate the translocation of the Reg Receptor from the cytoplasmic membrane of human extra-islet exocrine tissue inclusive of ductal cells containing progenitor. Western blot analysis identified the presence of the Reg receptor on the cytoplasmic membrane and the movement of the Reg Receptor from the cytoplasmic membrane through the cytoplasm to the nucleus in the presence of the Perle peptides. Cytoplasmic extracts were obtained in 10 mM HEPES (pH 8.0), 1 mM EDTA, 1.5 mM $MgCl_2$, 10 mM KCl, 0.5 mM DTT, 200 mM sucrose and 0.5% Nonidet P-40. Nuclear extracts were obtained in 20 mM HEPES (pH 7.9), 0.75 mM $MgCl_2$, 210 mM NaCl, 50 mM KCl, 1 mM EDTA, 10% glycerol, and 0.5 mM DTT. Both extraction buffers contained 0.5 mM PMSF, 1 μg/ml leupeptin, 1 μg/ml aprotinin, 2.5 mM $Na_4P_2O_7$, 1 mM β-glycerophosphate, and 1 mM $Na_3VO_4$. Reg Receptor extracts were size fractionated on SDS-polyacrylamide gels and transferred to nitrocellulose. After blocking in 3% milk in Tris-buffered saline (pH 7.4), blots were sequentially incubated with rabbit anti-human Reg Receptor antibody overnight at 4° C. and appropriate horseradish peroxidase-conjugated secondary antibody. Secondary signals were developed with chemiluminescence substrate and analyzed by autoradiography.

Fractions and quality control utilized the fractions with two antibodies, GAPDH as a cytosol molecule and Lamin B is a nuclear molecule. Both GADPH and Lamin B were demonstrated in this invention to serve as excellent controls for the nuclear and cytosolic fractions (FIG. 10). Evaluation was conducted to determine the impact and interaction of the Reg Receptor with the Perle Peptides and the 14-amino acid HIP peptide.

This invention demonstrates in FIG. 10 that the 8-amino-acid Perle Peptide resulted in the greatest impact on translocation of the Reg Receptor from the cytoplasm to the nucleus both in the shorter and longer exposure times. The impact of the 8-amino acid Perle Peptide was greater than the other peptides tested including the 14-amino acid HIP peptide.

Figure 13:
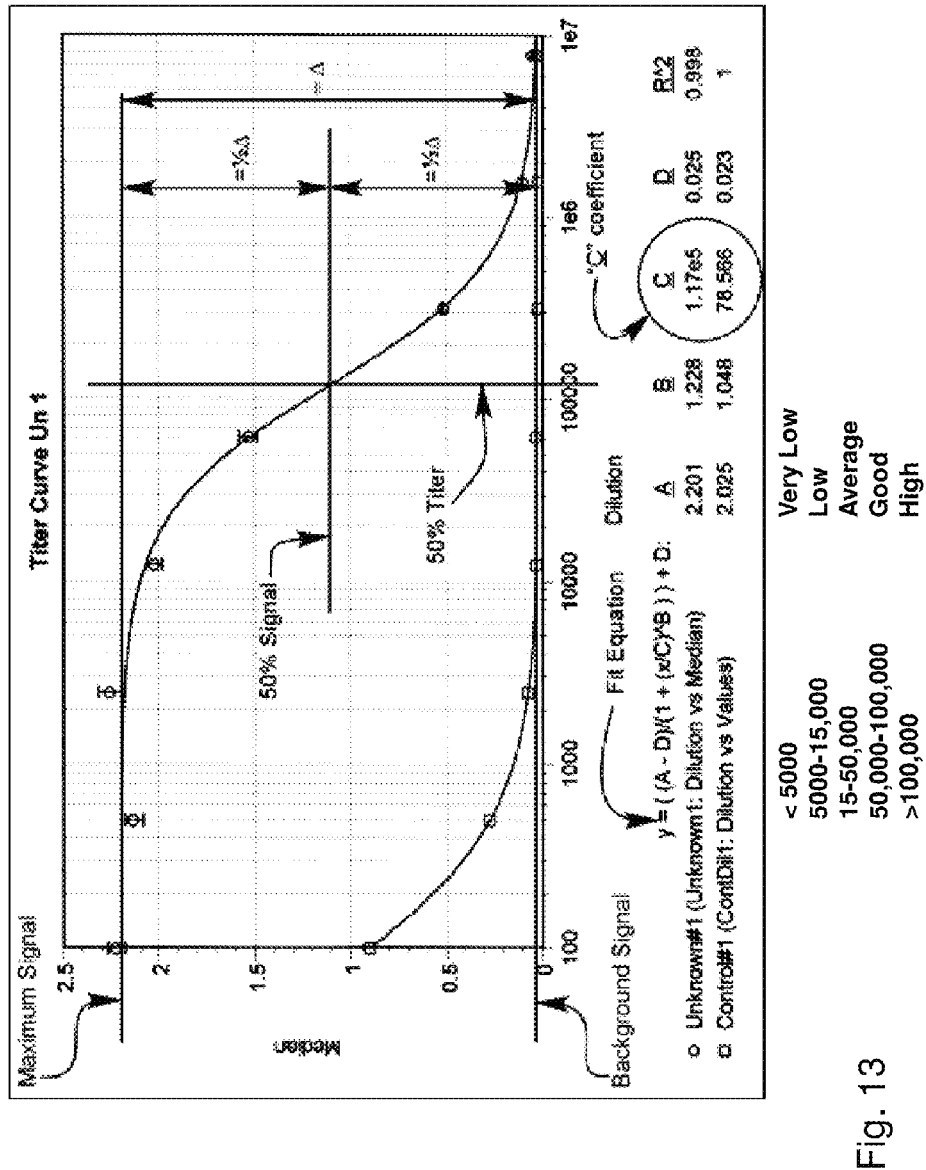
FIG. 13 is the documentation of titer controls and norms for the antibody studies.

FIGS. 11-13 were from studies undertaken to develop stimulatory antibodies to the Reg Receptor to accelerate the progression of beta cell formation by stimulating potential binding sites on the Reg Receptor. For the production of inhibitory antibodies, many sequences were evaluated within the N-terminal portion of Reg receptor (amino acids 1-332) (SEQ ID NO:13), which is the amino acid region believed to be the binding domain for the Reg peptides within the Reg receptor that is not contained in the other members of the of Exostoses family, and thus is hypothesized to be the Reg binding domain.

Consistently, in Enzyme ImmunoAssay studies measuring titers from peptide sequences within SEQ ID NO:13, resulted in very high polyclonal antibodies being raised to a 20-amino acid Reg receptor sequence (SEQ ID NO:9) (amino acids 117-136). The results of the Enzyme ImmunoAssay are summarized in FIG. 12. FIG. 13 demonstrates the standard protocol used for development of polyclonal antibodies to peptide regions within Reg receptor.

Data sets were taken from the bleed after the day 0 and day 21 boosts. The animals were injected with a peptide of SEQ ID NO: 9 and were conjugated to keyhole limpet hemocyanin (KLH). The screening antigen is not conjugated to KLH so that the response solely to the peptide and not to KLH can be identified. The 50% titer is a dilution value where the signal is half-way between the peak and the baseline, so the higher the dilution value (titer), the greater the response to the antigen. The positive control is an internal control that was generated from ovalbumin antibodies in rabbit. At a dilution of 1:750,000, the absorbance fell within a range of 0.45 to 0.9. In the case of the response to SEQ ID NO: 9, there was a high response (FIG. 11). The test bleed taken 31 days after the day 0 and 21 day boosts for CD 153 showed a 50% titer of 36,000 which is an average response, and CD 154 showed a 50% titer of 125,000 which is a high response according to the polyclonal titer reference range shown in FIG. 13. Studies are underway to evaluate the efficacy of the antibody generated with and without the presence of Reg peptide demonstrating that the antibodies are stimulatory to the Reg peptide interaction with Reg receptor to generate beta cells in human extra-islet exocrine tissue including progenitor cells.

Figure 14:
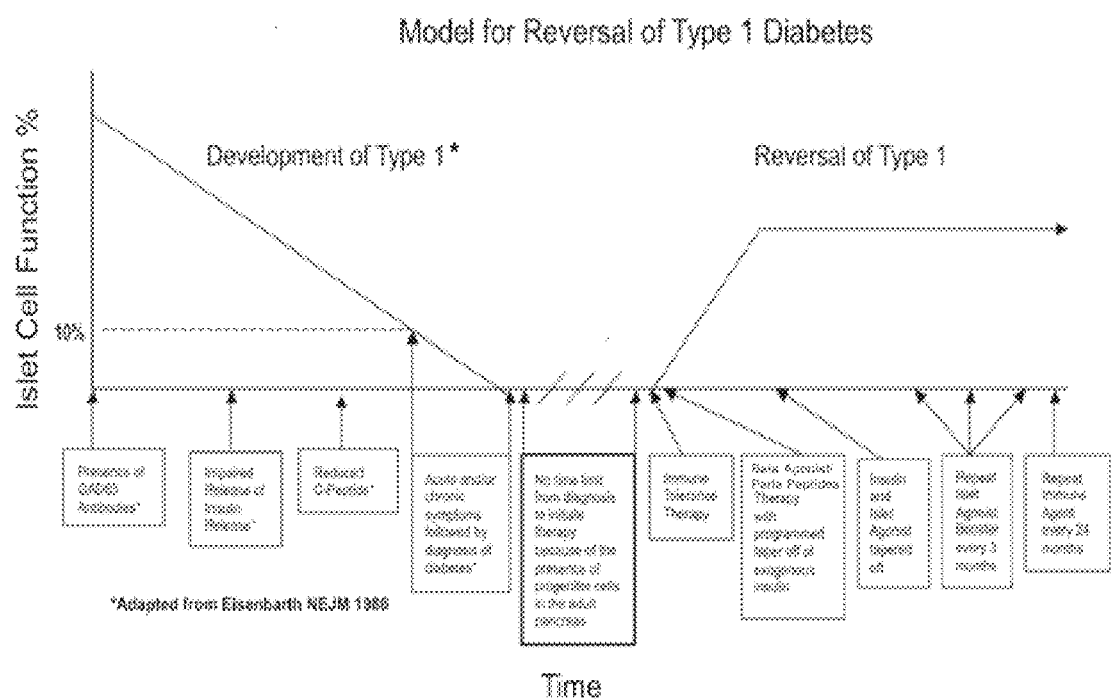
FIG. 14 is an illustration of the methodology to reverse new onset or existing type 1 diabetes utilizing Perle peptides, formulations, derivatives, and optimized forms including peptidomimetics of the peptides and stimulating antibodies to the Reg receptor.

FIG. 14 illustrates present invention provides an illustration of the method for treating newly diagnosed or pre-existing type 1 diabetes mellitus in a patient, by a method comprising administering to said patient of an agent that stimulates beta cell regeneration, which includes Perle peptides, derivatives, optimized versions, peptidomimetics or stimulatory antibodies to the Reg Receptor Perle peptides, in combination with an immune tolerance agent or combination of immune tolerance agents. An agent that stimulates beta cell regeneration includes, but is not limited to Perle peptides, derivatives, optimized versions, peptidomimetics or stimulatory antibodies to the Reg Receptor. Immune tolerance agents may include, but are not limited to, Cyclosporine, the heat shock protein 60, Diapep 277, the *Bacillus* Calmette-Guërin or Bacille Calmette-Guërin also known as the BCG vaccine and commonly known as the vaccine against tuberculosis, mycophenolate mofetil, daclizumab, rituximab (anti CD20), anti CD3 antibodies including hOKT3 gamma1 (Ala-Ala), and the monoclonal antibody TRX4 (ChAglyCD3), CTLA4-Ig (abatacept) a selective co-stimulation modulator as it inhibits the co-stimulation of T cells, campath-1H, anti-CD52 antibody, a or humanized monoclonal antibody to T-cells, polyclonal anti-T-lymphocyte globulin (ATG), DiaPep277, GAD antibody vaccine based on the 65 kDa isoform of the recombinant human glutamic acid decarboxylase protein (rhGAD65), and diazoxide, Alpha-1 Antitrypsin in combination with Vitamin D or a derivative thereof, including, but not limited to cholecalciferol and 1,25 dihydroxyvitamin D.

This invention provides for specific methodology for administration of Perle peptides, derivatives, optimized versions, peptidomimetics or stimulatory antibodies to the Reg Receptor for generation of beta cells in newly diagnosed type 1 patients and in those with existing type 1 diabetes and those with Latent Autoimmune Diabetes of Adulthood. Methods provide for initiation of Perle peptides, derivatives, optimized versions, peptidomimetics or stimulatory antibodies to the Reg Receptor on the day of the immune nadir occurring at a different time with each of the above immune agents. Based on this specific timing, which varies with each agent, there is greater ability to protect new beta cells generated by Perle peptides, derivatives, optimized versions, peptidomimetics or stimulatory antibodies to the Reg Receptor.

Figure 15:
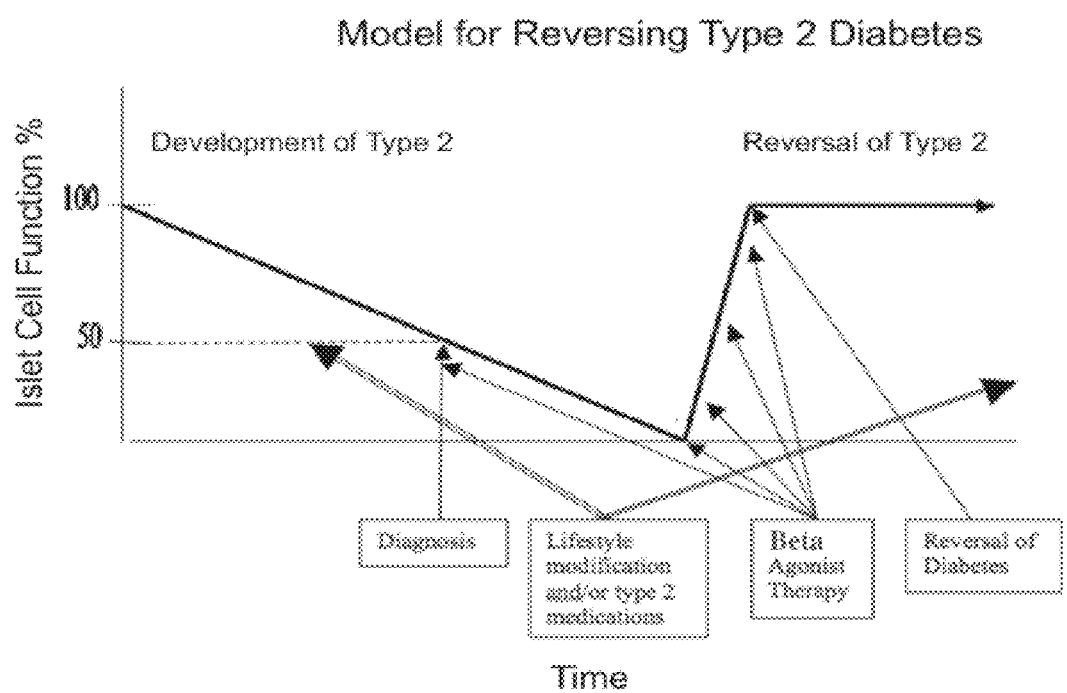
FIG. 15 is an illustration of the methodology to reverse type 2 diabetes utilizing beta agonist therapies including Perle peptides, formulations, and derivatives, optimized forms including peptidomimetics of the peptides and stimulating antibodies to the Reg receptor.

FIG. 15 illustrates the methodology for reversal of type 2 diabetes and preventing the progression of PreDiabetes to Diabetes utilizing a beta cell agonist such as Perle peptides, derivatives, optimized versions, peptidomimetics or stimulatory antibodies to the Reg Receptor. Perle peptides, formulations, optimized versions, peptidomimetics and stimulating antibodies to a binding region on the Reg receptor identified in this invention would be first-line therapy for patients with type 2 diabetes and PreDiabetes or added to existing diabetes medications regimens including insulin. Based upon glucose levels, other diabetes medications, including insulin could be tapered.

Many patients with diabetes and PreDiabetes are currently on one or more agents, which may include a combination of agents which may improve existing beta cell function and glucose metabolism. Perle peptides, formulations, optimized versions, peptidomimetics and stimulating antibodies to a binding region on the Reg receptor will be used as first-line therapy for new onset and existing type 2 diabetes, as well as PreDiabetes. Perle peptides, formulations, optimized versions, peptidomimetics and stimulating antibodies to a binding region on the Reg receptor may be added to other diabetes agents and including: all types of insulin, Glucagon Like Peptide-1 (GLP-1) receptor analogs Liraglutide and Exenatide, Dipeptidyl Peptidase-4 Inhibitors, (DPP-4 inhibitors), and including (Sitagliptin, Saxagliptin, Linagliptin), the Amylin, analog, pramlintide, acarbose, orlistat, colesevelam, bromocriptine, orlistat, combination therapies with the biguanide, metformin, and combinations of with thiazolidinediones, sulfonylureas and DPP-4 inhibitors and new agents SGLT2 inhibitors (dapagliflozin and canagliflozin). The ability to provide patients with type 2 diabetes with new beta cells may enable tapering of other medications and also prevent the progression of PreDiabetes to type 2 diabetes.

Figure 16:
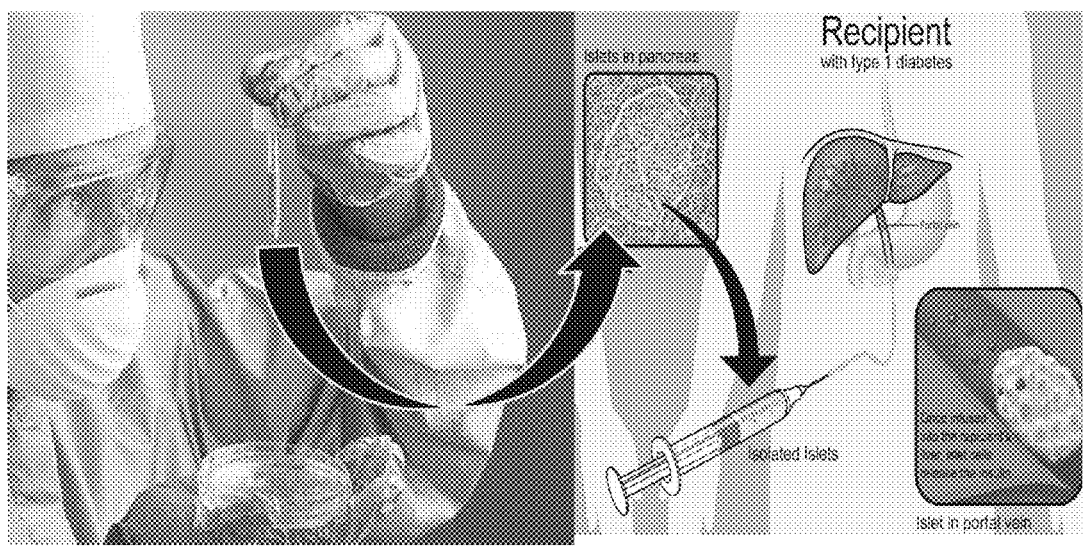
FIG. 16 demonstrates the ex-vivo generation of beta cells using Perle peptides, formulations, derivatives, optimized forms including peptidomimetics of the peptides and stimulating antibodies to the Reg receptor to transform human extra-islet tissue including ductal, acinar and progenitor cells, human embryonic stem cells, human adult bone-marrow derived cells, induced pluripotent stem cells, mesenchymal stem cells, umbilical cord stem cells, or other stem cells and may include resident populations of endogenous stem cells that exist within the adult pancreas that are transformed into new beta cells then delivered to patients with diabetes and other conditions of insulin deficiency via the umbilical vein, portal venous systemic, hepatic artery, subcutaneous delivery.

FIG. 16 includes methods for the formation and delivery of new beta cells generated by Perle peptides, derivatives, optimized versions, peptidomimetics and antibodies generated to specific binding regions of the Perle Receptor serving as peptidomimetics when utilized for the ex-vivo generation of new beta cells from progenitor cells, which may include, but are not limited to human extra-islet tissue inclusive of ductal, acinar and progenitor embryonic tissue, human stem cells, human adult bone-marrow derived cells, induced pluripotent stem cells, mesenchymal stem cells, umbilical cord stem cells, or other stem cells and may include resident populations of endogenous stem cells that exist within the adult pancreas that are facilitated to transform into beta cells by the addition of Perle peptides, derivatives, optimized versions, peptidomimetics and antibodies generated to specific binding regions of the Perle Receptor serving as peptidomimetics. New beta cells are generated ex-vivo transformation using the inventions herein into new beta cells from Perle peptides, derivatives, optimized versions, peptidomimetics and antibodies generated to specific binding regions of the Perle Receptor serving as peptidomimetics. New beta cells are then delivered to patients with PreDiabetes, type 1 and 2 diabetes and other conditions of beta cell deficiency with routes of delivery to include, but are not limited to oral, intravenous, including delivery via the umbilical vein, portal venous systemic, hepatic aortic artery, subcutaneous delivery with and without organ specific targeting and may include direct administration to the pancreas or liver (FIG. 16).

Perle peptides, derivatives, optimized versions, peptidomimetics and antibodies generated to specific binding regions of the Perle Receptor serving as peptidomimetics are then administered ex-vivo to human extra-islet tissue, inclusive of ductal, acinar and progenitor tissue, embryonic stem cells, human adult bone-marrow derived cells, induced pluripotent stem cells, mesenchymal stem cells, umbilical cord stem cells, or other stem cells and may include resident populations of endogenous stem cells that exist within the adult pancreas to form new beta cells. The new beta cells are generated by the delivery of Perle peptides, derivatives, optimized versions, peptidomimetics and antibodies generated to specific binding regions of the Perle Receptor to ex-vivo cultures of human embryonic stem cells, human adult bone-marrow derived cells, induced pluripotent stem cells, mesenchymal stem cells, umbilical cord stem cells, or other stem cells and may include resident populations of endogenous stem cells that exist within the adult pancreas, accelerate the formation of new beta cells. These beta cells are then delivered to patients with PreDiabetes, type 1 and 2 diabetes and other conditions of beta cell deficiency with routes of delivery to include, but are not limited to oral, intravenous, including delivery via the umbilical vein, portal venous systemic, hepatic aortic artery, subcutaneous delivery with and without organ specific targeting and may include direct administration to the pancreas or liver.

This invention includes methods for pancreatic beta cell generation and include both in vivo and ex-vivo beta cell generation and methods for treating new onset and previously existing type 1 and 2 diabetes, Latent Autoimmune Diabetes of Adulthood (LADA), those at risk for type 1 diabetes, including but not limited to those with positive autoimmune antibodies markers including who are Glutamic Acid Decarboxylase-65 antibody, those with PreDiabetes and diseases of hyperglycemia, glucose intolerance and beta cell impairment or deficiency, insulin resistance, associated conditions including, obesity, obesity prior to the development of diabetes, obesity in children leading to PreDiabetes, both type 1 and type 2 diabetes in childhood and adolescence and include, but are not limited to conditions such as polycystic ovarian syndrome, nonalcoholic steatohepatitis, hyperlipidemia and hypertriglyceridemia and other conditions related to the deficiency or lack of effective amounts of insulin.

FIG. 17 shows the identification of the Perle Peptide 9-amino acid human Reg sequence (SEQ ID: 1) that has 100% homology with sequences found in other mammals including chimpanzee, rat, mouse, golden hamster, guinea pig, rabbit, pig, sheep, cow, white-cheeked gibbon, Sumatran orangutan, Lowland gorilla, white-tufted-eared marmoset, European domestic ferret which has not been described in the prior art as being beta regeneration peptide. This invention evaluated GenBank, Basic Local Alignment Search Tool (BLAST) algorithm and UniProtKB which produced by the UniProt Consortium which consists of groups from the European Bioinformatics Institute (EBI), the Swiss Institute of Bioinformatics (SIB) and the Protein Information Resource (PIR). This sequences (SEQ ID: 1) and amino-acids within the sequence are not contained within the 14-amino acid human Reg3a HIP peptide or the 15-amino acid hamster Reg3gamma peptide, INGAP.

FIG. 18 shows the identification of the Perle Peptide 8-amino acid human Reg sequence (SEQ ID: 4) that has 100% homology with sequences found in other mammals including chimpanzee, rat, mouse, golden hamster, guinea pig, rabbit, pig, sheep, cow, white-cheeked gibbon, Sumatran orangutan, Lowland gorilla, and white-tufted-eared marmoset which has not been described in the prior art as being beta regeneration peptide. This invention evaluated GenBank, Basic Local Alignment Search Tool (BLAST) algorithm and UniProtKB which produced by the UniProt Consortium which consists of groups from the European Bioinformatics Institute (EBI), the Swiss Institute of Bioinformatics (SIB) and the Protein Information Resource (PIR). This sequences (SEQ ID: 4) and amino-acids within the sequence are not contained within the 14-amino acid human Reg3a HIP peptide or the 15-amino acid hamster Reg3gamma peptide, INGAP.

FIG. 19 shows the identification of the Perle Peptide 8-amino acid human Reg sequence (SEQ ID: 8) that has 100% homology with sequences found in other mammals including chimpanzee, rat, mouse, golden hamster, guinea pig, rabbit, pig, sheep, cow, white-cheeked gibbon, Sumatran orangutan, Lowland gorilla, and European domestic ferret which has not been described in the prior art as being beta regeneration peptide. This invention evaluated GenBank, Basic Local Alignment Search Tool (BLAST) algorithm and UniProtKB which produced by the UniProt Consortium which consists of groups from the European Bioinformatics Institute (EBI), the Swiss Institute of Bioinformatics (SIB) and the Protein Information Resource (PIR). This sequences (SEQ ID: 8) and amino-acids within the sequence are not contained within the 14-amino acid human Reg3a HIP peptide or the 15-amino acid hamster Reg3gamma peptide, INGAP.

FIG. 20 shows the identification of the Perle Peptide 7-amino acid human Reg sequence (SEQ ID: 7) that has 100% homology with sequences found in other mammals including chimpanzee, rat, mouse, golden hamster, guinea pig, rabbit, pig, sheep, cow, white-cheeked gibbon, Sumatran orangutan, Lowland gorilla, white-tufted-eared marmoset, European domestic ferret which has not been described in the prior art as being beta regeneration peptide. This invention evaluated GenBank, Basic Local Alignment Search Tool (BLAST) algorithm and UniProtKB which produced by the UniProt Consortium which consists of groups from the European Bioinformatics Institute (EBI), the Swiss Institute of Bioinformatics (SIB) and the Protein Information Resource (PIR). This sequences (SEQ ID: 7) and amino-acids within the sequence are not contained within the 14-amino acid human Reg3a HIP peptide or the 15-amino acid hamster Reg3gamma peptide, INGAP.

FIG. 21 shows the identification of the 9-amino acid human Perle Peptide (SEQ ID: 14) that has 100% homology with sequences found in other mammals including chimpanzee, rat, mouse, golden hamster, guinea pig, rabbit, pig, sheep, cow, white-cheeked gibbon, Sumatran orangutan, and Lowland gorilla which has not been described in the prior art as being beta regeneration peptide.

This invention evaluated GenBank, Basic Local Alignment Search Tool (BLAST) algorithm and UniProtKB which produced by the UniProt Consortium which consists of groups from the European Bioinformatics Institute (EBI), the Swiss Institute of Bioinformatics (SIB) and the Protein Information Resource (PIR). This sequences (SEQ ID: 14) and amino-acids within the sequence are not contained within the 14-amino acid human Reg3a HIP peptide or the 15-amino acid hamster Reg3gamma peptide, INGAP.

FIG. 22 demonstrates the 20-amino acid human sequence (SEQ ID NO: 9) that has been identified within the human Reg receptor that has 100% homology with Reg receptor sequences found in chimp, rat, mouse, guinea pig, rabbit, dog, cow, opossum, galago, white-cheeked-gibbon, Sumatran orangutan, macaque, Lowland gorilla, white-tufted-eared marmoset and horse.

Perle Peptide Derivatives or Analogs

In particular, Perle Peptide derivatives can be made via altering Perle Peptide sequences by substitutions, insertions, or deletions that provide for functionally equivalent or improved molecules. Due to the degeneracy of nucleotide coding sequences, other DNA sequences which encode the same or a substantially similar amino acid sequence as a Perle Peptide or analogs or derivatives thereof may be used in the practice of the present invention. These include, but are not limited to, nucleic acid sequences comprising all or portions of a Perle Peptide that are altered by the substitution of different codons that encode a functionally equivalent amino acid residue within the sequence, thus producing a silent change. Likewise, the Perle Peptide derivatives of the invention include, but are not limited to, those containing, as a primary amino acid sequence, all or part of the amino acid sequence of a Perle Peptide including altered sequences in which functionally equivalent amino acid residues are substituted for residues within the sequence resulting in a silent change. For example, one or more amino acid residues within the sequence can be substituted by another amino acid of a similar polarity that acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Perle Peptide derivatives of the invention also include, but are not limited to, those containing, as a primary amino acid sequence, all or part of the amino acid sequence of a Perle Peptide including altered sequences in which amino acid residues are substituted for residues with similar chemical properties. In a specific embodiment, 1, 2, 3, 4, or 5 amino acids are substituted.

Derivatives or analogs of Perle Peptides include, but are not limited to, those proteins which are substantially homologous to a Perle Peptide or fragments thereof, or whose encoding nucleic acid is capable of hybridizing to the Perle Peptide nucleic acid sequence.

In a specific embodiment, chimeric or fusion proteins may be used in the method of the invention. As used herein, a "chimeric protein" or "fusion protein" comprises Perle a Peptides or an analog or derivative thereof operatively-linked to a non-Perle Peptide or an analog or derivative thereof. Within such a fusion protein, the Perle Peptide or analog or derivative thereof can correspond to all or a portion of a Perle Peptide. In one embodiment, a Perle Peptide fusion protein comprises at least one biologically-active portion of a Perle Peptide. Within the fusion protein, the Perle Peptide or analog or derivative thereof and the non-Perle Peptide polypeptide are "operatively-linked", that is they are fused in-frame with one another. The non-Perle Peptide polypeptide can be fused to the N-terminus or C-terminus of the Perle Peptide or analog or derivative thereof. For example, the fusion protein may be a Perle Peptide protein containing a heterologous signal sequence at its N-terminus. In certain host cells (e.g., mammalian host cells), expression and/or secretion of Perle Peptides or an analog or derivative thereof can be increased through use of a heterologous signal sequence. In yet another example, the fusion protein is a Perle Peptide-immunoglobulin fusion protein in which the Perle Peptide sequences are fused to sequences derived from a member of the immunoglobulin protein family. The Perle Peptide-immunoglobulin fusion proteins can be incorporated into pharmaceutical compositions and administered to a subject to inhibit an immunological response according to the present invention.

Perle Peptides, an analog or derivative thereof, or a Perle Peptide-chimeric or fusion protein for use in the methods of the invention may be chemically modified for the purpose of improving bioavailability, and/or increasing efficacy, solubility and stability. For example, the protein may be covalently or non-covalently linked to albumin, transferrin or polyethylene glycol (PEG).

Perle Peptides, an or analog or derivative thereof, or a Perle Peptides-chimeric or fusion protein for use in the method of the invention can be produced by standard recombinant DNA techniques in accordance with the teachings of the invention. For example, DNA fragments coding for the different polypeptide sequences may be ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. Furthermore, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence [see, e.g., Ausubel, et al. (eds.) CURRENT PROTOCOLS IN MOLECULAR BIOLOGY, John Wiley & Sons, (1992)]. Moreover, many expression vectors are commercially available that already encode a fusion moiety (e.g., a GST polypeptide). A Perle Peptide-encoding nucleic acid can be cloned into such an expression vector such that the fusion moiety is linked in-frame to a Perle Peptide. The fusion protein can be a Perle Peptide protein fused, to a His tag or epitope tag (e.g. V5) to aid in the purification and detection of the recombinant Perle Peptides, or to mask the immune response in a subject. The relatively short amino acid sequences of Perle Peptides and its analogs and derivatives make synthetic production of these valuable peptides readily practicable as well, and a variety of automated instruments for peptide synthesis are commercially available, and synthetic methods for peptide synthesis not requiring automation have long been known and can be used in accordance with the teachings herein to prepare a Perle Peptide or analog or derivative of the invention.

In some embodiments, Perle Peptides, an or analog or derivative thereof, or a Perle Peptide-chimeric or fusion protein can be modified so that it has an extended half-life in vivo using any methods known in the art. For example, Fc fragment of human IgG or inert polymer molecules such as high molecular weight polyethyleneglycol (PEG) can be attached to a Perle Peptide or an analog or derivative thereof with or without a multifunctional linker either through site-specific conjugation of the PEG to the N- or C-terminus of the protein or via epsilon-amino groups present on lysine residues. Linear or branched polymer derivatization that results in minimal loss of biological activity will be used. The degree of conjugation can be closely monitored by SDS-PAGE and mass spectrometry to ensure proper conjugation of PEG molecules to Perle Peptides or an analog or derivative thereof. Unreacted PEG can be separated from Perle Peptide-PEG conjugates by size-exclusion or by ion-exchange chromatography. PEG-derivatized conjugates can be tested for in vivo efficacy using methods known to those of skill in the art.

Derivatives and analogs may be full length or other than full length. Derivatives or analogs of the nucleic acids or proteins of the invention include, but are not limited to, molecules comprising regions that are substantially homologous to the nucleic acids or proteins of the invention, in various embodiments, by at least about 70%, 80%, or 95% identity (with a preferred identity of 80-95%) over a nucleic acid or amino acid sequence of identical size or when compared to an aligned sequence in which the alignment is done by a computer homology program known in the art, or whose encoding nucleic acid is capable of hybridizing to the complement of a sequence encoding the proteins under stringent, moderately stringent, or low stringent conditions. See e.g. Ausubel, et al., CURRENT PROTOCOLS IN MOLECULAR BIOLOGY, John Wiley & Sons, New York, N.Y., 1993, and below.

Antibodies to Perle Peptides and Analogs or Derivatives Thereof

In various embodiments, monoclonal or polyclonal antibodies specific to Perle Peptides or analogs or derivatives thereof can be used in immunoassays to measure the amount of Perle Peptides or analogs or derivatives thereof or used in immunoaffinity purification of a Perle Peptide or analogs or derivatives thereof. A Hopp & Woods hydrophilic analysis (see Hopp & Woods, Proc. Natl. Acad. Sci. U.S.A. 78:3824-3828 (1981) can be used to identify hydrophilic regions of a protein, and to identify potential epitopes of a Perle Peptide or analogs or derivatives thereof.

The antibodies that immunospecifically bind to a Perle Peptide or analogs or derivatives thereof can be produced by any method known in the art for the synthesis of antibodies, in particular, by chemical synthesis or preferably, by recombinant expression techniques. (See, e.g., U.S. Publication No. 2005/0084449, which is incorporated herein in its entirety).

Polyclonal antibodies immunospecific for Perle Peptides or analogs or derivatives thereof can be produced by various procedures well-known in the art. For example, Perle Peptides or analogs or derivatives thereof can be administered to various host animals, including, but not limited to, rabbits, mice, and rats, to induce the production of sera containing polyclonal antibodies specific for Perle Peptides or analogs or derivatives thereof. Various adjuvants may be used to increase the immunological response, depending on the host species, including but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *corynebacterium parvum*. Such adjuvants are also well known in the art.

Monoclonal antibodies can be prepared using a wide variety of techniques known in the art, including the use of hybridoma, recombinant, and phage display technologies, or a combination thereof. For example, monoclonal antibodies can be produced using hybridoma techniques, including those known in the art and taught, for example, in Harlow et al., Antibodies: A Laboratory Manual, (Cold Spring Harbor Laboratory Press, 2nd ed. 1988); and Hammerling et al., in: Monoclonal Antibodies and T Cell Hybridomas 563 681 (Elsevier, N.Y., 1981). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Method for producing and screening for specific antibodies using hybridoma technology are routine and well known in the art. Briefly, mice can be immunized with a non-murine antigen, and once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

The present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with a non-murine antigen with myeloma cells and then screening the hybridomas resulting from the fusion for hybridoma clones that secrete an antibody able to bind to the antigen.

Antibody fragments which recognize specific particular epitopes may be generated by any technique known to those of skill in the art. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Further, the antibodies of the present invention can also be generated using various phage display methods known in the art.

In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with a scFv linker by PCR and cloned into a phagemid vector. The vector is electroporated in E. coli, and the E. coli is infected with helper phage. Phage used in these methods are typically filamentous phage including fd and M13 and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies of the present invention include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; International application No. PCT/GB91/O1 134; International publication Nos. WO 90/02809; WO 91/10737; WO 92/01047; WO 92/18619; WO 93/11236; WO 95/15982; WO 95/20401; and WO97/13844; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; and 5,969,108.

As described in the above references, after phage selection, the antibody coding regions from the phage can be isolated and used to generate whole antibodies or any other desired antigen binding fragment, and expressed in any desired host, including mammalian cells, insect cells, plant cells, yeast, and bacteria, e.g., as described below. Techniques to produce Fab, Fab' and F(ab')2 fragments recombinantly can also be employed using methods known in the art such as those disclosed in PCT publication No. WO 92/22324; Mullinax et al., 1992, BioTechniques 12(6):864-869; Sawai et al., 1995, AJRI 34:26-34; and Better et al., 1988, Science 240:1041-1043.

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lambda constant regions. Preferably, the vectors for expressing the VH or VL domains comprise an EF-1α promoter, a secretion signal, a cloning site for the variable domain, constant domains, and a selection marker such as neomycin. The VH and VL domains may also be cloned into one vector expressing the necessary constant regions. The heavy chain conversion vectors and light chain conversion vectors are then co-transfected into cell lines to generate stable or transient cell lines that express full-length antibodies, IgG, using techniques known to those of skill in the art.

For some uses, including in vivo use of antibodies in humans and in vitro detection assays, it may be preferable to use humanized antibodies or chimeric antibodies. Human antibodies can be made by a variety of methods known in the art including phage display methods described above using antibody libraries derived from human immunoglobulin sequences. See also U.S. Pat. Nos. 4,444,887 and 4,716,111; and International publication Nos. WO 98/46645, WO 98/50433, WO 98/24893, WO98/16654, WO 96/34096, WO 96/33735, and WO 91/10741.

A chimeric antibody is a molecule in which different portions of the antibody are derived from different immunoglobulin molecules. Methods for producing chimeric antibodies are known in the art. See e.g., Morrison, 1985, Science 229: 1202; Oi et al., 1986, BioTechniques 4:214; Gillies et al., 1989, J. Immunol. Methods 125:191-202; and U.S. Pat. Nos. 5,807,715; 4,816,567; 4,816,397; and 6,311,415.

A humanized antibody is an antibody or its variant or fragment thereof which is capable of binding to a predetermined antigen and which comprises a framework region having substantially the amino acid sequence of a human immunoglobulin and a CDR having substantially the amino acid sequence of a non-human immunoglobulin. A humanized antibody comprises substantially all of at least one, and typically two, variable domains (Fab, Fab', F(ab')2, Fabc, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fe), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including IgG1, IgG2, IgG3 and IgG4. Usually the constant domain is a complement fixing constant domain where it is desired that the humanized antibody exhibit cytotoxic activity, and the class is typically IgG1. Where such cytotoxic activity is not desirable, the constant domain may be of the IgG2 class. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental framework region (FR) and CDR sequences, more often 90%, and most preferably greater than 95%. Humanized antibody can be produced using variety of techniques known in the art, including but not limited to, CDR grafting (European Patent No. EP 239,400; International Publication No. WO 91/09967; and U.S. Pat. Nos. 5,225,539; 5,530,101; and 5,585,089), veneering or resurfacing (European Patent Nos. EP 592,106 and EP 519,596; Padlan, 1991, Molecular Immunology 28(415):489 498; Studnicka et al., 1994, Protein Engineering 7(6):805 814; and Roguska et al., 1994, PNAS 91:969 973), chain shuffling (U.S. Pat. No. 5,565,332), and techniques disclosed in, e.g., U.S. Pat. Nos. 6,407,213; 5,766,886; WO 9317105; Tan et al., J. Immunol. 169:1119-25 (2002); Caldas et al., Protein Eng. 13(5):353-60 (2000); Morea et al., Methods 20(3):267-79 (2000); Baca et al., J. Biol. Chem. 272(16):10678-84 (1997); Roguska et al., Protein Eng. 9(10):895-904 (1996); Couto et al., Cancer Res. 55 (23 Supp):5973s-5977s (1995); Couto et al., Cancer Res. 55(8):1717-22 (1995); Sandhu J S, Gene 150(2):409-10 (1994); and Pedersen et al., J. Mol. Biol. 235(3):959-73 (1994). Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature 332:323).

Methods of Preparing Perle Peptides and Analogs or Derivatives Thereof

Any techniques known in the art can be used in purifying Perle Peptides or an analog or derivative thereof, including but not limited to, separation by precipitation, separation by adsorption (e.g., column chromatography, membrane adsorbents, radial flow columns, batch adsorption, high-performance liquid chromatography, ion exchange chromatography, inorganic adsorbents, hydrophobic adsorbents, immobilized metal affinity chromatography, affinity chromatography), or separation in solution (e.g., gel filtration, electrophoresis, liquid phase partitioning, detergent partitioning, organic solvent extraction, and ultrafiltration). See e.g., Scopes, PROTEIN PURIFICATION, PRINCIPLES AND PRACTICE, 3rd ed., Springer (1994). During the purification, the biological activity of Perle Peptides or an analog or derivative thereof may be monitored by one or more in vitro or in vivo assays. The purity of Perle Peptides or an analog or derivative thereof can be assayed by any methods known in the art, such as but not limited to, gel electrophoresis. See Scopes, supra. In some embodiments, Perle Peptides or an analog or derivative thereof employed in a composition of the invention can be in the range of 80 to 100 percent of the total mg protein, or at least 80%, at least 85%, at least 90%, at least 95%, or at least 98% of the total mg protein. In one embodiment, Perle Peptides or an analog or derivative thereof employed in a composition of the invention is at least 99% of the total protein. In another embodiment, Perle Peptides or an analog or derivative thereof is purified to apparent homogeneity, as assayed, e.g., by sodium dodecyl sulfate polyacrylamide gel electrophoresis.

Methods known in the art can be utilized to produce Perle Peptides or an analog or derivative thereof recombinantly. A nucleic acid sequence encoding a Perle Peptide or an analog or derivative thereof can be inserted into an expression vector for propagation and expression in host cells.

An expression construct, as used herein, refers to a nucleic acid sequence encoding a Perle Peptide or an analog or derivative thereof operably associated with one or more regulatory regions that enable expression of a Perle Peptide or an analog or derivative thereof in an appropriate host cell. "Operably-associated" refers to an association in which the regulatory regions and the Perle Peptide or an analog or derivative thereof to be expressed are joined and positioned in such a way as to permit transcription, and ultimately, translation.

The regulatory regions that are necessary for transcription of Perle Peptides or an analog or derivative thereof can be provided by the expression vector. A translation initiation codon (ATG) may also be provided if a Perle Peptide or an analog or derivative thereof gene sequence lacking its cognate initiation codon is to be expressed. In a compatible host-construct system, cellular transcriptional factors, such as RNA polymerase, will bind to the regulatory regions on the expression construct to effect transcription of the Perle Peptide sequence in the host organism. The precise nature of the regulatory regions needed for gene expression may vary from host cell to host cell. Generally, a promoter is required which is capable of binding RNA polymerase and promoting the transcription of an operably-associated nucleic acid sequence. Such regulatory regions may include those 5' non-coding sequences involved with initiation of transcription and translation, such as the TATA box, capping sequence, CAAT sequence, and the like. The non-coding region 3' to the coding sequence may contain transcriptional termination regulatory sequences, such as terminators and polyadenylation sites.

In order to attach DNA sequences with regulatory functions, such as promoters, to a Perle Peptide or an analog or derivative thereof gene sequence or to insert a Perle Peptide or an analog or derivative thereof gene sequence into the cloning site of a vector, linkers or adapters providing the appropriate compatible restriction sites may be ligated to the ends of the cDNAs by techniques well known in the art (see e.g., Wu et al., 1987, Methods in Enzymol, 152:343-349). Cleavage with a restriction enzyme can be followed by modification to create blunt ends by digesting back or filling in single-stranded DNA termini before ligation. Alternatively, a desired restriction enzyme site can be introduced into a fragment of DNA by amplification of the DNA using PCR with primers containing the desired restriction enzyme site.

An expression construct comprising a Perle Peptide or an analog or derivative thereof sequence operably associated with regulatory regions can be directly introduced into appropriate host cells for expression and production of a Perle Peptide or an analog or derivative thereof without further cloning. See, e.g., U.S. Pat. No. 5,580,859. The expression constructs can also contain DNA sequences that facilitate integration of a Perle Peptide or an analog or derivative thereof sequence into the genome of the host cell, e.g., via homologous recombination. In this instance, it is not necessary to employ an expression vector comprising a replication origin suitable for appropriate host cells to propagate and express Perle Peptides or an analog or derivative thereof in the host cells.

A variety of expression vectors may be used, including but are not limited to plasmids, cosmids, phage, phagemids or modified viruses. Such host-expression systems represent vehicles by which the coding sequences of a Perle Peptide or an analog or derivative thereof gene may be produced and subsequently purified, but also represent cells which may, when transformed or transfected with the appropriate nucleotide coding sequences, express Perle Peptides or an analog or derivative thereof in situ. These include, but are not limited to, microorganisms such as bacteria (e.g., *E. coli* and *B. subtilis*) transformed with recombinant bacteriophage DNA, plasmid DNA or cosmid DNA expression vectors containing Perle Peptides or an analog or derivative thereof coding sequences; yeast (e.g., *Saccharomyces, Pichia*) transformed with recombinant expression vectors containing Perle Peptides or an analog or derivative thereof coding sequences; insect cell systems infected with recombinant virus expression vectors (e.g., baculovirus) containing Perle Peptides or an analog or derivative thereof coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing Perle Peptides or an analog or derivative thereof coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as Escherichia coli and eukaryotic cells are used for the expression of a recombinant Perle Peptide or an analog or derivative thereof. For example, mammalian cells such as Chinese hamster ovary cells (CHO) can be used with a vector bearing promoter element from major intermediate early gene of cytomegalovirus for effective expression of a Perle Peptide or an analog or derivative thereof sequence (Foecking et al., 1986, Gene 45:101; and Cockett et al., 1990, Bio/Technology 8:2).

In bacterial systems, a number of expression vectors may be advantageously selected depending upon the use intended for the Perle Peptides or an analog or derivative thereof being expressed. For example, when a large quantity of a Perle Peptide or an analog or derivative thereof is to be produced, for the generation of pharmaceutical compositions of a Perle Peptide or an analog or derivative thereof, vectors that direct the expression of high levels of fusion protein products that are readily purified may be desirable. Vectors include, but are not limited to, the E. coli expression vector pCR2.1 TOPO (Invitrogen); pIN vectors (Inouye & Inouye, 1985, Nucleic Acids Res. 13:3101-3109; Van Heeke & Schuster, 1989, J. Biol. Chem. 24:5503-5509), and the like. Series of vectors like pFLAG (Sigma), pMAL (NEB), and pET (Novagen) may also be used to express the foreign proteins as fusion proteins with FLAG peptide, malE-, or CBD-protein. These recombinant proteins may be directed into periplasmic space for correct folding and maturation. The fused part can be used for affinity purification of the expressed protein. Presence of cleavage sites for specific proteases like enterokinase allows one to cleave off the Perle Peptide or an analog or derivative thereof. The pGEX vectors may also be used to express foreign proteins as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, many vectors to express foreign genes can be used, e.g., Autographa californica nuclear polyhedrosis virus (AcNPV) can be used as a vector to express foreign genes. The virus grows in cells like Spodoptera frugiperda cells. A Perle Peptide or an analog or derivative thereof coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, a Perle Peptide or an analog or derivative thereof coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing Perle Peptides or an analog or derivative thereof in infected hosts (see, e.g., Logan & Shenk, 1984, Proc. Natl. Acad. Sci. USA 8 1:355-359). Specific initiation signals may also be required for efficient translation of inserted Perle Peptides or an analog or derivative thereof coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, and the like (see, e.g., Bittner et al., 1987, Methods in Enzymol. 153:51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript and post-translational modification of the gene product, e.g., glycosylation and phosphorylation of the gene product, may be used. Such mammalian host cells include, but are not limited to, PC12, CHO, VERY, BHK, HeLa, COS, MDCK, 293, 313, W138, BT483, Hs578T, HTB2, BT2O and T47D, NS0 (a murine myeloma cell line that does not endogenously produce any immunoglobulin chains), CRL7O3O, and HsS78Bst cells. Expression in a bacterial or yeast system can be used if post-translational modifications are found to be non-essential for a desired activity of Perle Peptides or an analog or derivative thereof.

For long-term, high-yield production of properly processed Perle Peptides or an analog or derivative thereof, stable expression in cells is preferred. Cell lines that stably express Perle Peptides or an analog or derivative thereof may be engineered by using a vector that contains a selectable marker. By way of example but not limitation, following the introduction of the expression constructs, engineered cells may be allowed to grow for 1-2 days in an enriched media, and then are switched to a selective media. The selectable marker in the expression construct confers resistance to the selection and may, depending on the vector construct and host cell employed, allow cells to stably integrate the expression construct into their chromosomes and to grow in culture and to be expanded into cell lines. Such cells can be cultured for a long period of time while Perle Peptides or an analog or derivative thereof is expressed continuously.

A number of selection systems may be used, including but not limited to, antibiotic resistance (markers like Neo, which confers resistance to geneticine, or G-418 (Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62: 191-217; May, 1993, TIB TECH 11(5):155-215); Zeo, for resistance to Zeocin; and Bsd, for resistance to blasticidin); antimetabolite resistance (markers like Dhfr, which confers resistance to methotrexate, Wigler et al., 1980, Natl. Acad.

Sci. USA 77:357; and O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); and hygro, which confers resistance to hygromycin (Santerre et al., 1984, Gene 30:147). In addition, mutant cell lines including, but not limited to, tk-, hgprt- or aprt-cells, can be used in combination with vectors bearing the corresponding genes for thymidine kinase, hypoxanthine, guanine- or adenine phosphoribosyl-transferase. Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); Chapters 12 and 13, Dracopoli et al. (eds), of Current Protocols in Human Genetics, John Wiley & Sons, NY (1994); and Colberre-Garapin et al., 1981, J. Mol. Biol. 150: 1.

The recombinant cells may be cultured under standard conditions of temperature, incubation time, optical density and media composition. However, conditions for growth of recombinant cells may be different from those for expression of Perle Peptides or an analog or derivative thereof. Modified culture conditions and media may also be used to enhance production of Perle Peptides or an analog or derivative thereof. Any techniques known in the art may be applied to establish the optimal conditions for producing Perle Peptides or an analog or derivative thereof.

An alternative to producing Perle Peptides or a fragment thereof by recombinant techniques or purification from natural sources is peptide synthesis. For example, an entire Perle Peptides or an analog or derivative thereof, or a protein corresponding to a portion of Perle Peptides or an analog or derivative thereof, can be synthesized by use of a peptide synthesizer. Conventional peptide synthesis or other synthetic protocols well known in the art may be used.

Proteins having the amino acid sequence of Perle Peptide or an analog or derivative thereof or a portion thereof may be synthesized by solid-phase peptide synthesis using procedures similar to those described by Merrifield, 1963, J. Am. Chem. Soc., 85:2149. During synthesis, N-$\alpha$-protected amino acids having protected side chains are added stepwise to a growing polypeptide chain linked by its C-terminal and to an insoluble polymeric support, i.e., polystyrene beads. The proteins are synthesized by linking an amino group of an N-$\alpha$-deprotected amino acid to an $\alpha$-carboxyl group of an N-$\alpha$-protected amino acid that has been activated by reacting it with a reagent such as dicyclohexylcarbodiimide. The attachment of a free amino group to the activated carboxyl leads to peptide bond formation. The most commonly used N-$\alpha$-protecting groups include Boc, which is acid labile, and Fmoc, which is base labile. Details of appropriate chemistries, resins, protecting groups, protected amino acids and reagents are well known in the art and so are not discussed in detail herein (See, Atherton et al., 1989, Solid Phase Peptide Synthesis: A Practical Approach, IRL Press, and Bodanszky, 1993, Peptide Chemistry, A Practical Textbook, 2nd Ed., Springer-Verlag).

Purification of the resulting Perle Peptides or an analog or derivative thereof is accomplished using conventional procedures, such as preparative HPLC using gel permeation, partition and/or ion exchange chromatography. The choice of appropriate matrices and buffers are well known in the art and so are not described in detail herein.

With the foregoing detailed description of the reagents and methods of the invention, the following Examples are provided to illustrate various aspects of the invention.

EXAMPLES

This invention identifies homologous peptide sequences known as "Perle peptides" that are found within the binding arm of the human Reg1a, Reg1b, Reg3a and Reg4 protein and evaluates their role as beta regeneration agents. None of the Perle peptides are contained within the previously described the human 14-amino acid Reg3a HIP peptide or the hamster 15-amino acid Reg3gamma peptide, INGAP. A 20-amino binding region within the 919-amino acid Reg receptor was discovered from which stimulating antibodies were generated to serve as Reg peptidomimetics.

Included are specific methodologies for the reversal of new onset and existing type 1 and 2 diabetes and for the definitive treatment of those with PreDiabetes, insulin resistance, insulin deficiency, beta cell deficiency or abnormal glucose metabolism, utilizing Perle peptides, as well as studies designed to evaluate the following:

1) Whether Perle peptides may interact with or directly bind to the Reg Receptor when compared to the human 14-amino acid Reg3a peptide, HIP.
2) Whether a binding region on the Reg Receptor could be identified and stimulatory antibodies could be generated to this region that could serve as Reg peptidomimetics; and
3) Whether Perle peptides stimulate downstream signaling and trafficking of the Reg Receptor from the cytoplasmic membrane to the nucleus
4) Methods for Reversing new onset and existing type 1 diabetes and Latent Autoimmune Diabetes of Adulthood utilizing Perle peptides, including formulations, derivatives, optimized forms including peptidomimetics and stimulatory antibodies to the Reg Receptor for the accelerated generation and maintenance of the new beta cells with methodology, which has not previously been described. These methods include the use of Perle peptides, including formulations, derivatives, optimized forms including peptidomimetics and stimulatory antibodies to the Reg Receptor for the accelerated generation of beta cells, or other beta cells stimulating agents that are specifically initiated on the day of the immune nadir when one or more immunomodulary agents are given to a patient with diabetes. The day of the immune nadir varies by immunomodulatory agent. Also, specific methods are provided for optimizing the glycemic milieu in a patient with type 1 diabetes prior to initiation of Perle peptides, including formulations, derivatives, optimized forms including peptidomimetics and stimulatory antibodies to the Reg Receptor for the accelerated generation of beta cells along with methods tapering insulin as new beta cells are generated.
5) Methods for Reversing new onset and existing type 2 diabetes, PreDiabetes, conditions of insulin resistance, insulin deficiency, beta cell deficiency and/or abnormal glucose metabolism. These methods include the use of Perle peptides, including formulations, derivatives, optimized forms including peptidomimetics and stimulatory antibodies to the Reg Receptor for the accelerated generation of beta cells and include specific methods are provided for optimizing the glycemic milieu in a patient with new and existing type 2 diabetes prior to initiation of Perle peptides, including formulations, derivatives, optimized forms including peptidomimetics and stimulatory antibodies to the Reg Receptor for the accelerated generation of beta cells, along with methods tapering oral and subcutaneous diabetes agents including insulin, as new beta cells are generated.

6) Methods for Reversing new onset and existing type 1 and 2 diabetes, PreDiabetes, conditions of insulin resistance, insulin deficiency, beta cell deficiency and/or abnormal glucose metabolism using of Perle peptides, including formulations, derivatives, optimized forms including peptidomimetics and stimulatory antibodies to the Reg Receptor for the accelerated generation of beta cells by ex-vivo transformation of human extra-islet tissue including ductal, acinar and progenitor cells, human embryonic stem cells, human adult bone-marrow derived cells, induced pluripotent stem cells, mesenchymal stem cells, umbilical cord stem cells, or other stem cells and may include resident populations of endogenous stem cells that exist within the adult pancreas that are then delivered to patients with diabetes and other conditions of insulin deficiency via the umbilical vein, portal venous systemic, hepatic artery, subcutaneous delivery with and without organ specific targeting and may include direct administration to the pancreas or liver.

Example 1

Determining the Binding of Perle Peptides to the Reg Receptor

Reg peptides have been shown in the prior art to be rate limiting in the development of new beta cells. Based upon the structure and 3-dimensional alignment, folding and properties of the amino acids within the human Reg1a, Reg1b, Reg3a and Reg 4 proteins, common peptide sequences were identified that are present in a right protrusion (circled in FIG. 3). This invention identifies homologous peptide sequences that are not contained within the previously described 14-amino acid human Reg3a peptide (HIP) and a 15-amino acid hamster peptide (INGAP). Investigation was then undertaken to determine if the Perle peptides may directly or indirectly bind to the Reg Receptor.

Previously both a 14-amino acid human Reg3a peptide (HIP) and a 15-amino acid hamster peptide (INGAP) have been shown to generate new beta through the transformation of human extra-islet exocrine tissue containing ductal, acinar and progenitor cells. Additionally, BrDU labeling, considered to be the gold standard in determining whether new beta cells generated are derived from existing beta cells by a process of budding versus the new beta cells being derived from extra-islet exocrine tissue, has demonstrated that not only do both the 14-amino acid human Reg3a peptide (HIP) and the 15-amino acid hamster peptide (INGAP) result in new beta cells, but also the new beta cells are derived from extra-islet exocrine tissue. The mechanism of action of both HIP and INGAP is via their interaction with the Reg Receptor, which is found in human the extra-islet ductal tissue.

This discovery of new and shorter peptides that bind directly to the Reg Receptor provides new therapies for patients with new onset or existing type 1 or type 2 diabetes and those with PreDiabetes, insulin resistance, insulin and/or beta cell deficiency, or abnormal glucose metabolism, which may be more potent, efficient and cost-effective. There has been no previous description of the Perle Peptides and their ability to directly bind to the Reg Receptor.

FIG. 7 demonstrates the results from studies conducted to demonstrate Reg Receptor expression and purification utilizing 293T cells that were transfected with Reg Receptor expression plasmid DNA. Cells were collected after 72 hours. The Reg Receptor was tagged with FLAG epitope and FLAG resin was utilized to purify out the Reg Receptor. As shown in FIG. 7, the Reg Receptor was highly purified. The Reg Receptor was purified by Anti-Flag M2 affinity gel. Target protein was confirmed by 4-12% SDS-PAGE and Western-blot. FIG. 7a demonstrates the use of sodium dodecyl sulfate polyacrylamide gel electrophoresis (SDS-PAGE) to illustrate the high purity of the Reg Receptor. FIGS. 7b and 7c are the Western blot results showing that the purified protein is the Reg Receptor using the antibody to the Reg Receptor (CD104). The Reg Receptor is shown In FIG. 7 to be highly purified.

To then demonstrate the direct binding of Perle Peptides to the Reg Receptor, the purified Reg receptor was coated onto 96 well plate by using bicarbonate coating buffer, pH 9.6; 4° C. overnight at concentration 3 ug/ml, 100 ul per well. Plates were coated overnight coated plate and washed three times with 0.5×TBST and blocked with 3% BSA and rotated at room temperature for 1 hour. After blocking, plates were washed three times with 0.5×TBST. Peptides were then diluted with TBST buffer and added into wells in duplicate then left to bind at room temperature for 1 hour. After washing three times, 100 ng/ml strep-HRP was added into plate at 100 ul/well, and rotated at room temperature for one hour. ABST reagents were warmed to room temperature, mixed immediately before using. Then 100 ul was added to each well and read after 25 minutes reaction and absorbance was evaluated at 405 nm by a Spectramax M5 plate reader. The purified Reg Receptor was coated on plates. Then plates were blocked with BSA solution. Subsequently, the Perle peptides were added into the wells, and HRP-straptavidin and its substrates were added into the wells to reveal the interaction between Receptor and the Perle peptide.

As shown in FIG. 9, the 7-amino acid Perle peptide, the 8-amino acid Perle peptide and the 9-amino acid Perle peptide all bind directly to Reg Receptor. The 8-amino acid peptide appeared to be the strongest in binding to the Reg Receptor. The scrambled control peptide did not bind to Reg Receptor. The 14-amino acid human Reg3a peptide (HIP), has demonstrated the ability to generate new beta cells through the interaction with the Reg Receptor, but has not been shown to directly bind to the Reg Receptor. The 14-amino acid human Reg3a peptide (HIP), was shown in this study to have the same level of binding as the scrambled peptide (FIG. 9). The 7, 8 and 9-amino acid Perle Peptides sequences are not contained within the 14-amino human Reg3a peptide (HIP) sequence or the 15 amino acid hamster 3gamma peptide (INGAP).

This study demonstrates the ability of Perle peptides to bind directly to the Reg Receptor and to be potential candidates for therapy for patients with new onset or existing type 1 or type 2 diabetes, and those with insulin resistance, insulin and/or beta cell deficiency, or abnormal glucose metabolism.

Example 2

Identification of a Binding Region within the Reg Receptor and Generation of Stimulatory Antibodies to Reg Receptor Binding Site Previous studies have identified that Reg proteins and peptides act through a 919-amino acid cell-surface protein. Studies were undertaken to identify the binding site for Perle peptides and develop stimulatory compounds to accelerate the progression of beta cell formation by stimulating the binding sites on the Reg Receptor. For the production of stimulatory antibodies, sequences were evaluated within the N-terminal portion of the putative Reg Receptor (amino acids 1-332) (SEQ ID NO:13), which is the amino acid region of Reg Receptor that is not contained in the other members of the of Exostoses family, and thus is hypothesized to be the Reg binding domain.

Consistently, in Enzyme ImmunoAssay studies measuring titers from peptide sequences within SEQ ID NO:13, resulted in very high polyclonal antibodies being raised to a 20 amino acid Reg Receptor sequence of 20 amino acid peptide (SEQ ID NO:9) (amino acids 117-136). The results of the Enzyme ImmunoAssay are summarized in FIG. 11. FIG. 12 demonstrates the standard protocol used for development of polyclonal antibodies to peptide regions within Reg Receptor.

Data sets were taken from the bleed after the day 0 and day 21 boosts. The animals were injected with a peptide of SEQ ID NO: 9 and were conjugated to keyhole limpet hemocyanin (KLH). The screening antigen is not conjugated to KLH so that the response solely to the peptide and not to KLH can be identified. The 50% titer is a dilution value where the signal is half-way between the peak and the baseline, so the higher the dilution value (titer), the greater the response to the antigen. The positive control is an internal control that was generated from ovalbumin antibodies in rabbit. At a dilution of 1:750,000, the absorbance fell within a range of 0.45 to 0.9. In the case of the response to SEQ ID NO: 9, there was a high response (FIG. 11). The test bleed taken 31 days after the day 0 and 21 day boosts for CD 153 showed a 50% titer of 36,000 which is an average response, and CD 154 showed a 50% titer of 125,000 which is a high response according to the polyclonal titer reference range shown in FIG. 13. Studies are underway to evaluate the efficacy of the antibody generated with and without the presence of Perle peptides demonstrating that the antibodies raised are stimulatory to the Perle peptides and interact with Reg Receptor to generate beta cells in human extra-islet exocrine tissue including progenitor cells.

Based on the development of stimulatory antibodies that were generated to a 20-amino acid peptide region within the Reg Receptor (FIG. 11), this invention identifies the potential to utilize stimulatory antibodies for the generation of new beta cells as well as for the development of peptidomimetics utilizing the domain binding site of Perle peptides on the Reg Receptor for the treatment of diabetes and conditions of insulin and/or beta cell insufficiency or loss.

Example 3

Impact of Perle Peptides on Reg Receptor Translocation

Western blot analyses were utilized to evaluate and confirm the impact of Perle peptide on the Reg Receptor translocation from the cytoplasmic membrane, through the cytoplasm and to the nucleus and to determine if there was a measurable enhancement when Perle peptides were added to human extra-islet ductal tissue. The Western blot analyses of cytosolic and nuclear fractions are shown in FIG. 11. The 8-amino acid Perle peptide demonstrated the greatest ability to result in Reg Receptor translocation from the cell surface membrane to nucleus (FIG. 11).

Human extra-islet ductal cells were seeded in T75 flasks in Dulbecco's Modified Eagle media containing 10% fetal bovine serum. The cells were incubated at 37° C., 5% $CO_2$ for 24 hours and then treated with Perle peptide at the final concentration of 167 nM. This treatment was performed once a day for four days. On the fifth day the cells were broken to obtain the cell lysates. In these cell extracts the total protein levels were determined, and 50 micrograms of total protein were used to perform the western blot analysis. The samples containing 50 micrograms of proteins were diluted in loading buffer and loaded into each well of the gel. For gels run under reducing conditions, the buffer also contained 5% of the reducing agent beta-mercaptoethanol.

Analyses were performed from cytoplasmic extracts were obtained in 10 mM HEPES (pH 8.0), 1 mM EDTA, 1.5 mM $MgCl_2$, 10 mM KCl, 0.5 mM DTT, 200 mM sucrose and 0.5% Nonidet P-40. Nuclear extracts were obtained in 20 mM HEPES (pH 7.9), 0.75 mM $MgCl_2$, 210 mM NaCl, 50 mM KCl, 1 mM EDTA, 10% glycerol, and 0.5 mM of dithiothreitol. Both extraction buffers contained 0.5 mM PMSF, 1 µg/ml leupeptin, 1 µg/ml aprotinin, 2.5 mM $Na_4P_2O_7$, 1 mM β-glycerophosphate, and 1 mM $Na_3VO_4$. Protein extracts were size fractionated on SDS-polyacrylamide gels and transferred to nitrocellulose. After blocking in 3% milk in Tris-buffered saline (pH 7.4), blots were sequentially incubated with rabbit anti-human Reg Receptor antibody overnight at 4° C. and appropriate horseradish peroxidase-conjugated secondary antibody. Secondary signals were developed with chemiluminescence substrate and analyzed by autoradiography. Fractions and quality control utilized the fractions with two antibodies, GAPDH as a cytosol molecule and Lamin B is a nuclear molecule. Both GADPH and Lamin B were demonstrated in this invention to serve as excellent controls for the nuclear and cytosolic fractions (FIG. 10). FIG. 10 demonstrates that Western blot analyses of nuclear levels of Reg Receptor at time points with and without the presence of Perle peptides.

Example 4

Methods of Treating New and Existing Type 1 Diabetes Including Latent Autoimmune Diabetes of Adulthood Utilizing Perle Peptides, Derivatives, Optimized Versions, Peptidomimetics or Stimulatory Antibodies to the Reg Receptor The primary way in which patients with type 1 or later-stage type 2 diabetes manage their disease is by administering insulin, either via subcutaneous injection or by using a subcutaneous pump infusion. As well as the obvious lifestyle disadvantages, insulin therapy does not match the body's normal glucose control mechanisms and therefore does not fully manage glucose fluctuations.

Even the best-controlled type 1 diabetic patients do not have anything remotely like a normal glucose metabolism, nor are normal hemoglobin A1C levels in reach for most patients with diabetes. Despite the many new insulin preparations, sensors, pumps, new oral and injectable medications, achieving normal glucose levels and hemoglobin A1C levels remains out of reach for most diabetes patients. Sensor data from non-diabetic humans demonstrate that 80% of all measured glucose levels lie within 60-100 mg/dL, with mean peak glucose levels after meals of <120 mg/dL. Christiansen J S. et al., http://www.diabetessymposium.org/index.php?menu=view&id=322

Linear regression curves from the Diabetes Control and Complications Trial (DCCT) and the United Kingdom Prospective Diabetes Study (UKPDS) show that A1C levels above 5.5% are associated with more complications. DCCT Research Group. Diabetes. 1996; 45(10):1289-1298. Stratton I M et al., BMJ. 2000; 321(7258):405-412. This data is supported by A1C levels from the EPIC-Norfolk trial among non-diabetic individuals, which found that A1C levels above 5.5% are associated with significantly increased risks for vascular-related morbidity and mortality Khaw K T et al., BMJ. 2001; 322(7277):15-18.

Glucose homeostasis requires an adequate number of beta cells, as illustrated by the inability to restore normoglycemia among diabetic patients even when intensive regimens of medications are utilized. The DCCT investigators set, as a major treatment outcome goal, a mean A1C over the trial period of ≤6.05% without an increased risk for hypoglycemia. Sensor-augmented pumps recently were shown to improve A1C levels from 8.3% to 7.5%, over 12 months, with further reductions to 7.4% after an additional 6 months of treatment. These achievements were made without the associated weight gain or hypoglycemia seen in the DCCT. Despite technological advances in sensors and pumps, sensor-augmented pump therapy did not improve A1C levels as much as those seen in the DCCT decades ago. Bergenstal R M, N Engl J Med, 2010; 363(4):311-320. Bergenstal R M, Diabetes Care. 2011; 34(11):2403-2405. Despite many new classes of insulin therapy that are now available for type 1 diabetes, a normal hemoglobin A1C of 5.5% is still impossible to achieve in patients with type 1 diabetes with the current therapies and technologies. Even with decades of research and the advent of pancreatic islet cell transplantation, the success has not been replicated in the United States. At four years post-transplant, fewer than 10% of patients who have received islet cell transplants remain insulin independent.

Thus despite all of the new therapies and technologies, diabetes remains the leading cause of new blindness, amputations and kidney failure requiring dialysis or transplantation. Providing and protecting new beta cells from one's own pancreatic progenitor cells provide patients an opportunity to reverse this disease state.

To reverse type 1 diabetes, this invention posits that a two-step process will be necessary. First, an immune tolerance agent will need to be utilized, followed by a beta cell agonist including Perle peptides, derivatives, optimized versions, peptidomimetics or stimulatory antibodies to the Reg Receptor. FIG. 14 presents a summary of methods to reverse new and existing type 1 diabetes and Latent Autoimmune Diabetes of Adulthood by utilizing beta cell agonists including Perle peptides, derivatives, optimized versions, peptidomimetics or stimulatory antibodies to the Reg Receptor. In type 1 diabetes, delivery of an immune tolerance agent prior to a beta cell regeneration agent is hypothesized in this invention to improve the ability to preserve new beta formed from Perle peptides.

Furthermore, this invention specifically describes the methods and timing for usage of beta cell agonists including Perle peptides, derivatives, optimized versions, peptidomimetics or stimulatory antibodies to the Reg Receptor for the treatment of new and existing type 1 diabetes and Latent Autoimmune Diabetes of Adulthood. This invention includes methods that have not previously been described for initiation and usage of beta agonists including Perle peptides, derivatives, optimized versions, peptidomimetics or stimulatory antibodies to the Reg Receptor, in type 1 and Latent Autoimmune Diabetes of Adulthood patients at the time of the immune nadir after initiation of an immune modulator, in order to optimally prevent immune attack on the new beta cells generated by beta cell agonists including Perle peptides, derivatives, optimized versions, peptidomimetics or stimulatory antibodies to the Reg Receptor. The time of the immune nadir varies with each immunomodulation agent that has been utilized in new onset type 1 diabetes.

Furthermore, initiating a beta cell agonist including Perle peptides, derivatives, optimized versions, peptidomimetics or stimulatory antibodies to the Reg Receptor at the time of the immune nadir provides potentiation of an amnestic response because new beta cells will be formed during a window when beta cells are least likely to be recognized as being foreign, and thus less likely an antigen to autoimmune attack. FIG. 15 illustrates the two-step approach to reverse type 1 diabetes in new onset and existing type 1 diabetes patients and among patients with Latent Autoimmune Diabetes of Adulthood.

As new beta cells form among type 1 patients from the immune agent and Perle peptides, derivatives, optimized versions, peptidomimetics or stimulatory antibodies to the Reg Receptor, exogenous insulin must be reduced, because maintaining the glucose milieu within a narrow range is critical to beta cell regeneration. Beta cell formation will not occur in conditions of hypoglycemia. Formation of beta cells will also not optimally occur with extreme hyperglycemia.

The elegance of a normally functioning pancreas with its the many unique feedback loops to prevent both hyperglycemia and hypoglycemia, is illustrated by the published data taken immediately after the 44-day fast, before eating, from the performance artist, David Blaine Blaine's glucose levels were in the normal range, at 5.2 mmol/L with insulin levels of 3.6 mU/L, which was below the range of control subjects (4.0-20 mU/L). The low insulin level is an illustration of the homeostatic glucose mechanisms that protectively down-regulate insulin in order to prevent hypoglycemia in a fasting individual. Korbonits M, et al., Eur J. Endocrinol. 2007; 157 (2):157-166.

Although more than a dozen immune tolerance agents have restored glycemic control in NOD mice, but when these agents have been utilized in human trials among new onset type 1 diabetes, no immune tolerance agent to date have rendered human type 1 patients insulin-free including: Cyclosporine, teplizumab, otelixizumab, GAD vaccine, the heat shock protein, Diapep 27, the BCG vaccine. In mice, the natural rate of beta cell regeneration is sufficient to augment the immune tolerance. In humans this rate is not enough, except under conditions of acute pancreatic injury such as pancreatitis and pancreatic stones. Therefore, included in this invention is the combination therapy of a targeted immune tolerance agent along with an agent that stimulates beta regeneration, which is initiated at the immune nadir has the potential to reverse type 1 diabetes in humans.

Many of the immune tolerance agents have demonstrated the ability to provide persistent immunity for years following treatment, but despite immunity, which protects remaining beta cells present, the generation of new beta cells is not adequate to render patients insulin-free although some of the immune tolerance agents, including Cyclosporine, anti-CD3 antibodies, GAD vaccine, Diap277 and the BCG vaccine have resulted in improved stimulated c-peptide representing improvement in endogenous insulin. Cyclosporine has rendered 50% of new onset patients with type 1 diabetes, insulin free at 1 year. Bougneres et al., N Engl J Med; 1988 (318)11: 663-670. For example, four years after the GAD vaccine treatment was given, there was persistent improvement in memory T and B cell responses. Axelsson S. et al. PLoS One. 2011; 6(12). Similarly, two anti-CD3 antibodies have also shown preservation of remaining endogenous insulin out to five years after a single course of therapy. Herold K C, et al. Clin Immunol. 2009; 132(2):166-73. Keymeulen B. et al. Diabetologia 2010; 53(4):614-23.

Proof of the elasticity of the pancreas with respect to the generation of the new beta cells has also been shown among women with type 1 diabetes for an average of twenty years, who have been able to completely come off of insulin during their pregnancy with documentation of normalization of C-peptide. As many as ⅓ of women have a dramatic reduction in insulin requirements, with some women coming off insulin completely during their pregnancy despite having undetectable levels of C-peptide at the onset of pregnancy. Several mechanisms occur in pregnancy are unique and provide a unique milieu for a person with type 1 diabetes to be insulin-free during their pregnancy including the 1) Downregulation of the mother's immune system to prevent rejection of the fetus 2) Increased beta cell generation in pregnancy with normal glucose levels in pregnancy among both diabetic and non-diabetic women being 25 mg/dL lower than in the non-pregnant state and 3) Upregulation of the Reg peptide, which is typically only upregulated during times of acute injury, but also found to be upregulated during pregnancy. Ilic S et al., Diabetologia 2005; 43: 1329-1330, Altschul S F., Nucleic Acids Res. 25:3389-3402.

To date, several teams have demonstrated the ability to reverse diabetes and to generate normoglycemia in rodent models utilizing Reg peptides. Two teams have also demonstrated that by utilizing human ductal cells isolated from islets following human cadaveric removal of the pancreas, that the 14 amino-acid human Reg3a peptide (HIP), and the 15-amino acid hamster Reg3gamma peptide (INGAP) augments and enhances the in vitro differentiation of non-endocrine cells into islet clusters containing new beta cells.

Human trials with the 15-amino acid hamster Reg3 gamma peptide (INGAP) demonstrated a 27% rise in stimulated C-peptide by day 56 among human type 1 patients ($p<0.001$) Dungan K M et., Metab Res Rev. 2009; 25(6):558-565. All patients had baseline C-peptide levels≤0.3 ng/m; however, they were not treated with any immune tolerance agents to protect new islet formation from subsequent immune attack. It was noted that 22% of the patients in one of the active treatment arms had >50% increase in GAD65 antibody titers, while no changes were noted with placebo. Among type 1 diabetes, cytokine-induced beta cell death preferentially affects the newly forming beta cells, thus it can be hypothesized that the increased GAD65 antibodies may have been a marker of the formation of new beta cells, and autoimmunity to newly formed beta cells may have negatively impacted study outcomes in terms of hemoglobin A1C and stimulated C-peptide, a marker of endogenous insulin production.

This invention hypothesizes that had patients enrolled in this trial been pretreated with an immune tolerance agent, such as cyclosporine, there could have been a more significant rise in stimulated C-peptide. Furthermore, after reviewing the data on immune tolerance agents that have been utilized in new onset type 1 patients that have completed human trials, each immune tolerance agent has a unique time in which patients develop an immune nadir. For example, the immune nadir occurs on day 6 following intravenous treatment with cyclosporineanti-CD3 antibody, teplizumab and the immune nadir among those treated with the BCG vaccine occurs week 5, after the second BCG injection.

Therefore, this invention includes the optimal time to initiate usage of a beta cell agonist, including Perle peptides, derivatives, formulations, optimized versions, Perle peptidomimetics and stimulatory antibodies to the Reg receptor, is at the immune nadir for the given immune tolerance agent. This invention includes the initiation of beta agonist including Perle peptides, derivatives, formulations, optimized versions, Perle peptidomimetics and stimulatory antibodies to the Reg receptor specifically during immune nadir with any of the immune tolerance agents which varies between agents utilized. Also for the first time that by initiating Perle peptides at the immune nadir, there is the potential ability to generate an amnestic response with the potential of the immune system to recognize as foreign, the new beta cells generated by Perle peptides, derivatives, formulations, optimized versions, Perle peptidomimetics and stimulatory antibodies to the Reg receptor (FIG. 14).

Perle peptides, formulations, derivatives, peptidomimetics, and stimulatory antibodies to the Reg Receptor may be utilized with one or more of many immune modulators to protect new beta cells formed by Perle peptides, formulations, derivatives, peptidomimetics, and stimulatory antibodies to the Reg Receptor. The types of agents include but are not limited to general immunosuppressant agents, which have typically been used in organ transplants, specifically targeted antibodies to those lymphocytes which attack the islets, along with other agents such as Vitamin D, in which a deficiency has been associated with a higher incidence of diabetes. Agents include cyclosporine, mycophenolate mofetil, Rituximab, an anti CD20 agent, which is an FDA approved agent for the treatment of B-lymphocyte lymphoma. Other immune agents include, but are not limited to: cyclosporine, the anti-CD3 antibodies, hOKT3 gamma1 (Ala-Ala) (teplizumab), and the monoclonal antibody TRX4 (ChAglyCD3). The immune tolerance agent may also include, Polyclonal Anti-T-Lymphocyte Globulin (ATG), CTLA4-Ig (Abatacept) a selective co-stimulation modulator as it inhibits the co-stimulation of T cells, or Campath-1H, (Anti-CD52 Antibody), a humanized monoclonal antibody to T-cells, or Alpha-1 antitrypsin (AAT) is a serine proteinase inhibitor.

Any of the following immune tolerance agents have had limited success, but none have rendered patients insulin-free, and could be used in this method. Polyclonal Anti-T-Lymphocyte Globulin (ATG), DiaPep277, a derivative Heat Shock Protein 60, which is a heat shock protein and believed to impact the release of cytokines and pro-inflammatory cells which destroy beta cells, is being studied in adults and children with successful outcomes with newly diagnosed patients with diabetes and also in patients with Latent Autoimmune Diabetes in Adults (LADA). Another agent is the GAD antibody vaccine based on the 65 kDa isoform of the recombinant human glutamic acid decarboxylase protein (rhGAD65). CTLA4-Ig (Abatacept) inhibits a crucial stimulatory pathway in the activation of T cells. By this mechanism, the drug is thought to arrest or slow the T cell mediated autoimmune destruction of insulin producing cells and preserves their function. CTLA-4 Ig is being trialed as an intravenous agent begun within three months of diagnosis and then monthly for a total of 25 treatments. CampathH1 is another immune tolerance agent being trialed among new onset type 1 diabetes and may be utilized in conjunction with Perle peptides, formulations, optimized versions, peptidomimetics and stimulating antibodies to a binding region on the Reg receptor identified in this invention. Additionally, Alpha-1 antitrypsin (AAT) is a serine proteinase inhibitor is currently in study to preserve beta function among newly diagnosed type 1 patients. Cyclosporine has rendered 50% of new onset patients with type 1 diabetes, insulin free at 1 year by helping retain the 10% or so remaining islets after the initial attack on the beta cells. Bougneres et al., N Engl J Med; 1988 (318)11: 663-670. Unfortunately, when these patients were followed out to six years, the beta cell mass declined, but of notable interest, each year that patients remained on cyclosporine, the percentage of antibodies attacking islets was significantly lower each year than patients not treated with cyclosporine. De Filippo et al. Diabetes. 1996. 45(1):101-4. The ability to have the Perle Peptides that are enclosed in this invention, given in combination with a beta cell immune protector, may truly reflect a treatment that addresses the underlying pathologies of type 1 diabetes.

Optimal glycemic control is critical not only after but also prior to initiating a beta agonist including Perle peptides, derivatives, optimized versions, peptidomimetics or stimulatory antibodies to the Reg Receptor. Required is a 4-week period of intensification of glucose control before the initiation of beta agonists including Perle peptides, derivatives, optimized versions, peptidomimetics or stimulatory antibodies to the Reg Receptor in which patients should closely monitor both pre and postprandial blood glucose levels.

During this period of optimization of glycemic control, the glucose goal for patients may be between 100 and 200 mg/dL at all times. In order to achieve the optimized glucose goals to initiate Perle peptides, derivatives, optimized versions, peptidomimetics or stimulatory antibodies to the Reg Receptor, patients may utilize a medical team with state-of-the-art diabetes tools including subcutaneous continuous monitoring systems. The primary goal will be to ensure that the glucose levels do not fall below 70 mg/dL during the optimization period. Should there be any episodes of symptomatic hypoglycemia or the glucose levels fall below 70 mg/dL, modifications in the patient's insulin regimen must be made with re-initiation of the intensification of glucose levels for four weeks.

Methods for using a Perle Peptide in a newly diagnosed or pre-existing patient with type 1 diabetes would utilize an immune tolerance agent. For example, if the immune tolerance agent given to a patient with new onset type 1 diabetes is selected to be cyclosporine, then patient would receive 7.5 mg/kg/day orally for 7 days before Perle peptides are begun. In order to decrease exposure to high peak concentrations of cyclosporine, half the daily dosage will be given with breakfast and half with dinner. The dosage will be adjusted on days 3, 7, 15, 30, and 45 of treatment, to maintain trough levels of cyclosporine between 150 and 350 ng per milliliter of as evaluated by standard assay. After day 45 of treatment the trough levels will be determined monthly and then 7 days after each modification of dosage. Optimized Perle Peptides will be started on day eight after seven days of treatment cyclosporine and begun at dosages of 1 mg/kg subcutaneously with the two largest meals If the immune tolerance agent is teplizumab, then patients would receive six consecutive days of intravenous teplizumab on a weight based dosage and on day six of treatment, initiation would begin at (1 mg/kg) subcutaneously twice daily of optimized Perle peptide (eg: SEQ ID: 8) modified by blocking (i.e., end-capping of the amino and carboxyl termini of the selected Perle peptide with acetyl and amide groups). After initiation of the Perle peptide, based on glucose levels, exogenous insulin would be tapered as described below.

If the immune tolerance agent selected is the heat shock protein 60, DiaPep277, then following the initial 1 mg subcutaneous dosage, initiation would begin of 60 mg of subcutaneous twice daily optimized Perle peptide modified by blocking (i.e., end-capping of the amino and carboxyl termini of both peptides with acetyl and amide groups), of Perle peptide (eg: SEQ ID: 8). Once every three months, the patient would receive another subcutaneous injection of the heat shock protein Diapep277, during which time, based in glucose levels, exogenous insulin would be tapered as described below. After initiation of the Perle peptide, based in glucose levels, exogenous insulin would be tapered as described below.

If the selected immune tolerance agent selected is the *Mycobacterium bovis Bacillus*-Calmette-Guerin (BCG) vaccine, also known as the tuberculosis vaccine, then two 0.1 ml intradermal injections into the deltoid area containing the low-dose BCG (1.6-3.26106 colony-forming units/injection) administered four weeks apart with the initiation of 60 mg of subcutaneous twice daily optimized Perle peptide, modified by blocking (i.e., end-capping of the amino and carboxyl termini of the selected Perle peptide with acetyl and amide groups), of Perle peptide (SEQ ID: 8). Perle peptides, derivatives, optimized versions, peptidomimetics or stimulatory antibodies to the Reg Receptor may be delivered within 15 minutes of two major meals eaten, when at least 30 grams of carbohydrates are consumed. After initiation of the Perle peptides, derivatives, optimized versions, peptidomimetics or stimulatory antibodies to the Reg Receptor, based upon the individual's glucose levels, exogenous insulin would be tapered as described below.

There will be a four-week period prior to the initial administration of Perle peptides, derivatives, optimized versions, peptidomimetics or stimulatory antibodies to the Reg Receptor, in which the patients should not have any episodes of symptomatic hypoglycemia. Should patients exhibit symptomatic hypoglycemia on beta agonists including Perle peptides, derivatives, optimized versions, peptidomimetics or stimulatory antibodies to the Reg Receptor is administered, the patients' diabetes regimen should be modified because hypoglycemia may negate the effects of beta generation due to numerous counter regulatory hormones that prevent new beta cell formation in the presence of hypoglycemia.

During the period in which beta agonist therapy including Perle peptides, derivatives, optimized versions, peptidomimetics or stimulatory antibodies to the Reg Receptor are administered, the patients' insulin dosage may be decreased as required to prevent any episodes of hypoglycemia and to maintain glucose levels in an optimal range for islet neogenesis and may initially be reduced by 1% per day for the first 30 days. This is a total reduction of 1% per day from the preprandial insulin dosages (0.33% per meal reduction of the total premeal insulin dosage from the previous premeal dosage). During days 31-60 Perle peptides, derivatives, optimized versions, peptidomimetics or stimulatory antibodies to the Reg Receptor, there may be a 1% per day reduction in the basal insulin from the previous day.

During the first about 60 days of therapy with beta agonist therapy including Perle peptides, derivatives, optimized versions, peptidomimetics or stimulatory antibodies to the Reg Receptor, patients will have daily communication via phone, e-mail or office visits to give feedback on glucose values to the diabetes health care team. Based on the glucose values, more aggressive reduction in basal insulin dosages may occur if premeal glucose levels are less than 100 mg/dL and more aggressive reductions in premeal insulin may occur if 2 hour postprandial levels are less than 140 mg/dL.

During about days 61-90 on beta agonist therapy with agents including Perle peptides, derivatives, optimized versions, peptidomimetics or stimulatory antibodies to the Reg Receptor, insulin dosages maybe reduced by 0.5-2.0% per day based upon daily glucose values. Reduction in basal insulin dosages may be required to prevent any episodes of hypoglycemia and to maintain glucose levels in an optimal range for islet neogenesis and may initially be reduced by 0.5% per day if premeal values are 100-125 mg/dL and a 0.6% per day total reduction (0.18% per meal reduction from the previous day) in premeal insulin may occur if 2 hour postprandial levels are 140-160 mg/dl. Each day there may be a 1% reduction in basal insulin if premeal glucose levels are less than 100 mg/dL and 1% reduction (0.33% per meal reduction from the previous day) in premeal insulin may occur if 2 hour postprandial levels are less than 140 mg/dL. If there are episodes of hypoglycemia in the premeal period, there may be a reduction of 2.0% from the previous day in basal insulin from the previous day. If there are any episodes of hypoglycemia during the postprandial phase, the dosage of preprandial insulin may be reduced by 2.0% before meals (0.7% per meal in premeal insulin).

Beta agonists including Perle peptides, derivatives, optimized versions, peptidomimetics or stimulatory antibodies to the Reg Receptor can be discontinued when stimulated C-peptide levels are within the normal range and when optimized glycemic control has been achieved without the usage of other diabetic agents including insulin. Throughout the duration of the treatment patients may have daily communication via phone, e-mail or office visits to give feedback on glucose values to the diabetes health care team. Based on the glucose values, more aggressive reduction in basal and premeal insulin dosages may occur based on premeal and postprandial glucose levels respectively.

Example 5

Methods of Treating New and Existing Type 2 Diabetes, as Well as PreDiabetes and Conditions of Insulin/Beta Cell Deficiency Utilizing Perle Peptides, Derivatives, Optimized Versions, Peptidomimetics or Stimulatory Antibodies to the Reg Receptor In a normally functioning pancreas, small numbers of beta cells die naturally on a day-by-day basis and are replaced as required to keep glucose levels under control. In non-diabetic patients, the beta cell mass within the existing islets can expand or contract depending on the insulin needs of the individual. In patients with 2 diabetes, the beta cell apoptosis exceeds the proliferation of new beta cells. More recent studies have demonstrated that PreDiabetes, insulin resistant states, hypertension, inactivity and family history are islet stressors for depleting beta cell mass.

Despite many new classes of therapies that are now available for type 2 diabetes, which may improve metabolic function and hemoglobin A1C, a normal hemoglobin A1C is 5.5% remains unachievable for most. Stratton I M et al., BMJ. 2000; 321(7258):405-412. As the hemoglobin A1C rises above 5.5%, there is increased risk of complications that rises as well. Very rarely are the available diabetes agents including injectables and oral medications, even when used in combination with one another, able to safely and effectively come close to achieving a hemoglobin A1C of 5.5% among patients with type 2 or PreDiabetes. Providing new beta cells from one own pancreatic progenitor cells to patients with type 2 diabetes, PreDiabetes and other conditions of insulin resistance, insulin insufficiency, beta cell deficiency and associated conditions provides an opportunity reverse this disease state.

It has been shown that that lifestyle modifications and metformin were able to reduce the risk in adults with PreDiabetes from progressing on to the development of diabetes, but lifestyle modifications did not improve hemoglobin A1C or prevent the need for further medical therapy including insulin therapy among children and adolescence with diabetes. The TODAY Study Group., N Engl J Med 2012; 366:2247-2256. Diabetes Research Program Prevention Group, Lancet. 2009; 374(9702): 1677-1686. The TODAY study illustrates the need among all populations of patients with diabetes for new therapies that address the underlying problem in diabetes, which is deficiency of beta cells that secrete insulin. Despite all of the new medications and technologies available for use among patients with diabetes, diabetes remains the leading cause of new blindness, amputations and kidney failure necessitating dialysis. Stimulating new beta cells from one's own pancreatic progenitor cells serves as the best method to reverse type 2 diabetes in adults and children.

Many patients with diabetes and PreDiabetes are currently on one or more agents, which may include a combination of agents, both injectable and oral agents. Perle peptides, formulations, optimized versions, peptidomimetics and stimulating antibodies to a binding region on the Reg receptor will be used as first-line therapy for new onset and existing type 2 diabetes, as well as PreDiabetes. Perle peptides, formulations, optimized versions, peptidomimetics and stimulating antibodies to a binding region on the Reg receptor may be added to other diabetes agents and including: all types of insulin, Glucagon Like Peptide-1 (GLP-1) receptor analogs Liraglutide and Exenatide, Dipeptidyl Peptidase-4 Inhibitors, (DPP-4 inhibitors), and including (Sitagliptin, Saxagliptin, Linagliptin), the Amylin, analog, pramlintide, acarbose, orlistat, colesevelam, bromocriptine, orlistat, combination therapies with the biguanide, metformin, and combinations of with thiazolidinediones, sulfonylureas and DPP-4 inhibitors and new agents SGLT2 inhibitors (dapagliflozin and canagliflozin). The ability to provide patients with type 2 diabetes with new beta cells enables tapering of other medications, including insulin, and is also utilized to prevent the progression of PreDiabetes to type 2 diabetes.

FIG. 15 illustrates a summary of methods to reverse type 2 diabetes utilizing a beta cell agonist including Perle peptides, derivatives, optimized versions, peptidomimetics or stimulatory antibodies to the Reg Receptor. Perle peptides, formulations, optimized versions, peptidomimetics and stimulating antibodies to a binding region on the Reg receptor identified in this invention would be first-line therapy for patients with type 2 diabetes and PreDiabetes or added to existing diabetes medications regimens including insulin. Based upon glucose levels, other diabetes medications, including insulin will be tapered as new beta cells are formed as described below.

These methods provide for a said patient with PreDiabetes who may be treated with metformin n or a patient with type 2 diabetes who may be treated with metformin, insulin and DPP-4 inhibitor, yet the patient maintains a hemoglobin A1C that is above goal and therefore is in need of an agent that addresses the underlying mechanism of causing diabetes, which is beta cell deficiency.

A said patient with PreDiabetes, new onset 2 diabetes or existing type 2 diabetes would undergo a two-week period prior to the initial administration of a beta agonist including Perle peptides, derivatives, optimized versions, peptidomimetics or stimulatory antibodies to the Reg Receptor, in which the patients should closely monitor both pre and postprandial blood glucose levels and not have any episodes of symptomatic hypoglycemia or documentation of glucose levels <70 mg/dL. Should patients exhibit symptomatic hypoglycemia or glucose levels are below 70 mg/dL, diabetic medications should be tapered, and the intensification of glucose levels be reinitiated in order to prevent hypoglycemia, which will inhibit the effects of a beta cell agonist including Perle peptides, derivatives, optimized versions, peptidomimetics or stimulatory antibodies to the Reg Receptor.

Perle peptides, derivatives, optimized versions, peptidomimetics or stimulatory antibodies to the Reg Receptor are added to the patients daily medication regimen in a dosage of 60 mg (1 mg/kg) of subcutaneous twice daily optimized Perle peptide modified by blocking (i.e., end-capping of the amino and carboxyl termini of the selected Perle peptide with acetyl and amide groups), of Perle peptide (SEQ ID: 8). Perle peptides, derivatives, optimized versions, peptidomimetics or stimulatory antibodies to the Reg Receptor may be delivered within 15 minutes of two major meals eaten, when at least 30 grams of carbohydrates are consumed. After initiation of the Perle peptide, based on glucose levels, other agents including exogenous insulin may be tapered as described below.

Once Perle peptides, derivatives, optimized versions, peptidomimetics or stimulatory antibodies to the Reg Receptor are administered, the patients' diabetes regimen should be modified when glucose levels fall below 100 mg/dL because hypoglycemia will negate the effects of beta generation due to numerous counter regulatory hormones that prevent new beta cell formation in the presence of hypoglycemia.

During the period in which Perle peptides, derivatives, optimized versions, peptidomimetics or stimulatory antibodies to the Reg Receptor are administered, the patients' diabetes medications may require tapering of agents beginning with insulin should the patient be on insulin. The insulin dosage may be decreased as required to prevent any episodes of hypoglycemia and to maintain glucose levels in an optimal range for beta cell regeneration and if the patient is on insulin therapy, the insulin dosage may initially be reduced by 1% per day for the first 30 days. For patients on insulin, this is a total reduction of 1% per day from the preprandial insulin dosages (0.33% per meal reduction of the total premeal insulin dosage from the previous premeal dosage). During days 31-60 Perle peptides, derivatives, optimized versions, peptidomimetics or stimulatory antibodies to the Reg Receptor, there may be a 1% per day reduction in the basal insulin from the previous day for patient treated with insulin.

During the first about 60 days of therapy with Perle peptides, derivatives, optimized versions, peptidomimetics or stimulatory antibodies to the Reg Receptor, patients will have daily communication via phone, e-mail or office visits to give feedback on glucose values to the diabetes health care team. Based on the glucose values, more aggressive reduction in or agents, injectable medications or insulin including basal and bolus insulin dosages may occur if premeal glucose levels are less than 100 mg/dL and more aggressive reductions in diabetic agents, which reduce postprandial glucose levels including GLP-receptor analogs, DPP-4 inhibitors, sulfonylureas and premeal insulin if 2 hour postprandial levels are less than 140 mg/dL.

During about days 61-90 on therapy, other agents including oral and injectable agents including insulin may be further tapered based on daily glucose values. Reduction in basal insulin dosages may be required to prevent any episodes of hypoglycemia and to maintain glucose levels in an optimal range for islet neogenesis and may initially be reduced by 0.5% per day if premeal values are 100-125 mg/dL and a 0.6% per day total reduction (0.18% per meal reduction from the previous day) in premeal insulin may occur if 2 hour postprandial levels are 140-160 mg/dl. Each day there may be a 1% reduction in basal insulin if premeal glucose levels are less than 100 mg/dL and 1% reduction (0.33% per meal reduction from the previous day) in premeal insulin may occur if 2 hour postprandial levels are less than 140 mg/dL. If there are episodes of hypoglycemia in the premeal period, there may be a reduction of 2.0% from the previous day in basal insulin from the previous day. If there are any episodes of hypoglycemia during the postprandial phase, the dosage of preprandial insulin may be reduced by 2.0% before meals (0.7% per meal in premeal insulin). When preprandial insulin has been tapered off, other agents acting to reduce postprandial glucose including DPP-4 inhibitors, GLP-1 receptor agonists, meglitinides and sulfonylureas may be tapered. Once insulin has been tapered off, other basal agents including metformin and/or thiazolidinediones may be tapered.

Perle peptides, derivatives, optimized versions, peptidomimetics or stimulatory antibodies to the Reg Receptor can be discontinued when stimulated C-peptide levels are within the normal range and when optimized glycemic control has been achieved without the usage of other diabetic or agents and injectable agents including insulin. Throughout the duration of the treatment patients may have daily communication via phone, e-mail or office visits to give feedback on glucose values to the diabetes health care team. Based on the glucose values, more aggressive reduction in basal and premeal insulin dosages may occur based on premeal and postprandial glucose levels respectively.

Example 6

Ex-Vivo Usage of Perle Peptides, Derivatives, Optimized Versions, Peptidomimetics and Antibodies Generated to Specific Binding Regions of the Perle Receptor Serving as Peptidomimetics for Generation of New Beta Cells from Human Extra-Islet Tissue Including Ductal, Acinar and Progenitor Cells, Human Embryonic Stem Cells, Human Adult Bone-Marrow Derived Cells, Induced Pluripotent Stem Cells, Mesenchymal Stem Cells, Umbilical Cord Stem Cells, or Other Stem Cells and May Include Resident Populations of Endogenous Stem Cells that Exist within the Adult Pancreas that are then Delivered to Patients with Diabetes and Other Conditions of Insulin Deficiency Via the Umbilical Vein, Portal Venous Systemic, Hepatic Aortic Artery, Subcutaneous Delivery with and without Organ Specific Targeting and May Include Direct Administration to the Pancreas or Liver This invention includes methods for the formation and delivery of new beta cells generated by Perle peptides, derivatives, optimized versions, peptidomimetics and antibodies generated to specific binding regions of the Perle Receptor serving as peptidomimetics when utilized for the ex-vivo generation of new beta cells from progenitor cells, which may include, but are not limited to human extra-islet tissue inclusive of ductal, acinar and progenitor embryonic tissue, human stem cells, human adult bone-marrow derived cells, induced pluripotent stem cells, mesenchymal stem cells, umbilical cord stem cells, or other stem cells and may include resident populations of endogenous stem cells that exist within the adult pancreas that are facilitated to transform into beta cells by the addition of Perle peptides, derivatives, optimized versions, peptidomimetics and antibodies generated to specific binding regions of the Perle Receptor serving as peptidomimetics. New beta cells are generated ex-vivo transformation using the inventions herein into new beta cells from Perle peptides, derivatives, optimized versions, peptidomimetics and antibodies generated to specific binding regions of the Perle Receptor serving as peptidomimetics. New beta cells are then delivered to patients with PreDiabetes, type 1 and 2 diabetes and other conditions of beta cell deficiency with routes of delivery to include, but are not limited to oral, intravenous, including delivery via the umbilical vein, portal venous systemic, hepatic aortic artery, subcutaneous delivery with and without organ specific targeting and may include direct administration to the pancreas or liver (FIG. 16).

Perle peptides, derivatives, optimized versions, peptidomimetics and antibodies generated to specific binding regions of the Perle Receptor serving as peptidomimetics are then administered ex-vivo to human extra-islet tissue, inclusive of ductal, acinar and progenitor tissue, embryonic stem cells, human adult bone-marrow derived cells, induced pluripotent stem cells, mesenchymal stem cells, umbilical cord stem cells, or other stem cells and may include resident populations of endogenous stem cells that exist within the adult pancreas to form new beta cells. The new beta cells are generated by the delivery of Perle peptides, derivatives, optimized versions, peptidomimetics and antibodies generated to specific binding regions of the Perle Receptor to ex-vivo cultures of human embryonic stem cells, human adult bone-marrow derived cells, induced pluripotent stem cells, mesenchymal stem cells, umbilical cord stem cells, or other stem cells and may include resident populations of endogenous stem cells that exist within the adult pancreas, accelerate the formation of new beta cells. These beta cells are then delivered to patients with PreDiabetes, type 1 and 2 diabetes and other conditions of beta cell deficiency with routes of delivery to include, but are not limited to oral, intravenous, including delivery via the umbilical vein, portal venous systemic, hepatic aortic artery, subcutaneous delivery with and without organ specific targeting and may include direct administration to the pancreas or liver.

This invention includes methods for pancreatic beta cell generation and include both in vivo and ex-vivo beta cell generation and methods for treating new onset and previously existing type 1 and 2 diabetes, Latent Autoimmune Diabetes of Adulthood (LADA), those at risk for type 1 diabetes, including but not limited to those with positive autoimmune antibodies markers including who are Glutamic Acid Decarboxylase-65 antibody, those with PreDiabetes and diseases of hyperglycemia, glucose intolerance and beta cell impairment or deficiency, insulin resistance, associated conditions including, obesity, obesity prior to the development of diabetes, obesity in children leading to PreDiabetes, both type 1 and type 2 diabetes in childhood and adolescence and include, but are not limited to conditions such as polycystic ovarian syndrome, nonalcoholic steatohepatitis, hyperlipidemia and hypertriglyceridemia and other conditions related to the deficiency or lack of effective amounts of insulin.

One study is designed to demonstrate a Dose Response Comparison of $2^{nd}$ trimester, human fetal pancreatic tissue culture, mesenchymal stem cells to detect and measure the impact of Perle peptides derivatives, formulation, optimized versions and Perle peptide peptidomimetic includes stimulatory antibodies to the Perle Receptor any islet neogenesis over and above placebo. Evaluation of the islet clusters inclusive of beta cells will be obtained by partial enzymatic digestion of the pancreatic tissue and these will be cultured in the presence or absence of Perle peptides derivatives, formulation, optimized versions and Perle peptide peptidomimetic includes stimulatory antibodies to the Perle Receptor for 3 days. Then islet clusters containing beta cells are fixed in formalin and embedded in a paraffin block prior to histological sectioning and immunohistochemical staining for the hormones insulin, glucagon, somatostatin and pancreatic polypeptide, as well as the pancreatic duct marker CK19. Percentages of cells positive for each and CK19 will be counted. A minimum of 6 separate replicates will be determined.

In another study, a Dose Response Comparison between Placebo and Perle peptides derivatives, formulation, optimized versions and Perle peptide peptidomimetic includes stimulatory antibodies to the Perle Receptor in $2^{nd}$ trimester, human fetal pancreatic tissue transplanted into normoglycemic immunodeficient mice to detect and measure any islet neogenesis and beta cells general when Perle peptides derivatives, formulation, optimized versions and Perle peptide peptidomimetic includes stimulatory antibodies to the Perle Receptor are given ex-vivo and compared to placebo.

Human fetal pancreatic tissue will be obtained from the therapeutic termination of pregnancies between 13 and 20 weeks gestation. Islet-like cell clusters containing beta cells will be obtained by partial enzymatic digestion of the pancreatic tissue and these will be cultured for 3 days. Next, islet clusters inclusive of beta cells will be transplanted beneath the renal capsule of NOD/SCID mice, and the mice injected daily or a placebo. A minimum of 6 mice will be will be used in each group. Four weeks, after the islet-like cell clusters containing beta cells are transplanted, the mice will be euthanased and grafts removed for analysis. They will be fixed in formalin and embedded in a paraffin block prior to histological sectioning and immunohistochemical staining for the hormones insulin, glucagon, somatostatin and pancreatic polypeptide, as well as the pancreatic duct marker CK19. Percentages of cells positive for each hormone and CK19 will be counted with comparisons between Perle peptide peptidomimetic includes stimulatory antibodies to the Perle Receptor are given ex-vivo and compared to placebo. Dose Response Comparison of Perle peptides derivatives, formulation, optimized versions and Perle peptide peptidomimetic includes stimulatory antibodies to the Perle Receptor vs. placebo will be evaluated in $2^{nd}$ trimester, human fetal pancreatic tissue transplanted into diabetic immunodeficient mice. The impact of a various dosages of Perle peptide peptidomimetic includes stimulatory antibodies to the Perle Receptor will be given ex-vivo and compared to placebo to detect and measure islet neogenesis and beta cell generation over and above placebo.

Additional Embodiments

Embodiment 1w

An isolated peptide comprising an amino acid sequence that is a partial sequence of the amino acid sequence of a Regenerating islet-derived (Reg) protein, wherein the peptide has Reg receptor binding activity and consists of an amino acid sequence that is not a partial sequence of SEQ ID NO:11 or SEQ ID NO:12.

Embodiment 2w

The isolated peptide of embodiment 1w, wherein the amino acid sequence that is a partial sequence of the amino acid sequence of a Regenerating islet-derived (Reg) protein is a partial sequence of the amino acid sequence of human, chimpanzee, cow, sheep, or mouse Reg protein.

Embodiment 3w

The isolated peptide of embodiment 1w, wherein the amino acid sequence that is a partial sequence of the amino acid sequence of a Regenerating islet-derived (Reg) protein is a partial sequence of the amino acid sequence of human Reg protein.

Embodiment 4w

The isolated peptide of embodiment 3w, wherein the amino acid sequence that is a partial sequence of the amino acid sequence of a human Reg protein is a partial sequence of SEQ ID NO: 2, SEQ ID NO: 3, SEQ ID NO: 5, or SEQ ID NO:10.

Embodiment 5w

The isolated peptide of any of embodiments 1w-4w, that is 7-9 amino acids in length.

Embodiment 6w

The isolated peptide of embodiment 1w, wherein the amino acid sequence that is a partial sequence of the amino acid sequence of a Regenerating islet-derived (Reg) protein is at least 70% identical to SEQ ID NO: 1, SEQ ID NO: 4, SEQ ID NO: 7, SEQ ID NO: 8, or SEQ ID NO: 14.

Embodiment 7w

The isolated peptide of embodiment 1w, wherein the amino acid sequence that is a partial sequence of the amino acid sequence of a Regenerating islet-derived (Reg) protein is at least 75% identical to SEQ ID NO: 1, SEQ ID NO: 4, SEQ ID NO: 7, SEQ ID NO: 8, or SEQ ID NO: 14.

Embodiment 8w

The isolated peptide of embodiment 1w, wherein the amino acid sequence that is a partial sequence of the amino acid sequence of a Regenerating islet-derived (Reg) protein is at least 80% identical to SEQ ID NO: 1, SEQ ID NO: 4, SEQ ID NO: 7, SEQ ID NO: 8, or SEQ ID NO: 14.

Embodiment 9w

The isolated peptide of embodiment 1w, wherein the amino acid sequence that is a partial sequence of the amino acid sequence of a Regenerating islet-derived (Reg) protein is at least 85% identical to SEQ ID NO: 1, SEQ ID NO: 4, SEQ ID NO: 7, SEQ ID NO: 8, or SEQ ID NO: 14.

Embodiment 10w

The isolated peptide of embodiment 1w, wherein the amino acid sequence that is a partial sequence of the amino acid sequence of a Regenerating islet-derived (Reg) protein is SEQ ID NO: 1, SEQ ID NO: 4, SEQ ID NO: 7, SEQ ID NO: 8, or SEQ ID NO: 14.

Embodiment 11w

The isolated peptide of embodiment 1w, wherein the amino acid sequence that is a partial sequence of the amino acid sequence of a Regenerating islet-derived (Reg) protein is a partial sequence of SEQ ID NO: 1, SEQ ID NO: 4, SEQ ID NO: 7, SEQ ID NO: 8, or SEQ ID NO: 14.

Embodiment 12w

An isolated peptide comprising an amino acid sequence that is at least 70% identical to SEQ ID NO: 1, SEQ ID NO: 4, SEQ ID NO: 7, SEQ ID NO: 8, or SEQ ID NO: 14, wherein the peptide has Reg receptor binding activity.

Embodiment 13w

An isolated peptide comprising an amino acid sequence that is at least 75% identical to SEQ ID NO: 1, SEQ ID NO: 4, SEQ ID NO: 7, SEQ ID NO: 8, or SEQ ID NO: 14, wherein the peptide has Reg receptor binding activity.

Embodiment 14w

An isolated peptide comprising an amino acid sequence that is at least 80% identical to SEQ ID NO: 1, SEQ ID NO: 4, SEQ ID NO: 7, SEQ ID NO: 8, or SEQ ID NO: 14, wherein the peptide has Reg receptor binding activity.

Embodiment 15w

An isolated peptide comprising an amino acid sequence that is at least 85% identical to SEQ ID NO: 1, SEQ ID NO: 4, SEQ ID NO: 7, SEQ ID NO: 8, or SEQ ID NO: 14, wherein the peptide has Reg receptor binding activity.

Embodiment 16w

An isolated peptide comprising an amino acid sequence that is a partial sequence of SEQ ID NO: 1, SEQ ID NO: 4, SEQ ID NO: 7, SEQ ID NO: 8, or SEQ ID NO: 14, wherein the peptide has Reg receptor binding activity.

Embodiment 17w

An isolated fusion polypeptide comprising at least two peptides wherein each peptide comprises an amino acid sequence that is at least 70% identical to SEQ ID NO: 1, SEQ ID NO: 4, SEQ ID NO: 7, SEQ ID NO: 8, or SEQ ID NO: 14.

Embodiment 18w

The isolated peptide of embodiments 1w or 12w, wherein the peptide is a peptidomimetic.

Embodiment 19w

The isolated peptide of embodiments 1w or 12w, wherein the peptide has been modified to increase stability, increase solubility, increase protease resistance, reduce immunogenicity, increase Tmax, or increase bioavailability.

Embodiment 20w

The isolated peptide of embodiment 19w, wherein the peptide is blocked with a c-terminal acetyl group and n-terminal amide group.

Embodiment 21w

The isolated peptide of embodiment 19w, wherein the peptide includes a cysteine residue added to the n-terminal.

Embodiment 22w

The isolated peptide of embodiment 19w, wherein the peptide is modified by cyclization.

Embodiment 23w

The isolated peptide of embodiment 19w, wherein the peptide is modified by pegylation.

Embodiment 24w

A pharmaceutical formulation comprising the isolated peptide of embodiment 19w.

Embodiment 25w

The pharmaceutical formulation of embodiment 24w, wherein the formulation is optimized for oral, intravenous, or subcutaneous delivery.

Embodiment 26w

The pharmaceutical formulation of embodiment 24w, that is a unit dose form.

Embodiment 27w

The pharmaceutical formulation of embodiment 24w, further comprising one or more other active pharmaceutical ingredients (APIs).

Embodiment 28w

The pharmaceutical formulation of embodiment 27w, wherein the API is an agent in a soluble liposome preparation.

Embodiment 29w

The pharmaceutical formulation of embodiment 28w, wherein the liposome preparation allows the peptide to be administered subcutaneously, intramuscularly, intravenously, intra-arterially, or orally.

Embodiment 30w

The pharmaceutical formulation of embodiment 28w, wherein the formulation is optimized for systemic administration.

Embodiment 31w

The pharmaceutical formulation of embodiment 28w, wherein the formulation includes a targeting agent for targeted administration.

Embodiment 32w

A kit comprising a therapeutically effective dose of the peptide of embodiments 1w or 12w.

Embodiment 33w

An isolated polynucleotide comprising a nucleotide sequence encoding the peptide of embodiments 1w or 12w.

Embodiment 34w

A vector comprising the polynucleotide of embodiment 33w.

Embodiment 35w

A host cell comprising the polynucleotide of embodiment 33w.

Embodiment 36w

The host cell of embodiment 35w, wherein the host cell is a stem cell.

Embodiment 1x

An isolated antibody that specifically binds a peptide sequence of the human Reg Receptor (SEQ ID NO: 6).

Embodiment 2x

The antibody of embodiment 1x, wherein the antibody specifically binds a peptide sequence consisting of the amino acid sequence of SEQ ID NO: 9.

Embodiment 3x

The antibody of embodiment 2x, wherein the antibody specifically binds a peptide sequence that is contained within the amino acid sequence of SEQ ID NO: 9.

Embodiment 4x

The antibody of embodiment 1x, wherein the antibody stimulates beta cell production.

Embodiment 5x

The antibody of embodiment 1x, wherein the antibody is polyclonal.

Embodiment 6x

The antibody of embodiment 1x, wherein the antibody is monoclonal.

Embodiment 7x

The antibody of embodiment 1x, wherein the antibody is human.

Embodiment 8x

The antibody of embodiment 1x, wherein the antibody is humanized.

Embodiment 9x

The antibody of embodiment 2x, wherein the antibody stimulates beta cell production.

Embodiment 10x

The antibody of embodiment 2x, wherein the antibody is polyclonal.

Embodiment 11x

The antibody of embodiment 2x, wherein the antibody is monoclonal.

Embodiment 12x

The antibody of embodiment 2x, wherein the antibody is human.

Embodiment 13x

The antibody of embodiment 2x, wherein the antibody is humanized.

Embodiment 14x

The antibody of embodiment 3x, wherein the antibody stimulates beta cell production.

Embodiment 15x

The antibody of embodiment 3x, wherein the antibody is polyclonal.

Embodiment 16x

The antibody of embodiment 3x, wherein the antibody is monoclonal.

Embodiment 17x

The antibody of embodiment 3x, wherein the antibody is human.

Embodiment 18x

The antibody of embodiment 3x, wherein the antibody is humanized.

Embodiment 19x

A method for screening antigens for the production of antibodies to the Reg Receptor, comprising:
a. injecting rabbits with a screening antigen comprising a peptide comprising an amino acid sequence that is contained within the N-terminal portion of the putative Reg Receptor (SEQ ID NO:13), plus an adjuvant;
b. obtaining a serum sample from said rabbits; and
c. measuring antibodies in said sample through an ELISA titre assay to measure the response to the antigen.

Embodiment 20x

The method of embodiment 19x, wherein the peptide comprises the amino acid sequence of SEQ ID NO: 9.

Embodiment 21x

The method of embodiment 19x, wherein the peptide comprises an amino acid sequence that is contained within the amino acid sequence of SEQ ID NO: 9.

Embodiment 22x

A kit comprising the antibody of embodiments 1x-3x.

Embodiment 1y

A method of treating a condition that is associated with or is a risk factor for impaired glucose homeostasis selected from new onset type 1 and 2 diabetes, previously existing type 1 and 2 diabetes, latent autoimmune diabetes of adulthood (LADA), glutamic acid decarboxylase-65 autoimmunity, prediabetes, hyperglycemia, glucose intolerance, beta cell impairment or deficiency, insulin resistance, obesity, polycystic ovarian syndrome, nonalcoholic steatohepatitis, hyperlipidemia, and hypertriglyceridemia, comprising the step of:
administering to the subject a therapeutically effective amount of an agent that has Reg receptor binding activity.

Embodiment 2y

The method of embodiment 1y, wherein the agent is a peptide.

Embodiment 3y

The method of embodiment 1y, wherein the agent is a fusion polypeptide comprising at least two peptides.

Embodiment 4y

The method of embodiment 1y, wherein the agent is a stimulatory antibody.

Embodiment 5y

The method of embodiment 1y, wherein the agent is a small molecule.

Embodiment 6y

The method of embodiment 2y, wherein the peptide comprises an amino acid sequence that is at least 70% identical to SEQ ID NO: 1, SEQ ID NO: 4, SEQ ID NO: 7, SEQ ID NO: 8, or SEQ ID NO: 14.

Embodiment 7y

The method of embodiment 3y, wherein each peptide of the fusion protein comprises an amino acid sequence that is at least 70% identical to SEQ ID NO: 1, SEQ ID NO: 4, SEQ ID NO: 7, SEQ ID NO: 8, or SEQ ID NO: 14.

Embodiment 8y

The method of embodiment 1y, wherein the condition is associated with autoimmunity and an immune modulator is administered before and/or in parallel with the administration of the therapeutically effective amount of the agent that has Reg receptor binding activity.

Embodiment 9y

The method of embodiment 8y, wherein the immune modulator is administered at repeat dosages for the protection of newly-formed beta cells.

Embodiment 10y

The method of embodiment 8y, wherein the agent that has Reg receptor binding activity is administered on the day of the immune nadir of the tolerance agent.

Embodiment 11y

The method of embodiment 8y, wherein the immune modulator is a general immunosuppressant agent or an antibody targeted to lymphocytes.

Embodiment 12y

The method of embodiment 8y, wherein the immune modulator is Cyclosporine, an Anti CD-3 antibody including hOKT3γ1(Ala-Ala) and ChAglyCD3; Sirolimus (Rapamycin); Tacrolimus (FK506); Etanercept; Alefacept; Belatacept; a heat-shock protein 60 (Diapep277); a tuberculosis vaccine; Glutamic Acid Decarboxylase 65 (GAD65) vaccine; the BCG tuberculosis vaccine also known as *Bacillus* Calmette-Guërin or Bacille Calmette-Guërin/BCG Vaccine; Mycophenolate Mofetil alone or in combination with Daclizumab; the anti-CD20 agent, Rituximab; Campath-1H (Anti-CD52 Antibody); lysofylline; antithymocyte globulin (ATG); Proleukin or the combination of Proleukin and Rapamune; Vitamin D (Vitamin D2, D3, 1.25 dihydroxy D and other Vitamin D preparations); IBC-VSO vaccine; Ex vivo Expanded Human Autologous CD4+CD127lo/-CD25+ Polyclonal Regulatory T Cells; interferon-alpha; a vaccine using CD4+CD25+ antigen-specific regulatory T cells; Interleukin-1 Receptor Antagonist (anakinra); or Alpha 1-Antitrypsin.

Embodiment 13y

The method of embodiment 1y, wherein a period of glucose control is optimized before the administration of the therapeutically effective amount of an agent that has Reg receptor binding activity.

Embodiment 14y

The method of embodiment 13y, wherein the glucose control is optimized for glucose levels of between 100 to 200 mg/dl.

Embodiment 15y

The method of embodiment 13y, wherein the glucose control is optimized to prevent glucose levels from falling below 70 mg/dl.

Embodiment 16y

The method of embodiment 13y, wherein the period of glucose control is at least 4 weeks.

Embodiment 17y

The method of embodiment 1y, wherein the patient's insulin dose is decreased based on glucose levels to prevent an episode of hypoglycemia and to maintain glucose levels in an optimal range for islet neogenesis.

Embodiment 18y

The method of embodiment 1y, wherein the agent that has Reg receptor binding activity is administered through oral, intravenous, intra-arterial, or subcutaneous delivery.

Embodiment 19y

The method of embodiment 1y, wherein the agent that has Reg receptor binding activity is administered directly to the pancreas or the liver.

Embodiment 20y

The method of embodiment 1y, wherein the agent that has Reg receptor binding activity is administered in combination with another diabetic agent.

Embodiment 21y

The method of embodiment 20y, wherein the other diabetic agent is a form of insulin, Liraglutide, Exenatide, Sitagliptin, Saxagliptin, Linagliptin, pramlintide, acarbose, orlistat, colesevelam, bromocriptine, orlistat, biguanide, metformin, dapagliflozin, canagliflozin, a sulfonylurea, a meglitinide, a GLP-1 receptor analog, a DPP-4 inhibitor, a thiazolidinedione, an SGLT2 inhibitor, an anti-inflammatory agent, or Vitamin D.

Embodiment 22y

The method of embodiment 20y, wherein the other diabetic agent is tapered off or reduced based on daily glucose values.

Embodiment 23y

The method of embodiment 22y, wherein the other diabetic agent is insulin and is reduced by about 0.5-2.0% per day.

Embodiment 24y

The method of embodiment 1y, wherein the subject is diabetes-drug naïve.

Embodiment 25y

The method of embodiment 1y, wherein the agent is administered at intervals to maintain a minimum number of beta cells for normal glucose metabolism.

Embodiment 26y

The method of embodiment 2y, wherein the peptide comprises an amino acid sequence that is a partial sequence of SEQ ID NO: 1, SEQ ID NO: 4, SEQ ID NO: 7, SEQ ID NO: 8, or SEQ ID NO: 14.

Embodiment 1z

A method for the generation of new beta cells from progenitor cells, comprising the steps of:
a. culturing progenitor cells ex vivo; and
b. contacting said progenitor cells with an agent that has Reg receptor binding activity, wherein the amount of agent is effective for forming beta cells from said progenitor cells.

Embodiment 2z

The method of embodiment 1z, wherein the agent is a peptide.

Embodiment 3z

The method of embodiment 1z, wherein the agent is a fusion polypeptide comprising at least two peptides.

Embodiment 4z

The method of embodiment 1z, wherein the agent is a stimulatory antibody.

Embodiment 5z

The method of embodiment 1z, wherein the agent is a small molecule.

Embodiment 6z

The method of embodiment 2z, wherein the peptide comprises an amino acid sequence that is at least 70% identical to SEQ ID NO: 1, SEQ ID NO: 4, SEQ ID NO: 7, SEQ ID NO: 8, or SEQ ID NO: 14.

Embodiment 7z

The method of embodiment 3z, wherein each peptide of the fusion protein comprises an amino acid sequence that is at least 70% identical to SEQ ID NO: 1, SEQ ID NO: 4, SEQ ID NO: 7, SEQ ID NO: 8, or SEQ ID NO: 14.

Embodiment 8z

The method of embodiment 1z, wherein the progenitor cells are derived from human extra-islet tissue inclusive of ductal, acinar, and progenitor embryonic tissue.

Embodiment 9z

The method of embodiment 1z, wherein the progenitor cells are embryonic cells, adult somatic stem cells, human adult bone-marrow derived cells, pluripotent stem cells, mesenchymal stem cells, umbilical cord stem cells, human amniotic membrane-derived mesenchymal cells, mammalian stem cells, or ectodermal stem cells.

Embodiment 10z

A method of treating a condition that is associated with or is a risk factor for impaired glucose homeostasis selected from new onset type 1 and 2 diabetes, previously existing type 1 and 2 diabetes, latent autoimmune diabetes of adulthood (LADA), glutamic acid decarboxylase-65 autoimmunity, prediabetes, hyperglycemia, glucose intolerance, beta cell impairment or deficiency, insulin resistance, obesity, polycystic ovarian syndrome, nonalcoholic steatohepatitis, hyperlipidemia, and hypertriglyceridemia, comprising the steps of:
  a. culturing progenitor cells ex vivo;
  b. contacting said progenitor cells with an agent that has Reg receptor binding activity, wherein the amount of agent is effective for forming beta cells from said progenitor cells;
  c. administering said beta cells to the patient.

Embodiment 11z

The method of embodiment 10z, wherein the agent is a peptide.

Embodiment 12z

The method of embodiment 10z, wherein the agent is a fusion polypeptide comprising at least two peptides.

Embodiment 13z

The method of embodiment 10z, wherein the agent is a stimulatory antibody.

Embodiment 14z

The method of embodiment 10z, wherein the agent is a small molecule.

Embodiment 15z

The method of embodiment 11z, wherein the peptide comprises an amino acid sequence that is at least 70% identical to SEQ ID NO: 1, SEQ ID NO: 4, SEQ ID NO: 7, SEQ ID NO: 8, or SEQ ID NO: 14.

Embodiment 16z

The method of embodiment 12z, wherein each peptide of the fusion protein comprises an amino acid sequence that is at least 70% identical to SEQ ID NO: 1, SEQ ID NO: 4, SEQ ID NO: 7, SEQ ID NO: 8, or SEQ ID NO: 14.

Embodiment 17z

The method of embodiment 10z, wherein the progenitor cells are derived from human extra-islet tissue inclusive of ductal, acinar, and progenitor embryonic tissue.

Embodiment 18z

The method of embodiment 10z, wherein the progenitor cells are embryonic cells, adult somatic stem cells, human adult bone-marrow derived cells, pluripotent stem cells, mesenchymal stem cells, umbilical cord stem cells, human amniotic membrane-derived mesenchymal cells, mammalian stem cells, or ectodermal stem cells.

Embodiment 19z

The method of embodiment 10z, wherein the beta cells are administered to the subject through an oral, intravenous, subcutaneous, or intra-arterial route of administration.

Embodiment 20z

The method of embodiment 10z, wherein the beta cells are delivered through the umbilical vein, portal vein, or hepatic artery.

Embodiment 21z

The method of embodiment 10z, wherein the beta cells are delivered directly to the pancreas or the liver.

Embodiment 22z

The method of embodiment 10z, wherein the condition is associated with autoimmunity and an immune modulator is administered before and/or in parallel with the administration of the beta cells

Embodiment 23z

The method of embodiment 22z, wherein the immune modulator is a general immunosuppressant agent or an antibody targeted to lymphocytes.

Embodiment 24z

The method of embodiment 22z, wherein the immune modulator is Cyclosporine, an Anti CD-3 antibody including hOKT3γ1(Ala-Ala) and ChAglyCD3; Sirolimus (Rapamycin); Tacrolimus (FK506); Etanercept; Alefacept; Belatacept; a heat-shock protein 60 (Diapep277); a tuberculosis vaccine; Glutamic Acid Decarboxylase 65 (GAD65) vaccine; the BCG tuberculosis vaccine also known as *Bacillus* Calmette-Guërin or Bacille Calmette-Guërin/BCG Vaccine; Mycophenolate Mofetil alone or in combination with Daclizumab; the anti-CD20 agent, Rituximab; Campath-1H (Anti-CD52 Antibody); lysofylline; antithymocyte globulin (ATG); Proleukin or the combination of Proleukin and Rapamune; Vitamin D (Vitamin D2, D3, 1.25 dihydroxy D and other Vitamin D preparations); IBC-VSO vaccine; Ex vivo Expanded Human Autologous CD4+CD127lo/-CD25+ Polyclonal Regulatory T Cells; interferon-alpha; a vaccine using CD4+CD25+ antigen-specific regulatory T cells; Interleukin-1 Receptor Antagonist (anakinra); or Alpha 1-Antitrypsin.

Embodiment 25z

The method of embodiment 2z, wherein the peptide comprises an amino acid sequence that is a partial sequence of SEQ ID NO: 1, SEQ ID NO: 4, SEQ ID NO: 7, SEQ ID NO: 8, or SEQ ID NO: 14.

Embodiment 26z

The method of embodiment 11z, wherein the peptide comprises an amino acid sequence that is a partial sequence of SEQ ID NO: 1, SEQ ID NO: 4, SEQ ID NO: 7, SEQ ID NO: 8, or SEQ ID NO: 14.

I claim:

1. An isolated peptide consisting of an amino acid sequence selected from the group consisting of NVWIGLHDP (SEQ ID NO:1), VWIGLHDP (SEQ ID NO:4), and WIGLHDP (SEQ ID NO:7), wherein the peptide has been modified to increase stability, increase solubility, increase protease resistance, reduce immunogenicity, increase Tmax, or increase bioavailability.

2. The isolated peptide of claim 1, wherein the peptide is blocked with a c-terminal acetyl group and n-terminal amide group.

3. The isolated peptide of claim 1, wherein the peptide includes a cysteine residue added to the n-terminal.

4. The isolated peptide of claim 1, wherein the peptide is modified by cyclization.

5. The isolated peptide of claim 1, wherein the peptide is modified by pegylation.

6. A pharmaceutical formulation comprising the isolated peptide of claim 1.

7. The pharmaceutical formulation of claim 6, wherein the formulation is optimized for oral, intravenous, or subcutaneous delivery.

8. The pharmaceutical formulation of claim 6, that is a unit dose form.

9. The pharmaceutical formulation of claim 6, further comprising one or more other active pharmaceutical ingredients (APIs).

10. The pharmaceutical formulation of claim 9, wherein the API is an agent in a soluble liposome preparation.

11. The pharmaceutical formulation of claim 10, wherein the liposome preparation allows the peptide to be administered subcutaneously, intramuscularly, intravenously, intraarterially, or orally.

12. The pharmaceutical formulation of claim 10, wherein the formulation is optimized for systemic administration.

13. The pharmaceutical formulation of claim 10, wherein the formulation includes a targeting agent for targeted administration.

* * * * *

UNITED STATES PATENT AND TRADEMARK OFFICE
CERTIFICATE OF CORRECTION

PATENT NO.       : 8,911,776 B2
APPLICATION NO.  : 13/662209
DATED            : December 16, 2014
INVENTOR(S)      : Claresa Levetan It is certified that error appears in the above-identified patent and that said Letters Patent is hereby corrected as shown below:

In the specification

The text at column 10 at lines 25-26 reads:

"1) blocking with a c-terminal acetyl groups and an n-terminal amide groups,"

It should read:

"1) blocking with a c-terminal amide groups and an n-terminal acetyl groups,"

The text at column 10 at lines 46-48 reads:

"include blocking the peptide by the addition of an n-terminal amide group and a c-terminal acetyl group,"

It should read:

"include blocking the peptide by the addition of an n-terminal acetyl group and a c-terminal amide group,"

The text at column 54 at lines 39-41 reads:

"The isolated peptide of embodiment 19w, wherein the pep-tide is blocked with a c-terminal acetyl group and n-terminal amide group."

It should read:

"The isolated peptide of embodiment 19w, wherein the pep-tide is blocked with a c-terminal amide group and n-terminal acetyl group."

Signed and Sealed this
Fifth Day of July, 2016

Michelle K. Lee
*Director of the United States Patent and Trademark Office*

CERTIFICATE OF CORRECTION (continued)
U.S. Pat. No. 8,911,776 B2

In the claims

Please, replace claim 2 (column 75, lines 52-54) with the following:

> THE ISOLATED PEPTIDE OF CLAIM 1, WHEREIN THE PEPTIDE IS BLOCKED WITH A C-TERMINAL AMIDE GROUP AND AN N-TERMINAL ACETYL GROUP.

SEQUENCE LISTING

```
<160> NUMBER OF SEQ ID NOS: 14

<210> SEQ ID NO 1
<211> LENGTH: 9
<212> TYPE: PRT
<213> ORGANISM: Homo sapiens

<400> SEQUENCE: 1

Asn Val Trp Ile Gly Leu His Asp Pro
1               5

<210> SEQ ID NO 2
<211> LENGTH: 166
<212> TYPE: PRT
<213> ORGANISM: Homo sapiens

<400> SEQUENCE: 2

Met Ala Gln Thr Ser Ser Tyr Phe Met Leu Ile Ser Cys Leu Met Phe
1               5                   10                  15

Leu Ser Gln Ser Gln Gly Gln Glu Ala Gln Thr Glu Leu Pro Gln Ala
                20                  25                  30

Arg Ile Ser Cys Pro Glu Gly Thr Asn Ala Tyr Arg Ser Tyr Cys Tyr
            35                  40                  45

Tyr Phe Asn Glu Asp Arg Glu Thr Trp Val Asp Ala Asp Leu Tyr Cys
        50                  55                  60

Gln Asn Met Asn Ser Gly Asn Leu Val Ser Val Leu Thr Gln Ala Glu
65                  70                  75                  80

Gly Ala Phe Val Ala Ser Leu Ile Lys Glu Ser Gly Thr Asp Asp Phe
                85                  90                  95

Asn Val Trp Ile Gly Leu His Asp Pro Lys Lys Asn Arg Arg Trp His
                100                 105                 110

Trp Ser Ser Gly Ser Leu Val Ser Tyr Lys Ser Trp Gly Ile Gly Ala
            115                 120                 125

Pro Ser Ser Val Asn Pro Gly Tyr Cys Val Ser Leu Thr Ser Ser Thr
        130                 135                 140

Gly Phe Gln Lys Trp Lys Asp Val Pro Cys Glu Asp Lys Phe Ser Phe
145                 150                 155                 160

Val Cys Lys Phe Lys Asn
                165

<210> SEQ ID NO 3
<211> LENGTH: 166
<212> TYPE: PRT
<213> ORGANISM: Homo sapiens

<400> SEQUENCE: 3

Met Ala Gln Thr Asn Ser Phe Phe Met Leu Ile Ser Ser Leu Met Phe
```

```
1               5                   10                  15
Leu Ser Leu Ser Gln Gly Gln Glu Ser Gln Thr Glu Leu Pro Asn Pro
                20                  25                  30

Arg Ile Ser Cys Pro Glu Gly Thr Asn Ala Tyr Arg Ser Tyr Cys Tyr
                35                  40                  45

Tyr Phe Asn Glu Asp Pro Glu Thr Trp Val Asp Ala Asp Leu Tyr Cys
    50                  55                  60

Gln Asn Met Asn Ser Gly Asn Leu Val Ser Val Leu Thr Gln Ala Glu
65                  70                  75                  80

Gly Ala Phe Val Ala Ser Leu Ile Lys Glu Ser Ser Thr Asp Asp Ser
                85                  90                  95

Asn Val Trp Ile Gly Leu His Asp Pro Lys Lys Asn Arg Arg Trp His
                100                 105                 110

Trp Ser Ser Gly Ser Leu Val Ser Tyr Lys Ser Trp Asp Thr Gly Ser
                115                 120                 125

Pro Ser Ser Ala Asn Ala Gly Tyr Cys Ala Ser Leu Thr Ser Cys Ser
130                 135                 140

Gly Phe Lys Lys Trp Lys Asp Glu Ser Cys Glu Lys Lys Phe Ser Phe
145                 150                 155                 160

Val Cys Lys Phe Lys Asn
                165

<210> SEQ ID NO 4
<211> LENGTH: 8
<212> TYPE: PRT
<213> ORGANISM: Homo sapiens

<400> SEQUENCE: 4

Val Trp Ile Gly Leu His Asp Pro
1               5

<210> SEQ ID NO 5
<211> LENGTH: 175
<212> TYPE: PRT
<213> ORGANISM: Homo sapiens

<400> SEQUENCE: 5

Met Leu Pro Pro Met Ala Leu Pro Ser Val Ser Trp Met Leu Leu Ser
1               5                   10                  15

Cys Leu Met Leu Leu Ser Gln Val Gln Gly Glu Pro Gln Arg Glu
                20                  25                  30

Leu Pro Ser Ala Arg Ile Arg Cys Pro Lys Gly Ser Lys Ala Tyr Gly
                35                  40                  45

Ser His Cys Tyr Ala Leu Phe Leu Ser Pro Lys Ser Trp Thr Asp Ala
    50                  55                  60

Asp Leu Ala Cys Gln Lys Arg Pro Ser Gly Asn Leu Val Ser Val Leu
65                  70                  75                  80

Ser Gly Ala Glu Gly Ser Phe Val Ser Ser Leu Val Lys Ser Ile Gly
                85                  90                  95

Asn Ser Tyr Ser Tyr Val Trp Ile Gly Leu His Asp Pro Thr Gln Gly
                100                 105                 110

Thr Glu Pro Asn Gly Glu Gly Trp Glu Trp Ser Ser Ser Asp Val Met
                115                 120                 125

Asn Tyr Phe Ala Trp Glu Arg Asn Pro Ser Thr Ile Ser Ser Pro Gly
130                 135                 140

His Cys Ala Ser Leu Ser Arg Ser Thr Ala Phe Leu Arg Trp Lys Asp
```

-continued

```
            145                 150                 155                 160
Tyr Asn Cys Asn Val Arg Leu Pro Tyr Val Cys Lys Phe Thr Asp
                165                 170                 175

<210> SEQ ID NO 6
<211> LENGTH: 919
<212> TYPE: PRT
<213> ORGANISM: Homo sapiens

<400> SEQUENCE: 6

Met Thr Gly Tyr Thr Met Leu Arg Asn Gly Ala Gly Asn Gly Gly
1               5                   10                  15

Gln Thr Cys Met Leu Arg Trp Ser Asn Arg Ile Arg Leu Thr Trp Leu
                20                  25                  30

Ser Phe Thr Leu Phe Val Ile Leu Val Phe Phe Pro Leu Ile Ala His
                35                  40                  45

Tyr Tyr Leu Thr Thr Leu Asp Glu Ala Asp Glu Ala Gly Lys Arg Ile
            50                  55                  60

Phe Gly Pro Arg Val Gly Asn Glu Leu Cys Glu Val Lys His Val Leu
65                  70                  75                  80

Asp Leu Cys Arg Ile Arg Glu Ser Val Ser Glu Glu Leu Leu Gln Leu
                85                  90                  95

Glu Ala Lys Arg Gln Glu Leu Asn Ser Glu Ile Ala Lys Leu Asn Leu
                100                 105                 110

Lys Ile Glu Ala Cys Lys Lys Ser Ile Glu Asn Ala Lys Gln Asp Leu
            115                 120                 125

Leu Gln Leu Lys Asn Val Ile Ser Gln Thr Glu His Ser Tyr Lys Glu
130                 135                 140

Leu Met Ala Gln Asn Gln Pro Lys Leu Ser Leu Pro Ile Arg Leu Leu
145                 150                 155                 160

Pro Glu Lys Asp Asp Ala Gly Leu Pro Pro Lys Ala Thr Arg Gly
                165                 170                 175

Cys Arg Leu His Asn Cys Phe Asp Tyr Ser Arg Cys Pro Leu Thr Ser
                180                 185                 190

Gly Phe Pro Val Tyr Val Tyr Asp Ser Asp Gln Phe Val Phe Gly Ser
            195                 200                 205

Tyr Leu Asp Pro Leu Val Lys Gln Ala Phe Gln Ala Thr Ala Arg Ala
    210                 215                 220

Asn Val Tyr Val Thr Glu Asn Ala Asp Ile Ala Cys Leu Tyr Val Ile
225                 230                 235                 240

Leu Val Gly Glu Met Gln Glu Pro Val Val Leu Arg Pro Ala Glu Leu
                245                 250                 255

Glu Lys Gln Leu Tyr Ser Leu Pro His Trp Arg Thr Asp Gly His Asn
                260                 265                 270

His Val Ile Ile Asn Leu Ser Arg Lys Ser Asp Thr Gln Asn Leu Leu
            275                 280                 285

Tyr Asn Val Ser Thr Gly Arg Ala Met Val Ala Gln Ser Thr Phe Tyr
    290                 295                 300

Thr Val Gln Tyr Arg Pro Gly Phe Asp Leu Val Val Ser Pro Leu Val
305                 310                 315                 320

His Ala Met Ser Glu Pro Asn Phe Met Glu Ile Pro Gln Val Pro
                325                 330                 335

Val Lys Arg Lys Tyr Leu Phe Thr Phe Gln Gly Glu Lys Ile Glu Ser
                340                 345                 350
```

```
Leu Arg Ser Ser Leu Gln Glu Ala Arg Ser Phe Glu Glu Met Glu
        355                 360                 365

Gly Asp Pro Pro Ala Asp Tyr Asp Asp Arg Ile Ile Ala Thr Leu Lys
370                 375                 380

Ala Val Gln Asp Ser Lys Leu Asp Gln Val Leu Val Glu Phe Thr Cys
385                 390                 395                 400

Lys Asn Gln Pro Lys Pro Ser Leu Pro Thr Glu Trp Ala Leu Cys Gly
                405                 410                 415

Glu Arg Glu Asp Arg Leu Glu Leu Leu Lys Leu Ser Thr Phe Ala Leu
            420                 425                 430

Ile Ile Thr Pro Gly Asp Pro Arg Leu Val Ile Ser Ser Gly Cys Ala
        435                 440                 445

Thr Arg Leu Phe Glu Ala Leu Glu Val Gly Ala Val Pro Val Val Leu
    450                 455                 460

Gly Glu Gln Val Gln Leu Pro Tyr Gln Asp Met Leu Gln Trp Asn Glu
465                 470                 475                 480

Ala Ala Leu Val Val Pro Lys Pro Arg Val Thr Glu Val His Phe Leu
                485                 490                 495

Leu Arg Ser Leu Ser Asp Ser Asp Leu Leu Ala Met Arg Arg Gln Gly
            500                 505                 510

Arg Phe Leu Trp Glu Thr Tyr Phe Ser Thr Ala Asp Ser Ile Phe Asn
        515                 520                 525

Thr Val Leu Ala Met Ile Arg Thr Arg Ile Gln Ile Pro Ala Ala Pro
    530                 535                 540

Ile Arg Glu Glu Ala Ala Ala Glu Ile Pro His Arg Ser Gly Lys Ala
545                 550                 555                 560

Ala Gly Thr Asp Pro Asn Met Ala Asp Asn Gly Asp Leu Asp Leu Gly
                565                 570                 575

Pro Val Glu Thr Glu Pro Pro Tyr Ala Ser Pro Arg Tyr Leu Arg Asn
            580                 585                 590

Phe Thr Leu Thr Val Thr Asp Phe Tyr Arg Ser Trp Asn Cys Ala Pro
        595                 600                 605

Gly Pro Phe His Leu Phe Pro His Thr Pro Phe Asp Pro Val Leu Pro
610                 615                 620

Ser Glu Ala Lys Phe Leu Gly Ser Gly Thr Gly Phe Arg Pro Ile Gly
625                 630                 635                 640

Gly Gly Ala Gly Gly Ser Gly Lys Glu Phe Gln Ala Ala Leu Gly Gly
                645                 650                 655

Asn Val Pro Arg Glu Gln Phe Thr Val Val Met Leu Thr Tyr Glu Arg
            660                 665                 670

Glu Glu Val Leu Met Asn Ser Leu Glu Arg Leu Asn Gly Leu Pro Tyr
        675                 680                 685

Leu Asn Lys Val Val Val Val Trp Asn Ser Pro Lys Leu Pro Ser Glu
    690                 695                 700

Asp Leu Leu Trp Pro Asp Ile Gly Val Pro Ile Met Val Val Arg Thr
705                 710                 715                 720

Glu Lys Asn Ser Leu Asn Asn Arg Phe Leu Pro Trp Asn Glu Ile Glu
                725                 730                 735

Thr Glu Ala Ile Leu Ser Ile Asp Asp Asp Ala His Leu Arg His Asp
            740                 745                 750

Glu Ile Met Phe Gly Phe Arg Val Trp Arg Glu Ala Arg Asp Arg Ile
        755                 760                 765

Val Gly Phe Pro Gly Arg Tyr His Ala Trp Asp Ile Pro His Gln Ser
```

```
                    770                 775                 780
Trp Leu Tyr Asn Ser Asn Tyr Ser Cys Glu Leu Ser Met Val Leu Thr
785                 790                 795                 800

Gly Ala Ala Phe Phe His Lys Tyr Tyr Ala Tyr Leu Tyr Ser Tyr Val
                    805                 810                 815

Met Pro Gln Ala Ile Arg Asp Met Val Asp Glu Tyr Ile Asn Cys Glu
                820                 825                 830

Asp Ile Ala Met Asn Phe Leu Val Ser His Ile Thr Arg Lys Pro Pro
            835                 840                 845

Ile Lys Val Thr Ser Arg Trp Thr Phe Arg Cys Pro Gly Cys Pro Gln
        850                 855                 860

Ala Leu Ser His Asp Asp Ser His Phe His Glu Arg His Lys Cys Ile
865                 870                 875                 880

Asn Phe Phe Val Lys Val Tyr Gly Tyr Met Pro Leu Leu Tyr Thr Gln
                    885                 890                 895

Phe Arg Val Asp Ser Val Leu Phe Lys Thr Arg Leu Pro His Asp Lys
                900                 905                 910

Thr Lys Cys Phe Lys Phe Ile
        915

<210> SEQ ID NO 7
<211> LENGTH: 7
<212> TYPE: PRT
<213> ORGANISM: Homo sapiens

<400> SEQUENCE: 7

Trp Ile Gly Leu His Asp Pro
1               5

<210> SEQ ID NO 8
<211> LENGTH: 8
<212> TYPE: PRT
<213> ORGANISM: Homo sapiens

<400> SEQUENCE: 8

Trp Ile Gly Leu His Asp Pro Thr
1               5

<210> SEQ ID NO 9
<211> LENGTH: 20
<212> TYPE: PRT
<213> ORGANISM: Homo sapiens

<400> SEQUENCE: 9

Cys Lys Lys Ser Ile Glu Asn Ala Lys Gln Asp Leu Leu Gln Leu Lys
1               5                   10                  15

Asn Val Ile Ser
            20

<210> SEQ ID NO 10
<211> LENGTH: 158
<212> TYPE: PRT
<213> ORGANISM: Homo sapiens

<400> SEQUENCE: 10

Met Ala Ser Arg Ser Met Arg Leu Leu Leu Leu Ser Cys Leu Ala
1               5                   10                  15

Lys Thr Gly Val Leu Gly Asp Ile Ile Met Arg Pro Ser Cys Ala Pro
            20                  25                  30
```

Gly Trp Phe Tyr His Lys Ser Asn Cys Tyr Gly Tyr Phe Arg Lys Leu
            35                  40                  45

Arg Asn Trp Ser Asp Ala Glu Leu Glu Cys Gln Ser Tyr Gly Asn Gly
 50                  55                  60

Ala His Leu Ala Ser Ile Leu Ser Leu Lys Glu Ala Ser Thr Ile Ala
 65                  70                  75                  80

Glu Tyr Ile Ser Gly Tyr Gln Arg Ser Gln Pro Ile Trp Ile Gly Leu
                 85                  90                  95

His Asp Pro Gln Lys Arg Gln Gln Trp Gln Trp Ile Asp Gly Ala Met
            100                 105                 110

Tyr Leu Tyr Arg Ser Trp Ser Gly Lys Ser Met Gly Gly Asn Lys His
            115                 120                 125

Cys Ala Glu Met Ser Ser Asn Asn Asn Phe Leu Thr Trp Ser Ser Asn
130                 135                 140

Glu Cys Asn Lys Arg Gln His Phe Leu Cys Lys Tyr Arg Pro
145                 150                 155

<210> SEQ ID NO 11
<211> LENGTH: 14
<212> TYPE: PRT
<213> ORGANISM: Homo sapiens

<400> SEQUENCE: 11

Ile Gly Leu His Asp Pro Thr Gln Gly Thr Glu Pro Asn Gly
1               5                   10

<210> SEQ ID NO 12
<211> LENGTH: 15
<212> TYPE: PRT
<213> ORGANISM: Mesocricetus auratus

<400> SEQUENCE: 12

Ile Gly Leu His Asp Pro Ser His Gly Thr Leu Pro Asn Gly Ser
1               5                   10                  15

<210> SEQ ID NO 13
<211> LENGTH: 333
<212> TYPE: PRT
<213> ORGANISM: Homo sapiens

<400> SEQUENCE: 13

Met Thr Gly Tyr Thr Met Leu Arg Asn Gly Ala Gly Asn Gly Gly
1               5                   10                  15

Gln Thr Cys Met Leu Arg Trp Ser Asn Arg Ile Arg Leu Thr Trp Leu
            20                  25                  30

Ser Phe Thr Leu Phe Val Ile Leu Val Phe Phe Pro Leu Ile Ala His
            35                  40                  45

Tyr Tyr Leu Thr Thr Leu Asp Glu Ala Asp Glu Ala Gly Lys Arg Ile
 50                  55                  60

Phe Gly Pro Arg Val Gly Asn Glu Leu Cys Glu Val Lys His Val Leu
 65                  70                  75                  80

Asp Leu Cys Arg Ile Arg Glu Ser Val Ser Glu Glu Leu Leu Gln Leu
                 85                  90                  95

Glu Ala Lys Arg Gln Glu Leu Asn Ser Glu Ile Ala Lys Leu Asn Leu
            100                 105                 110

Lys Ile Glu Ala Cys Lys Lys Ser Ile Glu Asn Ala Lys Gln Asp Leu
            115                 120                 125

Leu Gln Leu Lys Asn Val Ile Ser Gln Thr Glu His Ser Tyr Lys Glu

```
                    130                 135                 140
Leu Met Ala Gln Asn Gln Pro Lys Leu Ser Leu Pro Ile Arg Leu Leu
145                 150                 155                 160

Pro Glu Lys Asp Asp Ala Gly Leu Pro Pro Pro Lys Ala Thr Arg Gly
                165                 170                 175

Cys Arg Leu His Asn Cys Phe Asp Tyr Ser Arg Cys Pro Leu Thr Ser
                180                 185                 190

Gly Phe Pro Val Tyr Val Tyr Asp Ser Asp Gln Phe Val Phe Gly Ser
            195                 200                 205

Tyr Leu Asp Pro Leu Val Lys Gln Ala Phe Gln Ala Thr Ala Arg Ala
        210                 215                 220

Asn Val Tyr Val Thr Glu Asn Ala Asp Ile Ala Cys Leu Tyr Val Ile
225                 230                 235                 240

Leu Val Gly Glu Met Gln Glu Pro Val Val Leu Arg Pro Ala Glu Leu
                245                 250                 255

Glu Lys Gln Leu Tyr Ser Leu Pro His Trp Arg Thr Asp Gly His Asn
                260                 265                 270

His Val Ile Ile Asn Leu Ser Arg Lys Ser Asp Thr Gln Asn Leu Leu
            275                 280                 285

Tyr Asn Val Ser Thr Gly Arg Ala Met Val Ala Gln Ser Thr Phe Tyr
        290                 295                 300

Thr Val Gln Tyr Arg Pro Gly Phe Asp Leu Val Val Ser Pro Leu Val
305                 310                 315                 320

His Ala Met Ser Glu Pro Asn Phe Met Glu Ile Pro Pro
                325                 330

<210> SEQ ID NO 14
<211> LENGTH: 9
<212> TYPE: PRT
<213> ORGANISM: Homo sapiens

<400> SEQUENCE: 14

Val Trp Ile Gly Leu His Asp Pro Thr
1               5
```